United States Patent
McVerry et al.

(10) Patent No.: US 11,258,134 B2
(45) Date of Patent: Feb. 22, 2022

(54) ENERGY PROVIDING DEVICES AND APPLICATIONS THEREOF

(71) Applicant: The Regents of the University of California, Oakland, CA (US)

(72) Inventors: Brian T. McVerry, Laguna Hills, CA (US); Ethan Rao, Los Angeles, CA (US); Robert S. Jordan, Merced, CA (US); Richard B. Kaner, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 177 days.

(21) Appl. No.: 16/795,138

(22) Filed: Feb. 19, 2020

(65) Prior Publication Data
US 2020/0203692 A1    Jun. 25, 2020

Related U.S. Application Data

(63) Continuation of application No. 15/827,788, filed on Nov. 30, 2017, now Pat. No. 10,629,880.
(Continued)

(51) Int. Cl.
| | |
|---|---|
| *H01M 4/02* | (2006.01) |
| *H01M 50/411* | (2021.01) |
| *H01M 8/0221* | (2016.01) |
| *H01M 4/583* | (2010.01) |
| *C07C 309/14* | (2006.01) |
| *C07C 211/62* | (2006.01) |

(Continued)

(52) U.S. Cl.
CPC ......... *H01M 50/411* (2021.01); *C07C 211/62* (2013.01); *C07C 247/16* (2013.01); *C07C 309/14* (2013.01); *C07C 309/88* (2013.01); *C07C 311/37* (2013.01); *H01M 4/583* (2013.01); *H01M 8/0221* (2013.01); *H01M 8/106* (2013.01)

(58) Field of Classification Search
CPC ...................................................... H01M 4/02
See application file for complete search history.

(56) References Cited

U.S. PATENT DOCUMENTS

| | | |
|---|---|---|
| 3,796,314 A | 3/1974 | Kolek |
| 5,753,008 A | 5/1998 | Friesen et al. |

(Continued)

FOREIGN PATENT DOCUMENTS

| | | |
|---|---|---|
| CN | 102067365 A | 5/2011 |
| CN | 105854628 A | 8/2016 |

(Continued)

OTHER PUBLICATIONS

EIC search report for U.S. Appl. No. 16/404,372 (dated 2020).
(Continued)

*Primary Examiner* — Jacob B Marks
(74) *Attorney, Agent, or Firm* — Foley Hoag LLP; David P. Halstead; David S. Surry

(57) ABSTRACT

Disclosed herein are compositions for use in an energy providing devices and methods of preparing such devices. Also included herein is energy providing devices that comprise a charged compound modified substrate or zwitterion-modified substrate or energy providing devices that comprise an electrolyte that comprises a perhalogenatedphenyl azide charged or zwitterionic compound.

20 Claims, 15 Drawing Sheets

Related U.S. Application Data

(60) Provisional application No. 62/588,613, filed on Nov. 20, 2017, provisional application No. 62/428,899, filed on Dec. 1, 2016.

(51) Int. Cl.
```
C07C 309/88    (2006.01)
H01M 8/106     (2016.01)
C07C 311/37    (2006.01)
C07C 247/16    (2006.01)
```

(56) References Cited

U.S. PATENT DOCUMENTS

| | | |
|---|---|---|
| 8,029,857 B2 | 10/2011 | Hoek et al. |
| 8,132,677 B2 | 3/2012 | Liu et al. |
| 8,530,269 B2 | 9/2013 | Chua et al. |
| 8,550,256 B1 | 10/2013 | Diep et al. |
| 9,662,617 B2 | 5/2017 | Hoek et al. |
| 10,315,169 B2 | 6/2019 | Hoek et al. |
| 10,629,880 B2 | 4/2020 | McVerry et al. |
| 10,729,822 B2 | 8/2020 | Kaner et al. |
| 11,084,002 B2 | 8/2021 | Kaner et al. |
| 2002/0122872 A1 | 9/2002 | Leukel et al. |
| 2007/0254006 A1 | 11/2007 | Loose et al. |
| 2008/0017512 A1 | 1/2008 | Bordunov et al. |
| 2009/0155335 A1 | 6/2009 | O'Shaughnessey et al. |
| 2009/0308804 A1 | 12/2009 | Cohen et al. |
| 2011/0005997 A1 | 1/2011 | Kurth et al. |
| 2011/0104573 A1* | 5/2011 | Gogichev ............ H01M 6/045 429/303 |
| 2012/0201972 A1 | 8/2012 | Hayashi et al. |
| 2012/0258313 A1 | 10/2012 | Wen et al. |
| 2014/0206251 A1 | 7/2014 | Stokes |
| 2015/0025168 A1 | 1/2015 | Lienkamp et al. |
| 2016/0001236 A1 | 1/2016 | Hoek et al. |
| 2016/0152008 A1 | 6/2016 | Ogata et al. |
| 2017/0296986 A1 | 10/2017 | Hoek et al. |
| 2017/0355799 A1 | 12/2017 | Veiseh et al. |
| 2018/0159106 A1 | 6/2018 | McVerry et al. |
| 2019/0185776 A1 | 6/2019 | Kuramoto et al. |
| 2020/0203692 A1 | 6/2020 | McVerry et al. |
| 2020/0338240 A1 | 10/2020 | Kaner et al. |
| 2020/0385506 A1 | 12/2020 | McVerry et al. |

FOREIGN PATENT DOCUMENTS

| | | |
|---|---|---|
| FR | 2989215 | 10/2013 |
| FR | 2989215 A1 | 10/2013 |
| JP | 56067848 | 6/1981 |
| JP | 56067848 A | 7/1981 |
| JP | 2010059346 | 3/2010 |
| JP | 2010059346 A | 3/2010 |
| JP | 2017177754 | 10/2017 |
| JP | 2017177754 A | 10/2017 |
| TW | 201311750 A | 3/2013 |
| WO | 00/076641 | 12/2000 |
| WO | WO-00/076641 A1 | 12/2000 |
| WO | 2004/100282 | 11/2004 |
| WO | WO-2004/100282 A2 | 11/2004 |
| WO | 2009/039467 | 3/2009 |
| WO | WO-2009/039467 A1 | 3/2009 |
| WO | 2009/099126 | 8/2009 |
| WO | WO-2009/099126 A1 | 8/2009 |
| WO | 2010/006196 | 1/2010 |
| WO | WO-2010/006196 A2 | 1/2010 |
| WO | 2010/036452 | 4/2010 |
| WO | WO-2010/036452 A2 | 4/2010 |
| WO | 2011/060202 | 5/2011 |
| WO | WO-2011/060202 A1 | 5/2011 |
| WO | 2012/071461 | 5/2012 |
| WO | WO-2012/071461 A2 | 5/2012 |
| WO | 2014/001795 | 1/2014 |
| WO | WO-2014/001795 A1 | 1/2014 |
| WO | 2014/032005 | 2/2014 |
| WO | WO-2014/032005 A1 | 2/2014 |
| WO | 2016/083314 | 6/2016 |
| WO | WO-2016/083314 A1 | 6/2016 |
| WO | WO-2017170210 A1 | 10/2017 |
| WO | 2018/102517 | 6/2018 |
| WO | WO-2018/102517 A1 | 6/2018 |
| WO | WO-2019/094685 A1 | 5/2019 |
| WO | 2019/108871 | 6/2019 |
| WO | WO-2019/108871 A1 | 6/2019 |
| WO | WO-2020/247629 A1 | 12/2020 |

OTHER PUBLICATIONS

Gerard et al., "Surface modification of poly(butylene terephthalate) nonwoven by photochemistry and biofunctionalization with peptides for blood filtration," Polymer Chemistry, 49(23): 5087-5099 (2011).

International Search Report and Written Opinion for International Application No. PCT/US2020/036121 dated Aug. 19, 2020.

Tanaka et al., "Synthesis and structures of zwitterionic polymers to induce electrostatic interaction with PDMS surface treated by air-plasma," Organic Chemistry, part ii:330-343 (2018).

Anderson et al., "Conjugated Polymer Films for Gas Separations," Sci 252(5011):1412-1415 (1991).

Batool et al., "Fabrication of covalently bonded nanostructured thin films of epoxy resin and polydimethylsiloxane for oil adsorption," Polymer Bulletin, 74(12):4827-4840 (2017).

Extended European Search Report issued by the European Patent Office in corresponding Application No. EP 14753770, dated Oct. 24, 2016.

Freger et al., "TFC polyamide membranes modified by grafting of hydrophilic polymers: an FT-IR/AFM/TEM study," J Mem Sci, 209:283-292 (2002).

International Search Report and Written Opinion for International Application No. PCT/US14/17758 dated May 30, 2014.

International Search Report and Written Opinion for International Application No. PCT/US17/63887 dated Jan. 26, 2018.

International Search Report and Written Opinion for International Application No. PCT/US2018/059967 dated Feb. 17, 2019.

International Search Report and Written Opinion for International Application No. PCT/US2018/063196 dated Mar. 10, 2019.

Khulbe et al., "The art of surface modification of synthetic polymeric membranes," J Appl Ploymer Sci, 115(2): 855-895 (2010).

Kuo et al., "Surface modification with poly(sulfobetaine methacrylate-co-acrylic acid) to reduce fibrinogen adsorption, platelet adhesion, and plasma coagulation," Biomacromolecules, 12(12):4348-4356 (2011).

Li et al., "Influence of polybenzimidazole main chain structure on $H_2/CO_2$ separation at elevated temperatures," Journal of Membrane Science, 461:59-68 (2014).

Liu et al., "Perfluorophenyl Azides: New Applications in Surface Functionalization and Nanomaterial Synthesis," Acc Chem Res, 43(11):1434-1443 (2010).

Liu et al., "Photoinitiated coupling of unmodified monosaccharides to iron oxide nanoparticles for sensing proteins and bacteria," Bioconjugate Chem, 20(7): 1349-1355 (2009).

Mandwar et al., "Perfluorophenyl azide immobilization chemistry for single molecule force spectroscopy of the concanavalin A/mannose interaction," Langmuir, 26(22): 16677-16680 (2010).

Mizutani et al., "Liquid, phenylazide-end-capped copolymers of epsilon-caprolactone and trimethylene carbonate: preparation, photocuring characteristics, and surface layering," Biomacromolecules, 3(4):668-675 (2002).

Mosnacek et al., "Photochemical grafting of polysulfobetaine onto polyethylene and polystyrene surfaces and investigation of long-term stability of the polysulfobetaine layer in seawater," Polymers for Advanced Technologies, 29(7):1930-1938 (2018).

Puleo et al., "Gas sorption and transport in substituted polystyrenes," Journal of Polymer Science Part B: Polymer Physics, 27(11):2385-2406 (1989).

Qureshi et al., "Nanoprotective layer-by-layer coatings with epoxy components for enhancing abrasion resistance: toward robust multimaterial nanoscale films," Acs Nano, 7(10):9336-9344 (2013).

(56) References Cited

OTHER PUBLICATIONS

Sakuragi et al., "A photoimmobilizable sulfobetaine-based polymer for a nonbiofouling surface," Materials Science and Engineering:C, 30(2):316-322 (2010).

Seo et al., "Simultaneous patterning of proteins and cells through bioconjugation with photoreactable phospholipid polymers," RSC Advances, 7(64):40669-40672 (2017).

Sivakumar et al., "Novel Microarrays for Simultaneous of Multiple Antiviral Antibodies," Plos One, 8(12):e81726/1-e81726/9 (2013).

Sundhoro et al., "Fabrication of carbohydrate microarrays on a poly (2-hydroxyethyl methacrylate)-based photoactive substrate," Organic & Biomolecular Chemistry, 14(3):1124-1130 (2015).

Sundhoro et al., "Poly(HEMA-co-HEMA-PFA): Synthesis and preparation of stable micelles encapsulating imaging nanoparticles," Journal of Colloid and Interface Science, 500:1-8 (2017).

Yuwen, "Polymer-based photoactive surface for the efficient immobilization of nanoparticles, polymers, graphene and; carbohydrates," PDXScholar, Dissertation, Portland State University (2011).

U.S. Appl. No. 14/768,887, Granted.
U.S. Appl. No. 15/581,783, Granted.
U.S. Appl. No. 16/404,372, Pending.
U.S. Appl. No. 15/827,788, Allowed.
U.S. Appl. No. 16/206,596, Pending.

Extended European Search Report for EP Application No. 18876572.1 dated Jul. 9, 2021.

Extended European Search Report for EP Application No. 18882865.1 dated Jul. 23, 2021.

Extender European Search Report for EP Application No. 17876218.3 dated Mar. 24, 2020.

Khong et al., "General Photo-Patterning of Polyelectrolyte Thin Films via Efficient Ionic Bis(Fluorinated Phenyl Azide) Photo-Crosslinkers and their Post-Deposition Modification," Advanced Functional Materials, 17(14): 2490-2499 (2007).

\* cited by examiner

ENERGY PROVIDING DEVICES AND APPLICATIONS THEREOF

CROSS-REFERENCE TO RELATED APPLICATIONS

This application is a continuation of U.S. patent application Ser. No. 15/827,788, filed Nov. 30, 2017, which claims the benefit of U.S. Provisional Application No. 62/428,899, filed Dec. 1, 2016, and U.S. Provisional Application No. 62/588,613, filed Nov. 20, 2017, the contents of each of which are fully incorporated by reference herein in their entirety.

STATEMENT AS TO FEDERALLY SPONSORED RESEARCH

This invention was made with government support under Grant Number 1337065, awarded by the National Science Foundation. The government has certain rights in the invention.

BACKGROUND OF THE DISCLOSURE

Renewable energy resources such as wind, solar, and hydroelectricity are alternative energy sources to traditional fossil energy. In some instances, the shortcomings of renewable energy include their variability and intermittent power generation. As such, energy storage devices such as batteries, flywheels, and supercapacitors have been used to ensure delivery of continuous and stable energy supplies.

SUMMARY OF THE DISCLOSURE

Disclosed herein, in certain embodiments, are energy providing devices, compositions for use in an energy providing device, and methods of preparing such device.

An advantage of the devices, compositions, and methods described herein is the ability to functionalize polyolefin separators for use in LiBs. In some cases, the methods utilize PFPA photochemistry and a roll-to-roll modification system allowing for production of several meters of modified separator at low cost. In some cases, compared to untreated commercial separators, the modified separators exhibit dramatically improved wettability with LiB electrolytes, an important factor in battery manufacturing processes. In some cases, the modified separators are wet by a much wider range of electrolytes than current commercial separators, allowing for further investigation into electrolytes previously hindered by incompatibility with separators, notable those composed only of cyclic carbonates. In some cases, the modification of commercial PE and PP/PE/PE separators with polar PFPA-sulfobetaine molecules increases the surface energy and hydrophilicity of the polyolefin separators. These improvements to commercial separators can increase the discharge capacity of NMC/graphite full cells made with commercial electrolyte cycled at several different C-rates. Use of the modified separators may also allow for the commercialization of more thermally stable or high voltage electrolytes which have previously been hindered by incompatibility with commercially available polyolefin separators.

In some embodiments, disclosed herein is an energy providing device comprising a substrate modified by a charged compound. In some embodiments, disclosed herein is an energy providing device comprising a zwitterion-modified substrate. In some embodiments, the charged compound modified substrate or zwitterion-modified substrate comprises a compound that has the structure of Formula I:

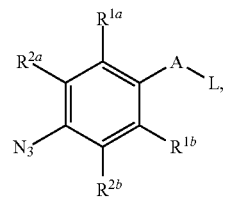

Formula I wherein A is selected from —C(=O)— and —(SO$_2$)—; L is selected from —OQ, —O$^-$, —N$^+$R$^3$HQ and —NR$^3$Q; Q is a structure represented by a formula:

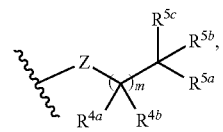

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl; R$^{13}$, when present, is selected from hydrogen and C1-C4 alkyl, and that the compound is charged or zwitterionic. In some embodiments, the compound has a structure selected from:

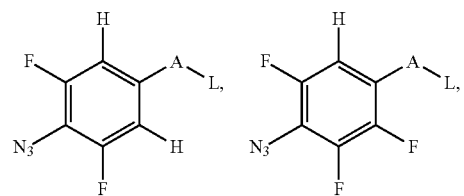

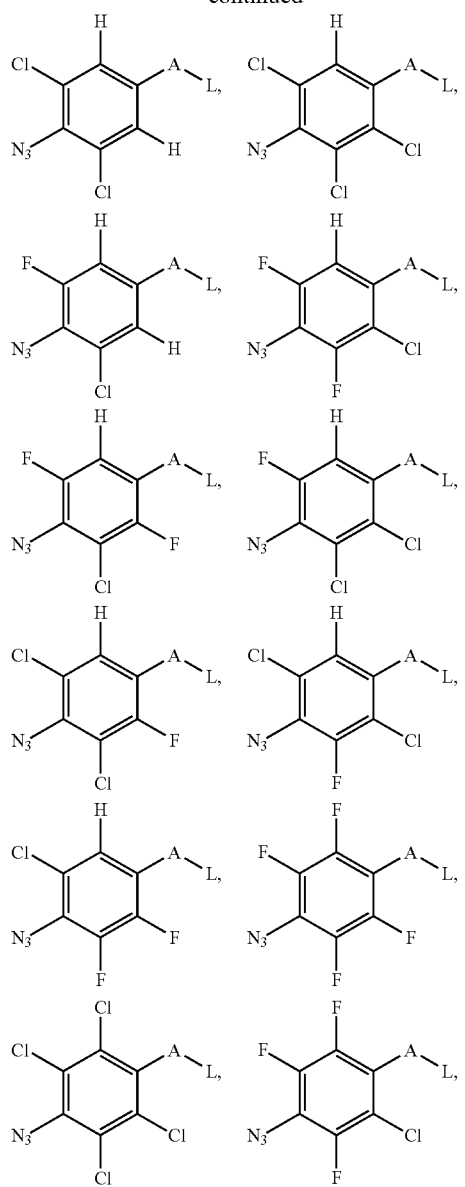
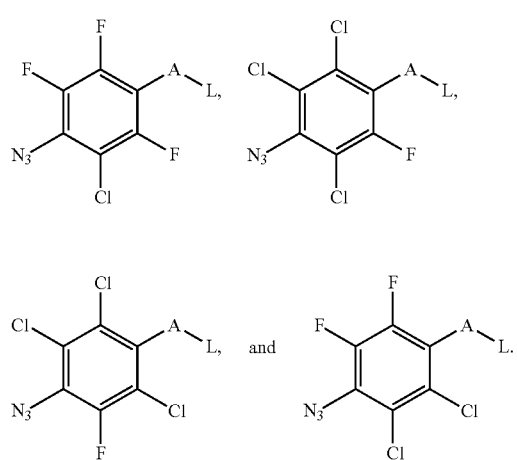
In some embodiments, the compound has a structure selected from:
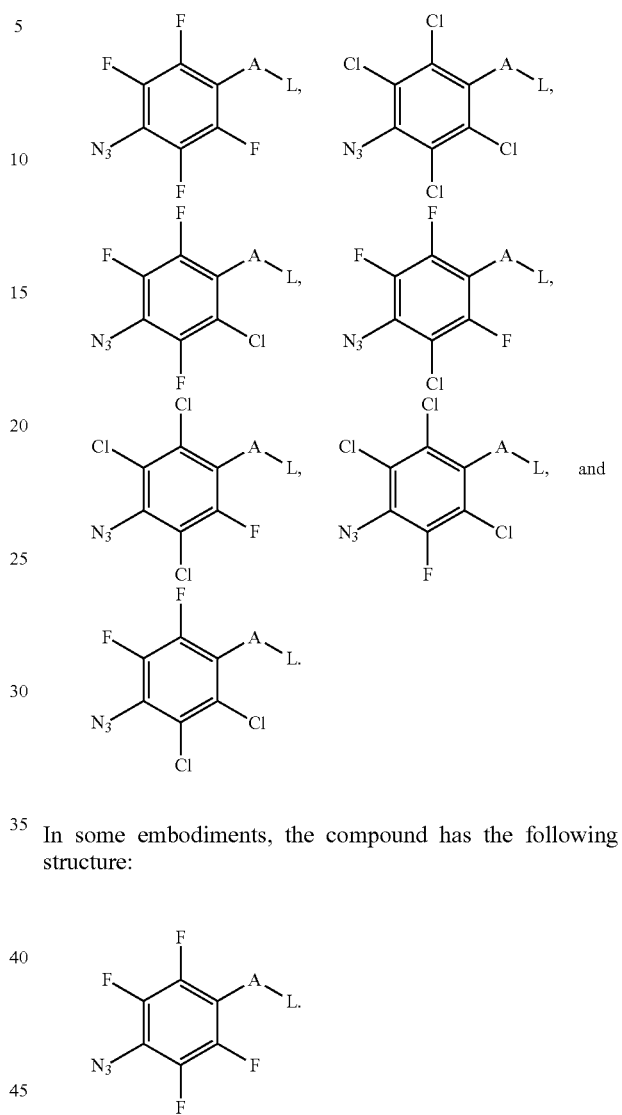
In some embodiments, the compound has the following structure:
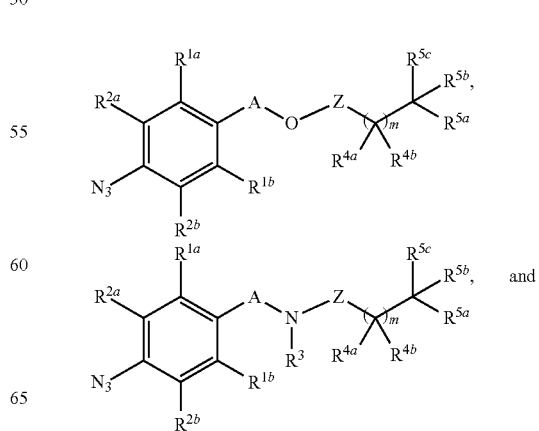
In some embodiments, the compound has the structure selected from:

-continued

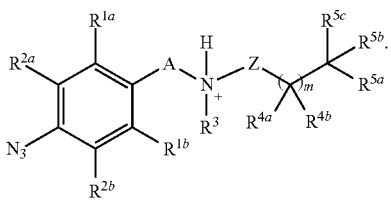

In some embodiments, the compound has the following structure:

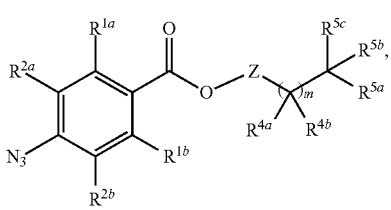

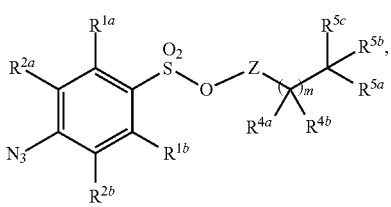

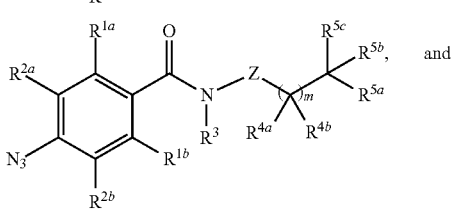

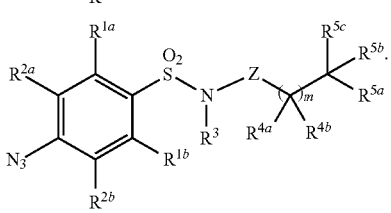

In some embodiments, $R^{1a}$, $R^{1b}$, $R^{2a}$, and $R^{2b}$ are each —F. In some embodiments, Q is selected from:

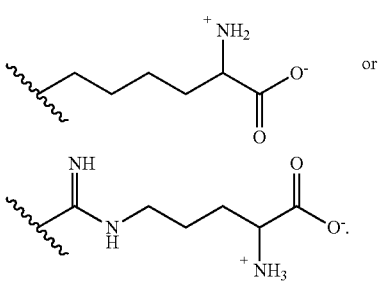

In some embodiments, Q is:

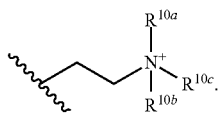

In some embodiments, Q is:

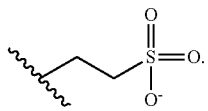

In some embodiments, Z is —$CR^{6a}R^{6b}$—. In some embodiments, $R^{6a}$ and $R^{6b}$ are each hydrogen. In some embodiments, m is 0, 1, 2, or 3. In some embodiments, m is 0. In some embodiments, $R^{5a}$ is —$NR^{10a}R^{10b}R^{10c+}$; $R^{5b}$ is hydrogen; and $R^{5c}$ is hydrogen. In some embodiments, the compound has the structure of Formula Ia:

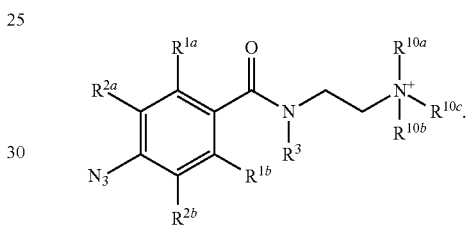

In some embodiments, the compound has the structure of Formula Ib:

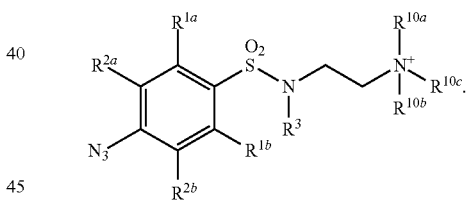

In some embodiments, $R^{10c}$ is —(C1-C8alkylene)$SO_3^-$, —(C1-C8alkylene)$SO_3H$, —(C1-C8alkylene)$CO_2$, or —(C1-C8alkylene)$CO_2H$. In some embodiments, $R^{10c}$ is —$CH_2CH_2CH_2$—$SO_3^-$, —$CH_2CH_2CH_2$—$SO_3H$, —$CH_2CH_2CH_2$—$CO_2$, or —$CH_2CH_2CH_2$—$CO_2H$. In some embodiments, $R^{10a}$ and $R^{10b}$ are each C1-C4alkyl. In some embodiments, $R^{10a}$ and $R^{10b}$ are each methyl. In some embodiments, $R^3$ is hydrogen. In some embodiments, the zwitterionic compound is

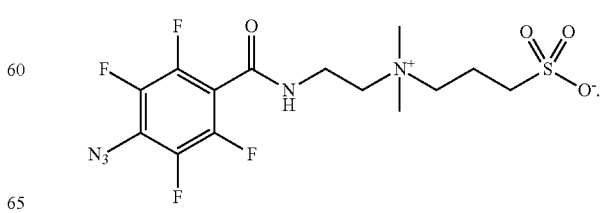

In some embodiments, the zwitterionic compound is

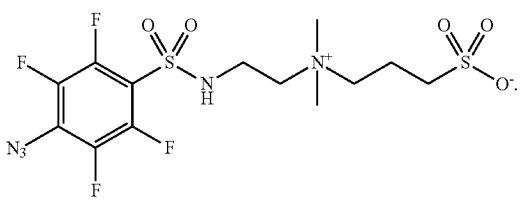

In some embodiments, the charged compound is

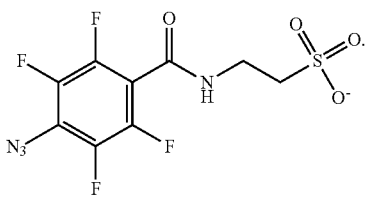

In some embodiments, the charged compound is

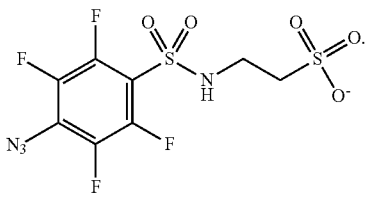 [SMILES: [N-]=[N+]=Nc1c(F)c(F)c(S(=O)(=O)NCCS(=O)(=O)[O-])c(F)c1F]

In some embodiments, the charged compound is

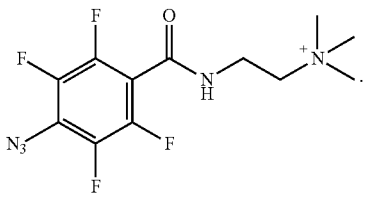

In some embodiments, the charged compound is

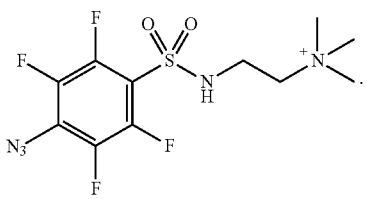

In some embodiments, the charged compound is

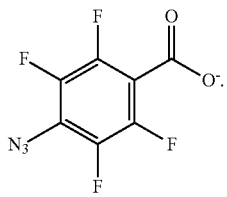

In some embodiments, the charged compound is

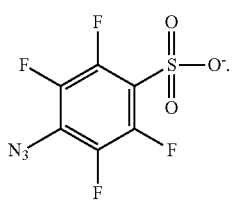

In some embodiments, the substrate comprises a separator. In some embodiments, the separator comprises a polymer-based separator. In some embodiments, the polymer-based separator comprises a polyolefinic separator. In some embodiments, the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some embodiments, the separator comprises a microporous separator, a nonwoven separator, an ion-exchange membrane, a supported liquid membrane, or a solid ion conductor. In some embodiments, the substrate comprises a carbon-based substrate containing a moiety capable of binding with a compound that has a structure of Formula I. In some embodiments, the carbon-based substrate comprises a polymer moiety. In some embodiments, the carbon-based substrate comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety. In some embodiments, the energy providing device further comprises an electrolyte disposed onto the charged compound modified substrate or zwitterion modified substrate. In some embodiments, the electrolyte is a polar electrolyte. In some embodiments, the electrolyte comprises a carbonate-based electrolyte. In some embodiments, the electrolyte comprises ethylene carbonate and propylene carbonate. In some embodiments, the electrolyte is an aqueous electrolyte. In some embodiments, the energy providing device further comprises an electrode. In some embodiments, the electrode is a carbon-based electrode. In some embodiments, the carbon-based electrode is a carbon-based substrate. In some embodiments, the graphene-based electrode comprises a porous graphene matrices. In some embodiments, the porous graphene matrices comprises a three-dimensional intercalated network of single or multiple layers of graphene sheets. In some embodiments, the graphene-based electrode comprises a corrugated carbon-carbon network. In some embodiments, a compound that has a structure of Formula I is further deposited on the corrugated carbon-carbon network. In some embodiments, the electrode is an anode. In some embodiments, the electrode is a cathode. In some embodiments, the energy providing device comprises a battery, a supercapacitor, or a fuel cell. In some embodiments, the energy providing device is a battery. In some embodiments, the battery comprises a primary cell or a secondary cell. In some embodiments, the battery comprises a lead acid cell, NiCad cell, NiMH cell, NaNiCl cell, Lithium Ion cell, Nickel Iron cell, Nickel Zinc cell, silver oxide, nickel hydrogen, or lithium polymer cell. In some embodiments, the battery comprises an ampoule battery, a flow battery, or a water activated battery. In some embodiments, the energy providing device is a supercapacitor. In some embodiments, the supercapacitor comprises an electrochemical double-layer capacitor (EDLC), a pseudocapacitor, or a hybrid supercapacitor. In some embodiments, the energy providing device is a fuel cell. In some embodiments, the energy providing device has a lower internal resistance relative to an equivalent energy providing device without the charged compound modified substrate or zwitterion modified substrate. In some embodiments, the energy providing device has an increased electrolyte uptake relative to an equivalent energy providing device without the charged compound modified substrate or zwitterion modified substrate. In some embodiments, the energy providing device has an increased charge transfer relative to an equivalent energy providing device without the charged compound modified substrate or zwitterion modified substrate. In some embodiments, the charge transfer is between an anode and a cathode. In some embodiments, the charge transfer is between an electrode and an electrolyte. In some embodiments, the energy providing device has an increased capacitance relative to an equivalent energy providing device without the charged compound modified substrate or zwitterion modified substrate.

Disclosed herein, in certain embodiments, is an energy providing device comprising: an electrolyte comprising a perhalogenatedphenyl azide charged or zwitterion compound, wherein the perhalogenatedphenyl azide charged or zwitterion compound has the structure of Formula I:

Formula I

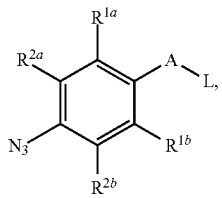

wherein A is selected from —C(=O)— and —(SO$_2$)—; L is selected from —OQ, —O$^-$, —N$^+$R$^3$HQ and —NR$^3$Q; Q is a structure represented by a formula:

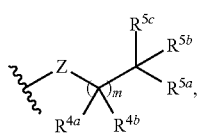

Z is selected from CR$^{6a}$R$^{6b}$, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, (C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl; R$^{13}$, when present, is selected from hydrogen and C1-C4 alkyl, and provided that the compound is charged or zwitterionic. In some embodiments, the compound has a structure selected from:

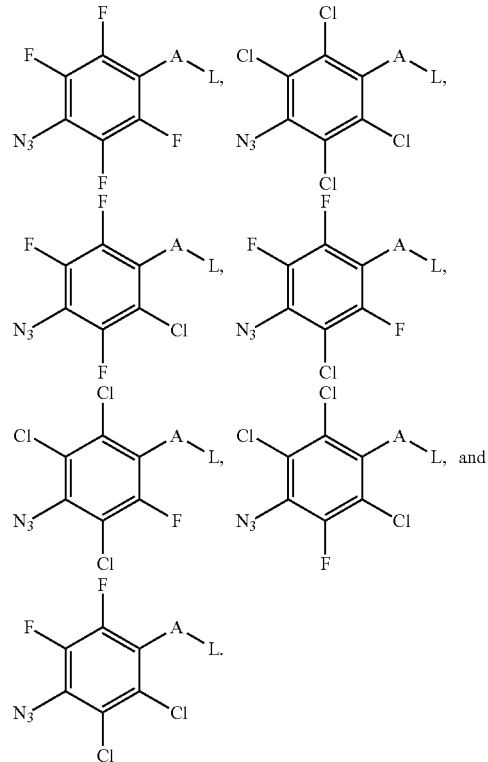

In some embodiments, the compound has the following structure:

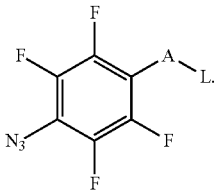

In some embodiments, the compound has the structure selected from:

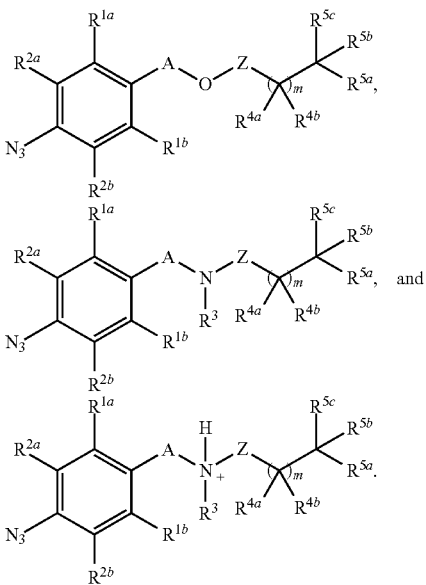

In some embodiments, the compound has the following structure:

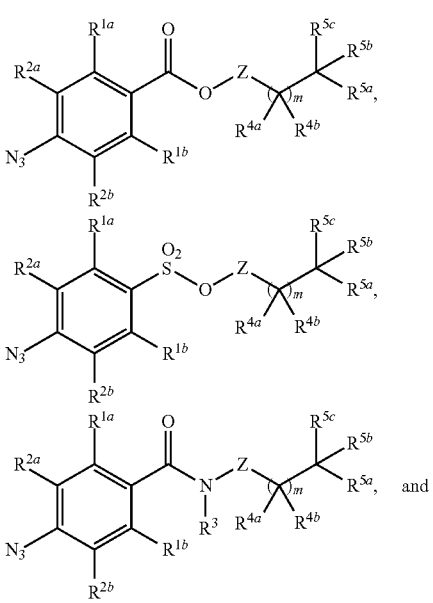

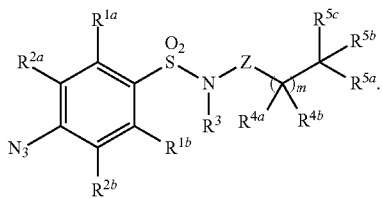

In some embodiments, $R^{1a}$, $R^{1b}$, $R^{2a}$, and $R^{2b}$ are each —F.
In some embodiments, Q is selected from:

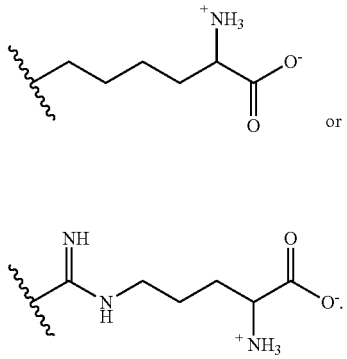

or

In some embodiments, Q is:

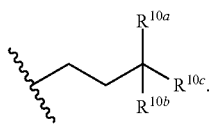

In some embodiments, Q is:

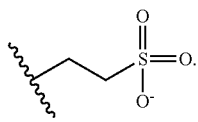

In some embodiments, Z is —$CR^{6a}R^{6b}$—. In some embodiments, $R^{6a}$ and $R^{6b}$ are each hydrogen. In some embodiments, m is 0, 1, 2, or 3. In some embodiments, m is 0. In some embodiments, $R^{5a}$ is —$NR^{10a}R^{10b}R^{10c+}$; $R^{5b}$ is hydrogen; and $R^{5c}$ is hydrogen. In some embodiments, the compound has the structure of Formula Ia:

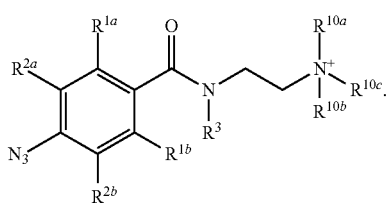

In some embodiments, the compound has the structure of Formula Ib:

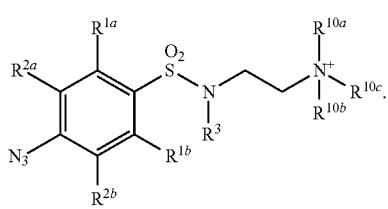

In some embodiments, $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$. In some embodiments, $R^{10a}$ and $R^{10b}$ are each C1-C4 alkyl. In some embodiments, $R^{10a}$ and $R^{10b}$ are each methyl. In some embodiments, $R^3$ is hydrogen. In some embodiments, the zwitterionic compound is

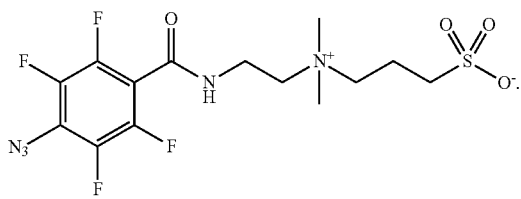

In some embodiments, the zwitterionic compound is

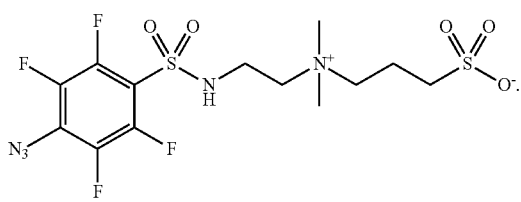

In some embodiments, the charged compound is

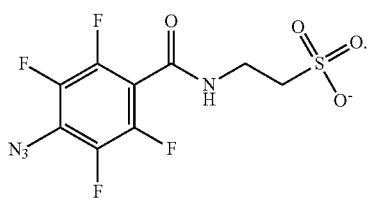

In some embodiments, the charged compound is

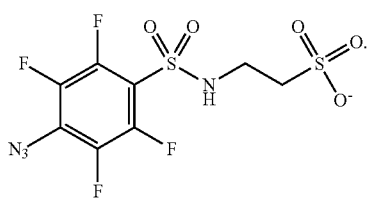 [SMILES: [N-]=[N+]=Nc1c(F)c(F)c(S(=O)(=O)NCCS(=O)(=O)[O-])c(F)c1F]

In some embodiments, the charged compound is

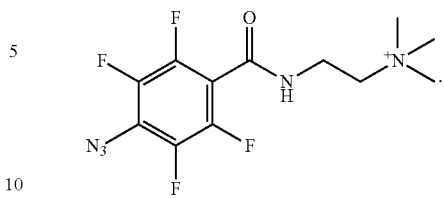

In some embodiments, the charged compound is

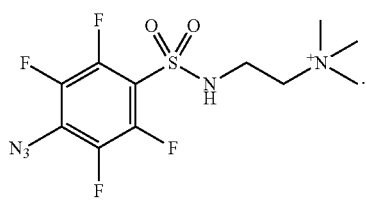 [SMILES: C[N+](C)(C)CCNS(=O)(=O)c1c(F)c(F)c(N=[N+]=[N-])c(F)c1F]

In some embodiments, the charged compound is

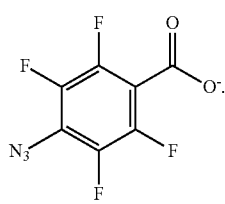

In some embodiments, the charged compound is

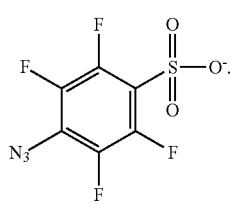

In some embodiments, the electrolyte is a polar electrolyte. In some embodiments, the electrolyte comprises a carbonate-based electrolyte. In some embodiments, the electrolyte comprises ethylene carbonate and propylene carbonate. In some embodiments, the electrolyte is an aqueous electrolyte. In some embodiments, the energy providing device further comprises a separator and an electrode. In some embodiments, the separator comprises a polymer-based separator. In some embodiments, the polymer-based separator comprises a polyolefinic separator. In some embodiments, the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some embodiments, the separator comprises a microporous separator, a nonwoven separator, an ion-exchange membrane, a supported liquid membrane, or a solid ion conductor. In some embodiments, the electrode is a carbon-based electrode. In some embodiments, the carbon-based electrode is a graphene-based electrode. In some embodiments, the graphene-based electrode comprises a porous graphene matrices. In some embodiments, the porous graphene matrices comprises a three-dimensional intercalated network of single or multiple layers of graphene sheets. In some embodiments, the graphene-based electrode comprises a corrugated carbon-carbon network. In some embodiments, the electrolyte comprising a perhalogenated-phenyl azide charged or zwitterion compound is further deposited on the corrugated carbon-carbon network. In some embodiments, the electrode is an anode. In some embodiments, the electrode is a cathode. In some embodiments, the energy providing device comprises a battery, a supercapacitor, or a fuel cell. In some embodiments, the energy providing device is a battery. In some embodiments, the battery comprises a primary cell or a secondary cell. In some embodiments, the battery comprises a lead acid cell, NiCad cell, NiMH cell, NaNiCl cell, Lithium Ion cell, Nickel Iron cell, Nickel Zinc cell, silver oxide, nickel hydrogen, or lithium polymer cell. In some embodiments, the battery comprises an ampoule battery, a flow battery, or a water activated battery. In some embodiments, the energy providing device is a supercapacitor. In some embodiments, the supercapacitor comprises an electrochemical double-layer capacitor (EDLC), a pseudocapacitor, or a hybrid supercapacitor. In some embodiments, the energy providing device is a fuel cell.

Disclosed herein, in certain embodiments, is a method of preparing a charged compound modified substrate or zwitterion modified substrate comprising: (a) incubating the substrate with a solution comprising a charged or zwitterion compound for at least 40 minutes; and (b) exposing the treated substrate of step a) under a light source for at least one minute, thereby generating the charged compound modified substrate or zwitterion modified substrate. In some embodiments, the incubating of step a) is for at least 45 minutes, at least 50 minutes, at least 55 minutes, at least 60 minutes, at least 65 minutes, at least 70 minutes, at least 80 minutes, at least 90 minutes, or at least 120 minutes. In some embodiments, the incubating of step a) further comprises heating the substrate with the charged or zwitterion compound at a temperature of between 45° C. and 80° C., between 45° C. and 70° C., between 45° C. and 65° C., between 45° C. and 60° C., between 45° C. and 55° C., between 45° C. and 50° C., between 50° C. and 80° C., between 50° C. and 70° C., between 50° C. and 60° C., between 55° C. and 80° C., between 55° C. and 70° C., between 55° C. and 60° C., between 60° C. and 80° C., or between 60° C. and 70° C. In some embodiments, the incubating of step a) further comprises heating the substrate with the charged or zwitterion compound at a temperature of at least 45° C., 50° C., 55° C., 60° C., 65° C., 70° C., 75° C., or 80° C. In some embodiments, the exposing of step b) under a light source is for at least 2 minutes, 3 minutes, 4 minutes, 5 minutes, 6 minutes, 7 minutes, 8 minutes, 9 minutes, 10 minutes, 15 minutes, 20 minutes, 25 minutes, or 30 minutes. In some embodiments, the light source is an ultraviolet light source. In some embodiments, the ultraviolet light source has an intensity of at least 900 μW/cm². In some embodiments, the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm. In some embodiments, the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm, or 280 nm. In some embodiments, the solution of step a) is a first water-alcohol solution. In some embodiments, the first water-alcohol solution comprises a water to alcohol ratio of about 90:10, 80:20, 70:30, 60:40, 50:50, 40:60, 33:67, 30:70, 20:80 or 10:90. In some embodiments, the alcohol comprises methanol, ethanol, 1-propanol, 2-propanol, 2-methyl-2-propanol, 3-methyl-1-butanol, 2,2-dimethyl-1-propanol, cyclopentanol, 1-hexanol, or cyclohexanol. In some embodiments, the charged or zwitterion compound is a compound that has the structure of Formula I:

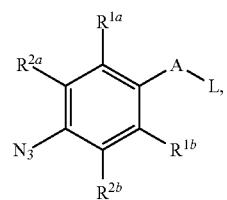

Formula I wherein A is selected from —C(=O)— and —(SO$_2$)—; L is selected from —OQ, —O$^-$, —N$^+$R$^3$HQ and —NR$^3$Q; Q is a structure represented by a formula:

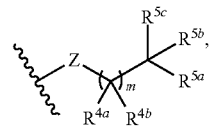

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2$—, and —CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of $R^{12a}$ and $R^{12b}$, when present, is independently selected from hydrogen and C1-C4 alkyl; $R^{13}$, when present, is selected from hydrogen and C1-C4 alkyl, and provided that the compound is charged or zwitterionic. In some embodiments, the compound has a structure selected from:

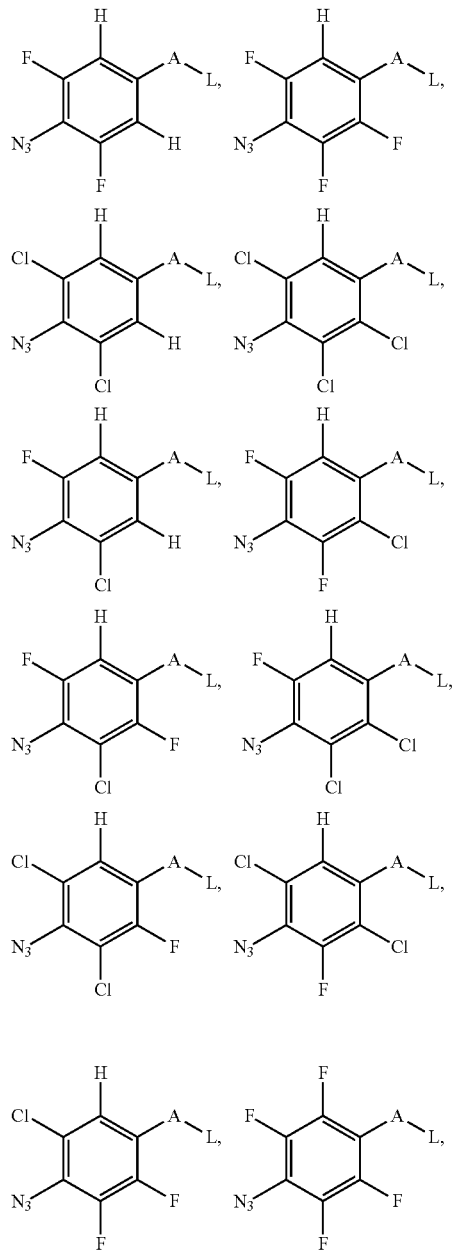

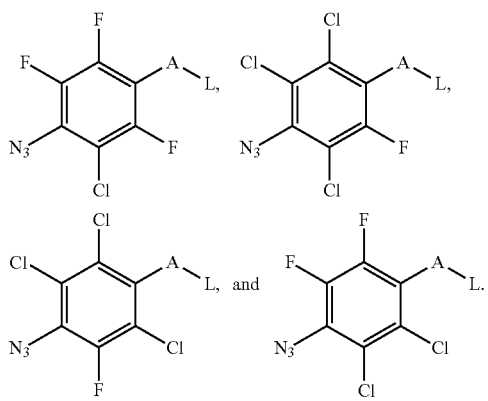

In some embodiments, the compound has a structure selected from:

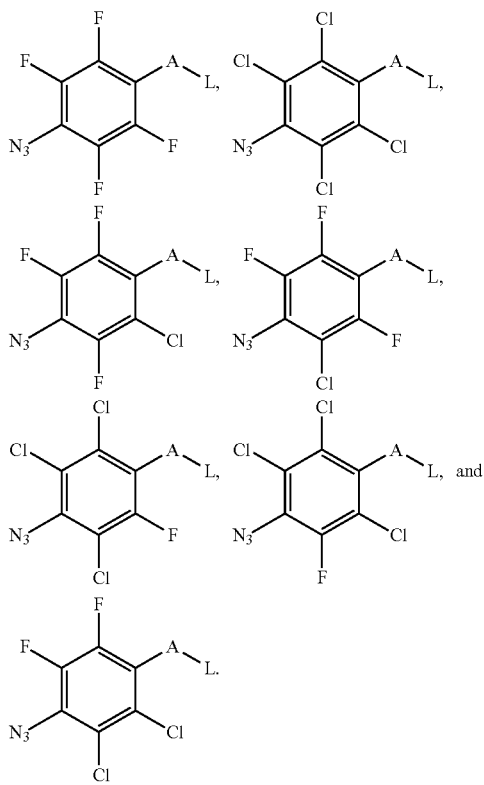

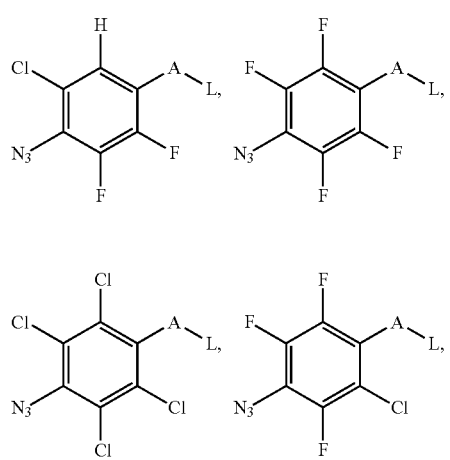

In some embodiments, the compound has the following structure:

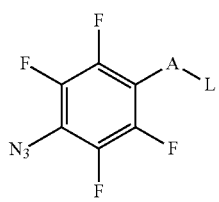

In some embodiments, the compound has the structure selected from:

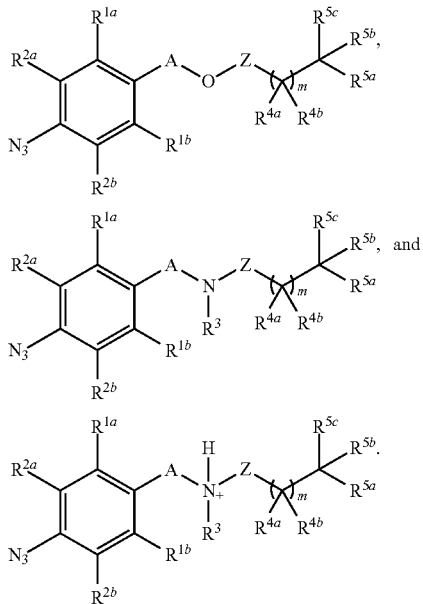

In some embodiments, the compound has the following structure:

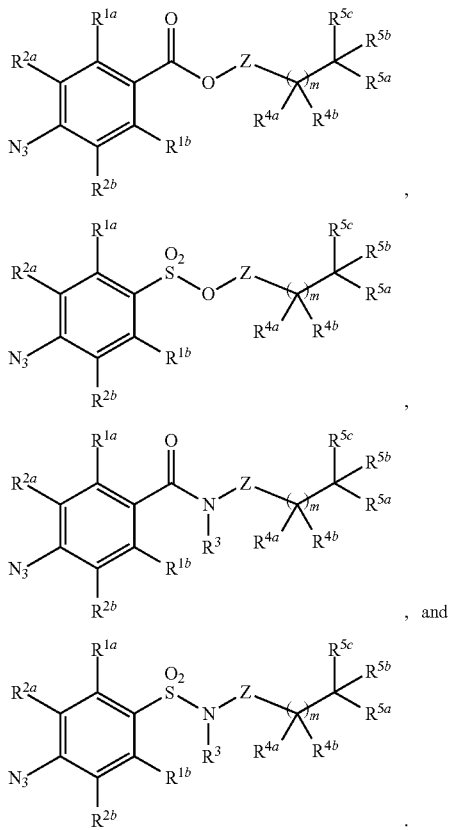

In some embodiments, $R^{1a}$, $R^{1b}$, $R^{2a}$, and $R^{2b}$ are each —F. In some embodiments, Q is selected from:

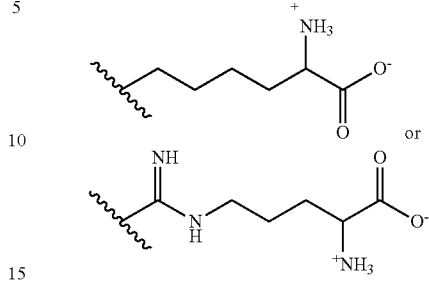

In some embodiments, Q is:

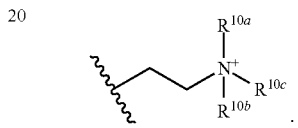

In some embodiments, Q is:

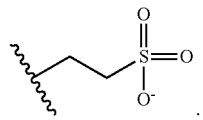 [SMILES: *CCS(=O)(=O)[O-]]

In some embodiments, Z is —$CR^{6a}R^{6b}$—. In some embodiments, $R^{6a}$ and $R^{6b}$ are each hydrogen. In some embodiments, m is 0, 1, 2, or 3. In some embodiments, m is 0. In some embodiments, $R^{5a}$ is —$NR^{10a}R^{10b}R^{10c+}$; $R^{5b}$ is hydrogen; and $R^{5c}$ is hydrogen. In some embodiments, the compound has the structure of Formula Ia:

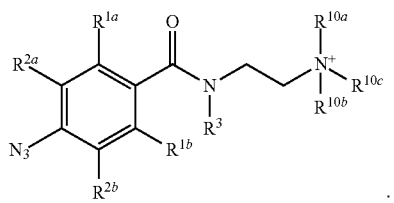

In some embodiments, the compound has the structure of Formula Ib:

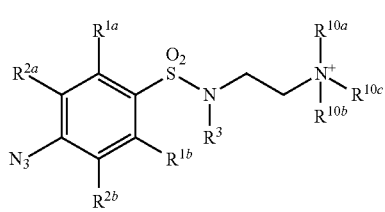

In some embodiments, $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$. In some embodiments, $R^{10a}$ and $R^{10b}$ are each C1-C4alkyl. In some embodiments, $R^{10a}$ and $R^{10b}$ are each methyl. In some embodiments, $R^3$ is hydrogen. In some embodiments, the zwitterionic compound is

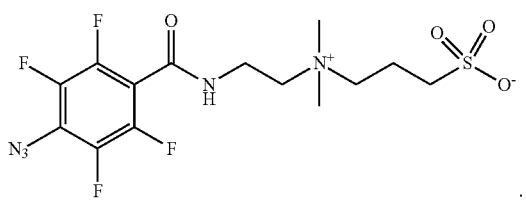 [SMILES: C[N+](C)(CCCS(=O)(=O)[O-])CCNC(=O)c1c(F)c(F)c(N=[N+]=[N-])c(F)c1F]

In some embodiments, the zwitterionic compound is

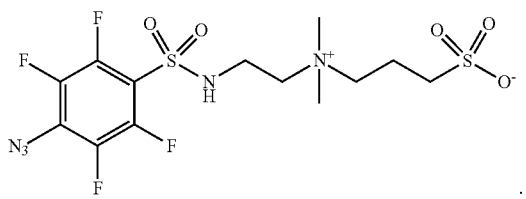 [SMILES: C[N+](C)(CCCS(=O)(=O)[O-])CCNS(=O)(=O)c1c(F)c(F)c(N=[N+]=[N-])c(F)c1F]

In some embodiments, the charged compound is

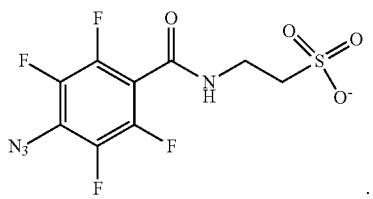 [SMILES: [N-]=[N+]=Nc1c(F)c(F)c(C(=O)NCCS(=O)(=O)[O-])c(F)c1F]

In some embodiments, the charged compound is

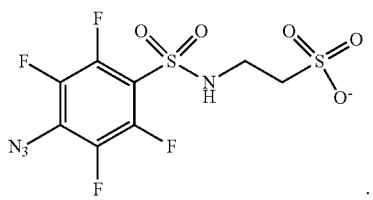

In some embodiments, the charged compound is

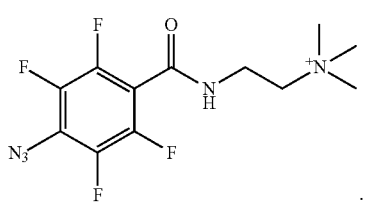 [SMILES: C[N+](C)(C)CCNC(=O)c1c(F)c(F)c(N=[N+]=[N-])c(F)c1F]

In some embodiments, the charged compound is

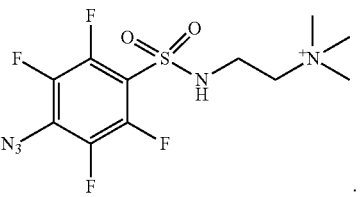 [SMILES: C[N+](C)(C)CCNS(=O)(=O)c1c(F)c(F)c(N=[N+]=[N-])c(F)c1F]

In some embodiments, the charged compound is

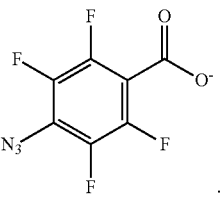 [SMILES: [N-]=[N+]=Nc1c(F)c(F)c(C(=O)[O-])c(F)c1F]

In some embodiments, the charged compound is

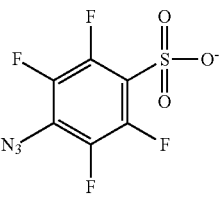

In some embodiments, the concentration of the charged or zwitterion compound in the solution is between 1 mM and 10 mM, between 1 mM and 9 mM, between 1 mM and 8 mM, between 1 mM and 7 mM, between 1 mM and 6 mM, between 1 mM and 5 mM, between 1 mM and 4 mM, between 1 mM and 3 mM, between 1 mM and 2 mM, between 1.5 mM and 10 mM, between 1.5 mM and 9 mM, between 1.5 mM and 8 mM, between 1.5 mM and 7 mM, between 1.5 mM and 6 mM, between 1.5 mM and 5 mM, between 1.5 mM and 4 mM, between 1.5 mM and 3 mM, between 1.5 mM and 2 mM, between 2 mM and 10 mM, between 2 mM and 9 mM, between 2 mM and 8 mM, between 2 mM and 7 mM, between 2 mM and 6 mM, between 2 mM and 5 mM, between 2 mM and 4 mM, between 2 mM and 3 mM, between 3 mM and 10 mM, between 3 mM and 8 mM, between 3 mM and 6 mM, between 4 mM and 10 mM, between 4 mM and 8 mM, between 4 mM and 6 mM, between 5 mM and 10 mM, between 5 mM and 8 mM, between 6 mM and 10 mM, or between 8 mM and 10 mM. In some embodiments, the concentration of the charged or zwitterion compound in the solution is about 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, 5 mM, 6 mM, 7 mM, 8 mM, 9 mM, or 10 mM. In some embodiments, the concentration of the charged or zwitterion compound is between 0.1 to 1 mL per square centimeter of the substrate. In some embodiments, the method further comprises incubating the charged compound modified substrate or zwitterion modified substrate in a second water-alcohol solution after exposure with the light source of step b). In some embodiments, the second water-alcohol solution comprises a water to alcohol ratio of about 90:10, 80:20, 70:30, 60:40, 50:50, 40:60, 33:67, 30:70, 20:80, or 10:90. In some embodiments, the alcohol comprises methanol, ethanol, 1-propanol, 2-propanol, 2-methyl-2-propanol, 3-methyl-1-butanol, 2,2-dimethyl-1-propanol, cyclopentanol, 1-hexanol or cyclohexanol. In some embodiments, the incubating further comprises sonicating the charged compound modified substrate or zwitterion modified substrate in the second water-alcohol solution. In some embodiments, the sonication is for at least 1 minutes, 2 minutes, 3 minutes, 4 minutes, 5 minutes, 6 minutes, 7 minutes, 8 minutes, 9 minutes, 10 minutes, 15 minutes, 20 minutes, 25 minutes, or 30 minutes. In some embodiments, the method further comprises drying the charged compound modified substrate or zwitterion modified substrate under vacuum after incubation in the second water-alcohol solution. In some embodiments, the zwitterionic compound is

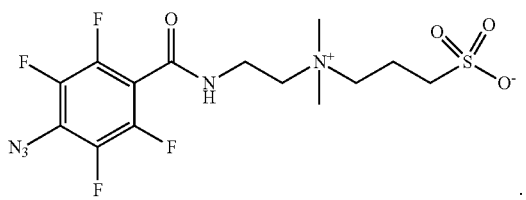 [SMILES: C[N+](C)(CCCS(=O)(=O)[O-])CCNC(=O)c1c(F)c(F)c(N=[N+]=[N-])c(F)c1F]

In some embodiments, the zwitterionic compound is

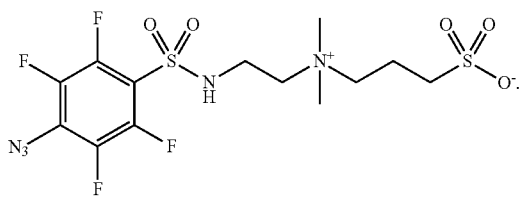

In some embodiments, the charged compound is

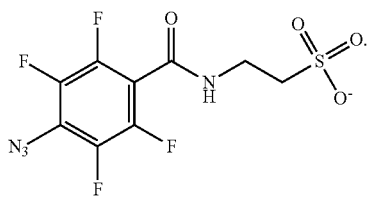

In some embodiments, the charged compound is

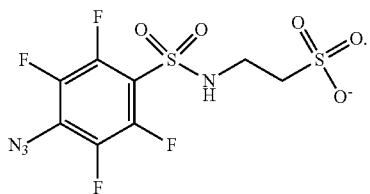 [SMILES: [N-]=[N+]=Nc1c(F)c(F)c(S(=O)(=O)NCCS(=O)(=O)[O-])c(F)c1F]

In some embodiments, the charged compound is

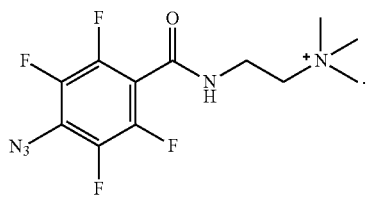

In some embodiments, the charged compound is

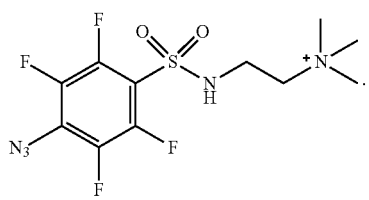 [SMILES: C[N+](C)(C)CCNS(=O)(=O)c1c(F)c(F)c(N=[N+]=[N-])c(F)c1F]

In some embodiments, the charged compound is

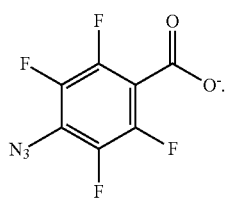

In some embodiments, the charged compound is

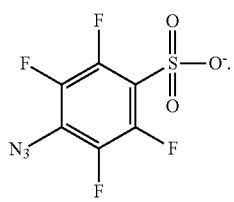

In some embodiments, the separator comprises a polymer-based separator. In some embodiments, the polymer-based separator comprises a polyolefinic separator. In some embodiments, the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some embodiments, the separator comprises a microporous separator, a nonwoven separator, an ion-exchange membrane, a supported liquid membrane, or a solid ion conductor. In some embodiments, the substrate comprises a carbon-based substrate containing a moiety capable of binding with the perfluorophenylazide charged or zwitterion derivative of Formula I. In some embodiments, the carbon-based substrate comprises a polymer moiety. In some embodiments, the carbon-based substrate comprises a polyolefin moiety. In some embodiments, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

Disclosed herein, in certain embodiments, is a compound that has the structure of Formula IIa:

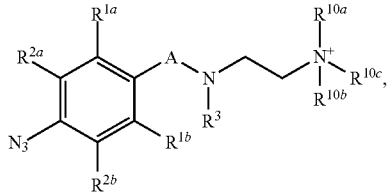

Formula IIa wherein A is selected from —C(=O)— and —(SO$_2$)—; each of $R^{1a}$ and $R^{1b}$ is independently selected from hydrogen and halogen; each of $R^{2a}$ and $R^{2b}$ is halogen; $R^3$ is selected from hydrogen and C1-C4 alkyl; $R^{10a}$ and $R^{10b}$ are independently selected from C1-C4 alkyl; and $R^{10c}$ is selected from —(C1-C8alkylene)SO$_3^-$, —(C1-C8alkylene)SO$_3$H, —(C1-C8alkylene)CO$_2^-$, and —(C1-C8alkylene)CO$_2$H. In some embodiments, A is —(SO$_2$)—. In some embodiments, A is —(C=O)—. In some embodiments, $R^{1a}$, $R^{1b}$, $R^{2a}$, and $R^{2b}$ are each independently selected from —Cl or —F. In some embodiments, $R^{1a}$, $R^{1b}$, $R^{2a}$, and $R^{2b}$ are each —F. In some embodiments, $R^3$ is hydrogen. In some embodiments, $R^{10a}$ and $R^{10b}$ are each methyl. In some embodiments, $R^{10c}$ is —CH$_2$CH$_2$CH$_2$—SO$_3^-$, —CH$_2$CH$_2$CH$_2$—SO$_3$H, —CH$_2$CH$_2$CH$_2$—CO$_2^-$, or —CH$_2$CH$_2$CH$_2$—CO$_2$H. In some embodiments, $R^{10c}$ is —CH$_2$CH$_2$CH$_2$—SO$_3^-$ or —CH$_2$CH$_2$CH$_2$—CO$_2^-$. In some embodiments, the zwitterionic compound is

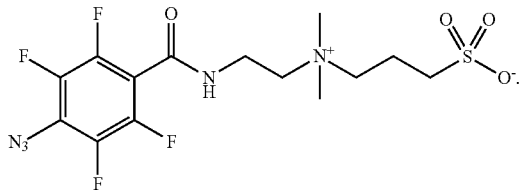

In some embodiments, the zwitterionic compound is

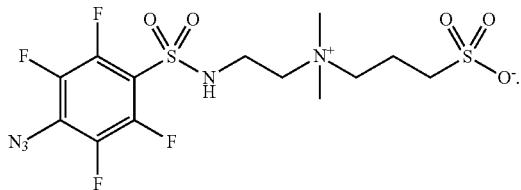

In some embodiments, the charged compound is

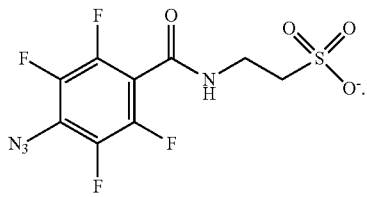

In some embodiments, the charged compound is

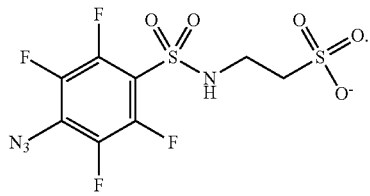

In some embodiments, the charged compound is

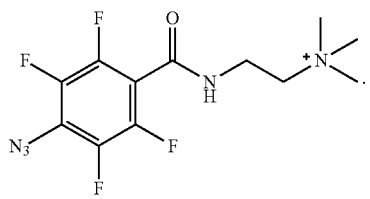

In some embodiments, the charged compound is

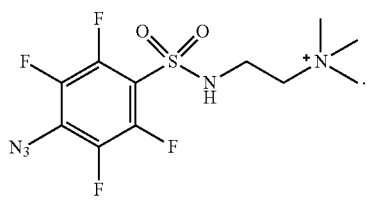 [SMILES: C[N+](C)(C)CCNS(=O)(=O)c1c(F)c(F)c(N=[N+]=[N-])c(F)c1F]

In some embodiments, the charged compound is

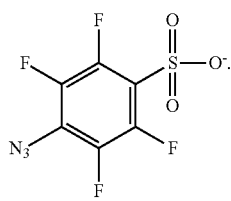

In some embodiments, the charged compound is

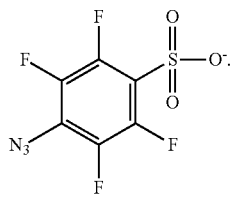

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
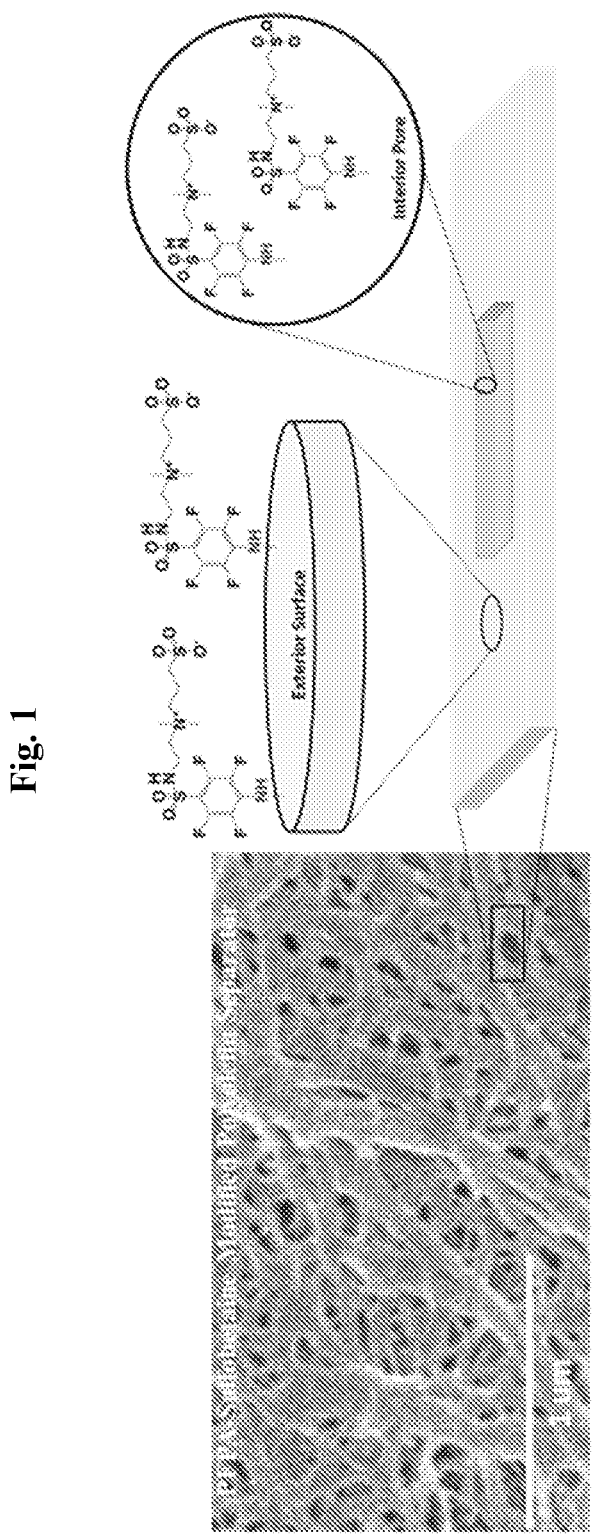
FIG. 1 shows an SEM image of a PFPA-sulfobetaine modified polyolefin separator (left) and a schematic representation of PFPA-sulfobetaine molecules grafted onto the exterior and interior surfaces of a polyolefin separator (right).

A separator, in an energy providing device, is used to electrically insulate and physically separate the anode and cathode to enable free ionic transport and isolating electronic flow. In some cases, a suitable separator for use in an energy providing device is thin and flexible and is mechanically and chemically robust, enabling the separator to perform with nominal change over the lifetime of the device. In additional cases, a suitable separator for use in an energy providing device possesses a large surface area and tolerates high temperatures to minimize overheating and reduce the chance of "thermal runaway".

In some cases, polymer-based separators, are used to separate the anode and cathode. Due to their robust mechanical properties, chemical stability in highly oxidative conditions, and low cost, polyolefin separators composed of polyethylene (PE) and/or polypropylene (PP) have emerged as the separators of choice in commercial lithium-ion batteries (LiBs). Additionally, PE separators possess an inherent safety feature that prevents thermal runaway by acting as a fuse inside the cells. As a defective battery heats up from an electrical short, the porous separator melts into a dense film that breaks the circuit, preventing further electrochemical reactions within the battery. As several accounts of LiB fires and explosions have come into the public spotlight, safety has perhaps become one of the most critical requirements when selecting a separator for commercial LiBs. This has led to an increased use of trilayer separators composed of a PE layer sandwiched between two PP membranes. This trilayer separator combines the chemical and thermal stability of PP with the thermal shutdown property of PE.

Despite their desirable properties, non-polar polyolefin separators are incompatible with the polar cyclic carbonate electrolytes, ethylene carbonate (EC) and propylene carbonate (PC), used in LiBs, due to insufficient wetting of the separators. Absorption of the electrolytic solution into the separator is essential for ion transport and low internal resistance of the overall battery. The poor chemical compatibility with these mixtures inhibits complete wetting of the liquid electrolyte into the separator directly affecting the overall power performance, cycling stability, and longevity of the battery.

In some instances, different techniques such as plasma, electron beams, gamma rays, UV light and grafting or coating are used to modify a separator to increase electrolyte uptake and/or greater performance. However, in some instances, the ability to scale these techniques to an industrial scale has been costly. In nearly every commercial application, it is necessary to produce several hundred meters of modified separator at low cost. Techniques have been demonstrated on monolayer membranes composed of either polyethylene (PE) or polypropylene (PP), but little is known on modifications of trilayer polyolefin separators. A trilayer separator can be superior in that it combines the chemical and thermal stability of PP with the thermal shutdown property of PE. However, trilayer separators are thicker and thus require longer periods to absorb electrolytes, which increases the costs.

PFPA photochemistry is a method designed to covalently attach molecules to the surface of polymeric materials while maintaining the material's intrinsic bulk properties. PFPA molecules contain an azide functional group which, when activated by photoexcitation, produce a highly reactive singlet nitrene that can undergo C—H insertion within the hydrocarbon backbone of the polyolefins, thus creating a covalent bond between the polymer and PFPA molecule.

Assembly time is constrained by the time necessary for the electrolyte to fully absorb into the separator. As commercial demand of LiB continues to rise, work to improve separator compatibility with organic electrolytes has gained both interest and importance.

Disclosed herein is an energy providing device that comprises a modified separator (e.g., a charged compound modified substrate or zwitterion-modified substrate that comprises a separator). In some instances, the modified separator improves charge acceptance, improves rechargeability, reduces water loss, improves charge/discharge cycling efficiency, and/or extends life of the energy providing device, relative to device with an un-modified separator. In some cases, the modified separator comprises a charged or zwitterion compound. In some cases, the modified separator comprises a charged or zwitterion compound having a structure of Formula I disclosed herein.

In some embodiments, also disclosed herein is an energy providing device that comprises an electrolyte comprising an perhalogenatedphenyl azide charged or zwitterion compound. In additional cases, provided herein are methods of preparing a charged compound modified substrate or zwitterion modified substrate for use in an energy providing device and compositions for use in an energy providing device. In some embodiments, the methods are carried out in three steps. In some embodiments, the methods involve no protection/de-protection chemistry. In some embodiments, the methods are accomplished under ambient conditions with common commercially available reagents enabling the synthesis of the desired product at low cost.

Charged and Zwitterion Compounds for Substrate Modification

In some embodiments, disclosed herein is a charged compound modified substrate or zwitterion modified substrate comprising a compound having a structure of Formula I:

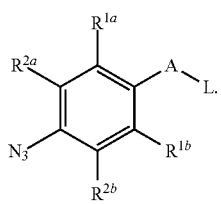

Formula I wherein A is selected from —C(=O)— and —(SO$_2$)—; L is selected from —OQ, —O$^-$, —N$^+$R$^3$HQ and —NR$^3$Q; Q is a structure represented by a formula:

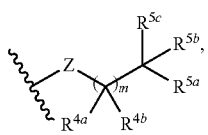

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl; R$^{13}$, when present, is selected from hydrogen and C1-C4 alkyl, and provided that the compound is charged or zwitterionic.

It is understood that the disclosed compositions, mixtures, and membranes can be employed in connection with the disclosed methods and uses.

A. Compounds

In some instances, a compound comprises an azide functionality. In another aspect, the compound comprises a perfluorophenyl azide functionality. Without wishing to be bound by theory, perfluorophenyl azides can react with a variety of substrates upon exposure to irradiation. In some embodiments, the substrate is a polymer separator, such as a polyethylene or polypropylene membrane separator.

B. Structure

In some embodiments, disclosed herein is a charged or zwitterionic compound having a structure represented by a formula I:

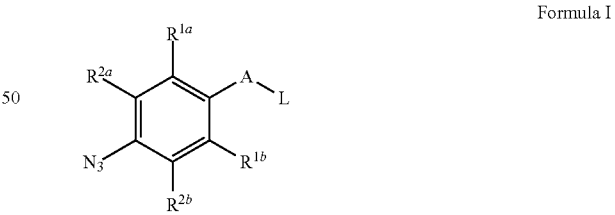

Formula I wherein A is selected from —C(=O)— and —(SO$_2$)—; L is selected from —OQ, —O$^-$, —N$^+$R$^3$HQ and —NR$^3$Q; Q is a structure represented by a formula:

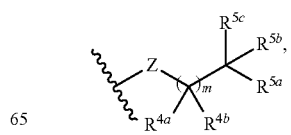

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl; R$^{13}$, when present, is selected from hydrogen and C1-C4 alkyl, and provided that the compound is charged or zwitterionic.

In some embodiments, a compound has a structure selected from:

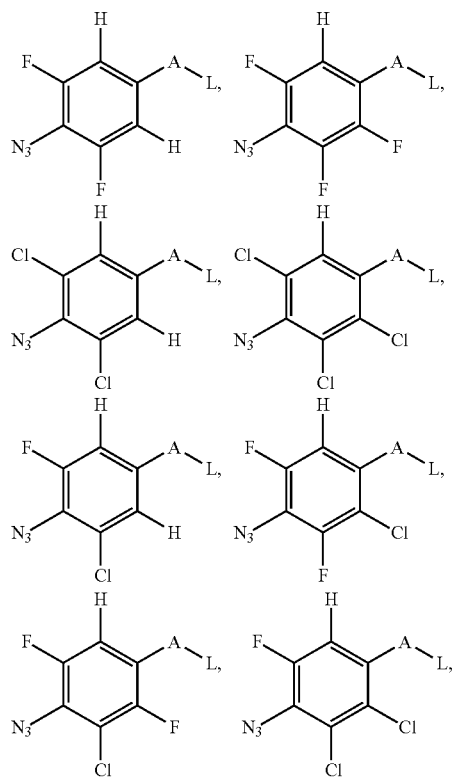

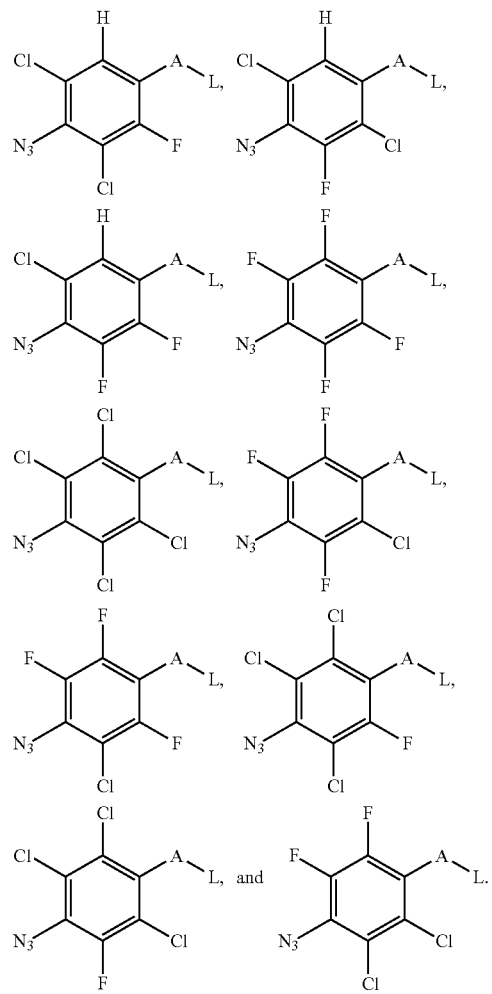

In some embodiments, a compound has a structure selected from:

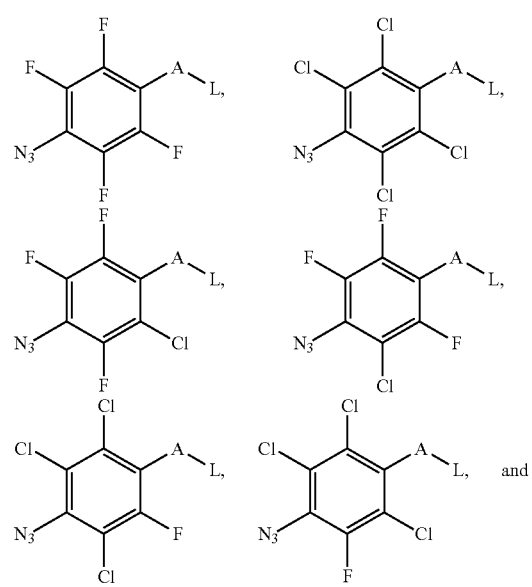

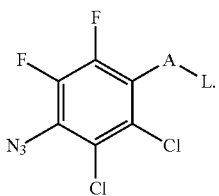
In some embodiments, the compound has the following structure:
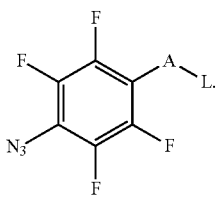
In some embodiments, the compound has a structure selected from:
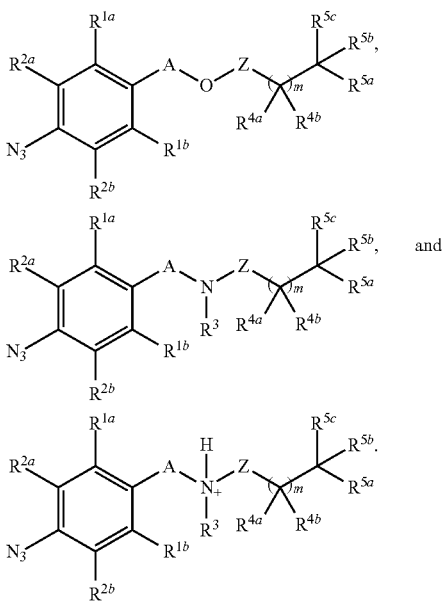
In some embodiments, the compound has a structure selected from:
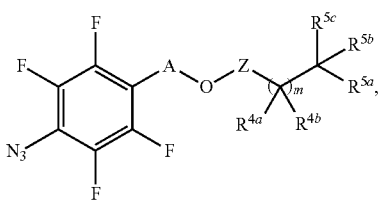
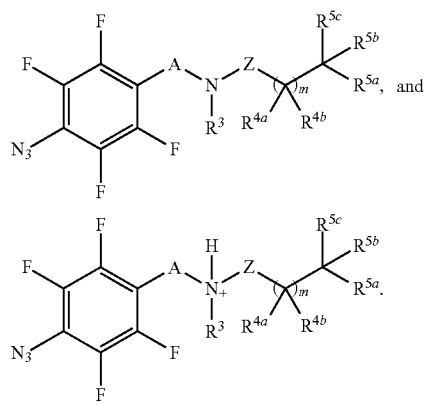
In some embodiments, the compound has a structure selected from:
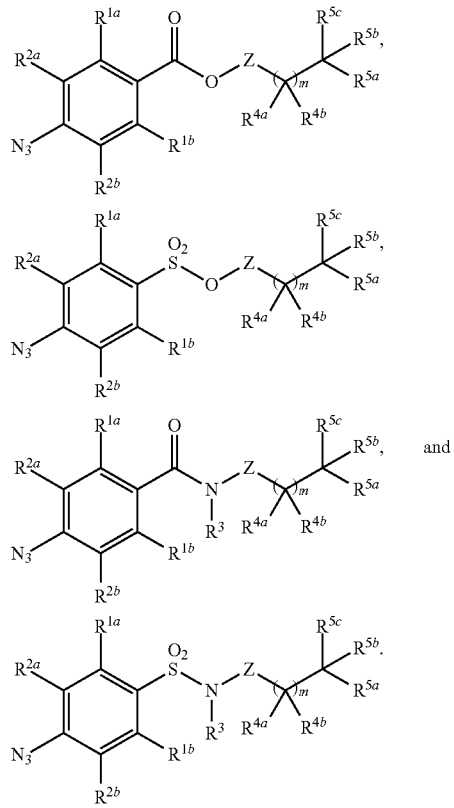
In some embodiments, the compound has a structure selected from:
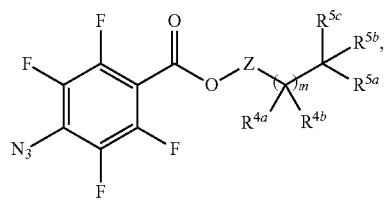

-continued

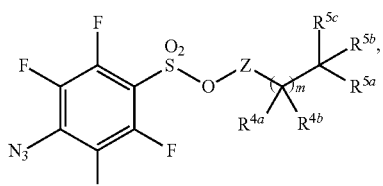

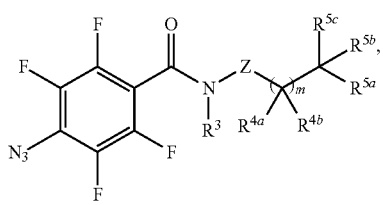

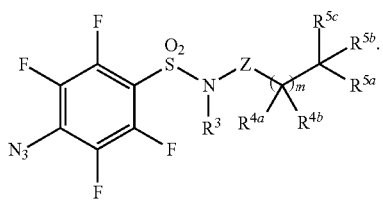

In some embodiments, Q is selected from: Q is selected from:

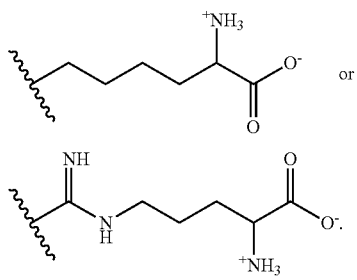

In some embodiments, Q is

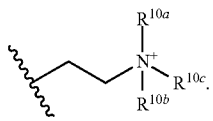

In some embodiments, Q is:

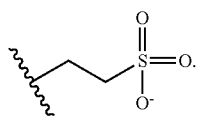 [SMILES: *CCS(=O)(=O)[O-]]

In some embodiments, $R^{1a}$, $R^{1b}$, $R^{2a}$, and $R^{2b}$ are each —F. In some embodiments, Z is —$CR^{6a}R^{6b}$—. In some embodiments, $R^{6a}$ and $R^{6b}$ are each hydrogen. In some embodiments, m is 0, 1, 2, or 3. In some embodiments, m is 0. In some embodiments, $R^{5a}$ is —$NR^{10a}R^{10b}R^{10c+}$; $R^{5b}$ is hydrogen; and $R^{5c}$ is hydrogen.

In some embodiments, the compound has the structure of Formula Ia:

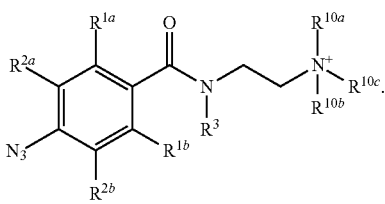

In some embodiments, the compound has the structure of Formula Ib:

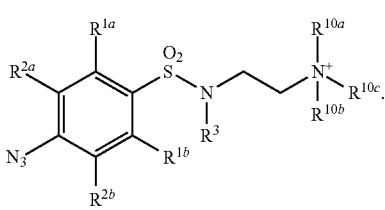

In some embodiments, $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, $R^{10c}$ is —(C1-C8alkylene)$SO_3^-$. In some embodiments, $R^{10C}$ is —(C1-C8alkylene)$SO_3H$, —(C1-C8alkylene)$CO_2^-$. In some embodiments, $R^{10C}$ is —(C1-C8alkylene)$CO_2H$. In some embodiments, $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$. In some embodiments, $R^{10a}$ and $R^{10b}$ are each C1-C4alkyl. In some embodiments, $R^{10a}$ and $R^{10b}$ are each methyl. In some embodiments, $R^3$ is hydrogen.

In some embodiments, the zwitterionic compound is:

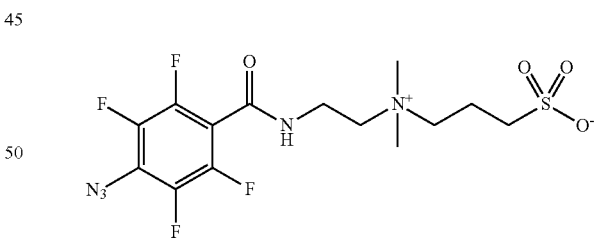

In some embodiments, the zwitterionic compound is:

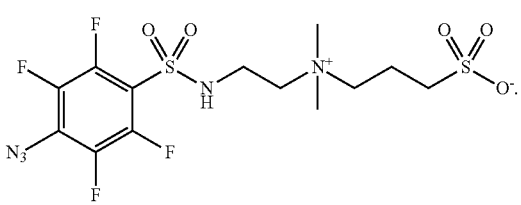

In some embodiments, the charged compound is:

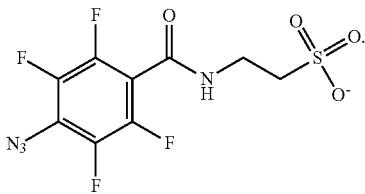 [SMILES: [N-]=[N+]=Nc1c(F)c(F)c(C(=O)NCCS(=O)(=O)[O-])c(F)c1F]

In some embodiments, the charged compound is:

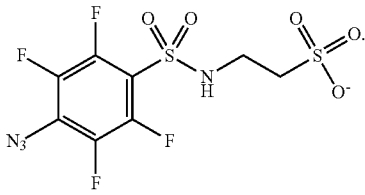 [SMILES: [N-]=[N+]=Nc1c(F)c(F)c(S(=O)(=O)NCCS(=O)(=O)[O-])c(F)c1F]

In some embodiments, the charged compound is:

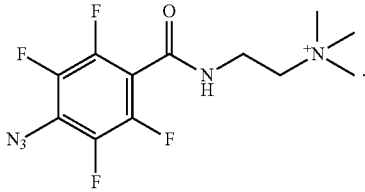

In some embodiments, the charged compound is:

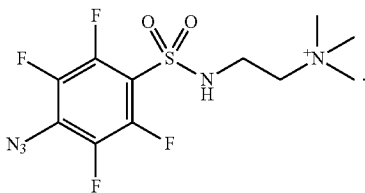 [SMILES: C[N+](C)(C)CCNS(=O)(=O)c1c(F)c(F)c(N=[N+]=[N-])c(F)c1F]

In some embodiments, the charged compound is:

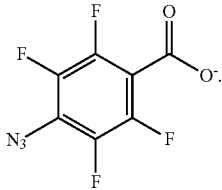

In some embodiments, the charged compound is:

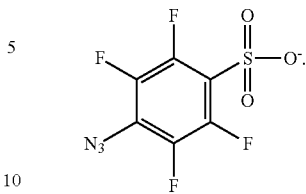

In some embodiments, disclosed herein is perhalogenatedphenyl azide charged or zwitterion compound, wherein the perhalogenatedphenyl azide charged or zwitterion compound has the structure of Formula I:

Formula I

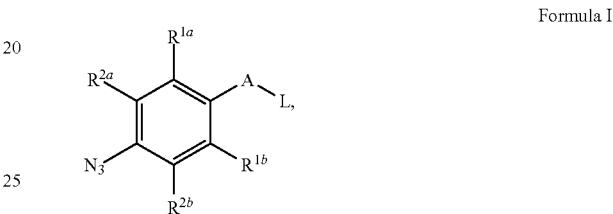

wherein A is selected from —C(=O)— and —(SO$_2$)—; L is selected from —OQ, —O$^-$, —N$^+$R$^3$HQ and —NR$^3$Q; Q is a structure represented by a formula:

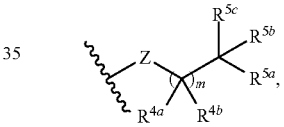

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl;

$R^{13}$, when present, is selected from hydrogen and C1-C4 alkyl, and provided that the compound is charged or zwitterionic.

In some embodiments, the compound has a structure selected from:

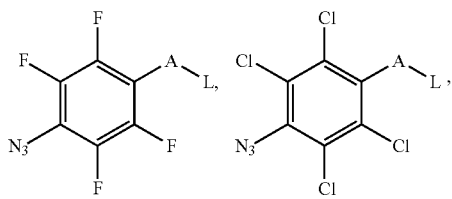

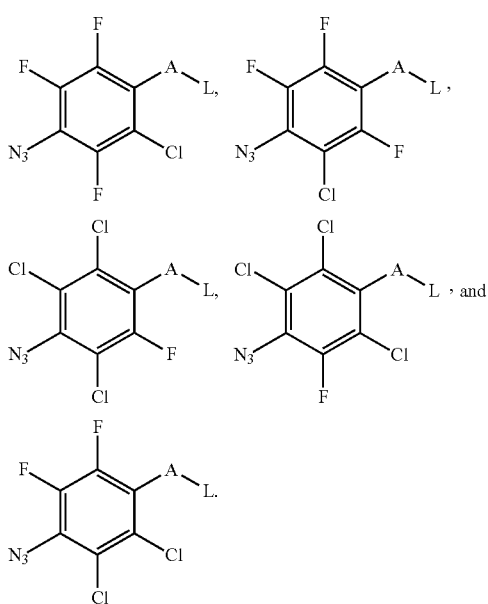

In some embodiments, the compound has the following structure:

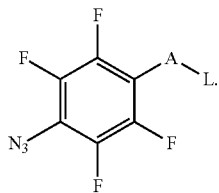

In some embodiments, the compound has the structure selected from:

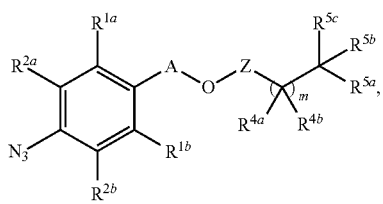

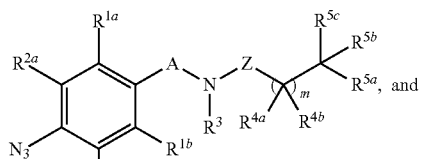

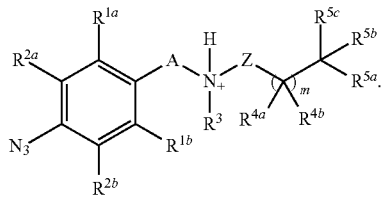

In some embodiments, the compound has the following structure:

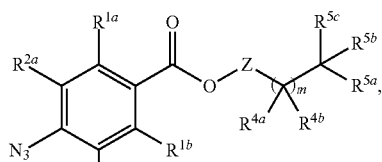

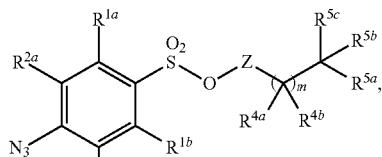

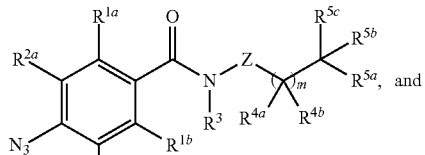

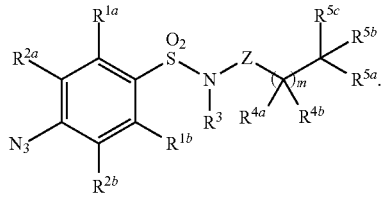

In some embodiments, $R^{1a}$, $R^{1b}$, $R^{2a}$, and $R^{2b}$ are each —F.

In some embodiments, Q is selected from:

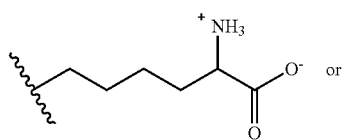

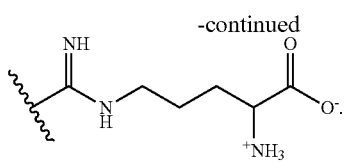

In some embodiments, Q is:

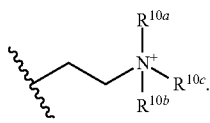

In some embodiments, Q is:

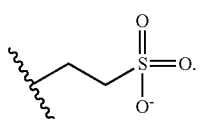 [SMILES: *CCS(=O)(=O)[O-]]

In some embodiments, Z is —$CR^{6a}R^{6b}$—. In some embodiments, $R^{6a}$ and $R^{6b}$ are each hydrogen. In some embodiments, m is 0, 1, 2, or 3. In some embodiments, m is 0. In some embodiments, $R^{5a}$ is —$NR^{10a}R^{10b}R^{10c+}$; $R^{5b}$ is hydrogen; and $R^{5c}$ is hydrogen.

In some embodiments, the compound has the structure of Formula Ia:

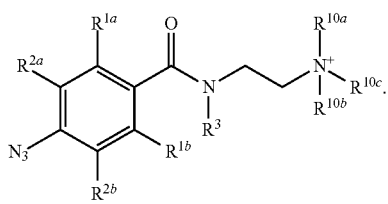

In some embodiments, the compound has the structure of Formula Ib:

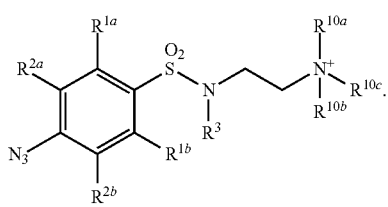

In some embodiments, $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, $R^{10c}$ is —(C1-C8alkylene)$SO_3^-$. In some embodiments, $R^{10c}$ is —(C1-C8alkylene)$SO_3H$, —(C1-C8alkylene)$CO_2^-$. In some embodiments, $R^{10c}$ is —(C1-C8alkylene)$CO_2H$. In some embodiments, $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$. In some embodiments, $R^{10a}$ and $R^{10b}$ are each C1-C4alkyl. In some embodiments, $R^{10a}$ and $R^{10b}$ are each methyl. In some embodiments, $R^3$ is hydrogen.

In some embodiments, the zwitterionic compound is:

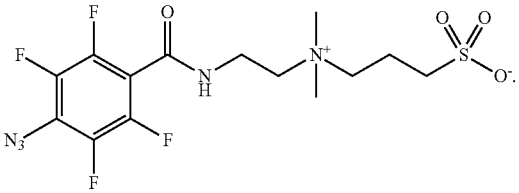

In some embodiments, the zwitterionic compound is:

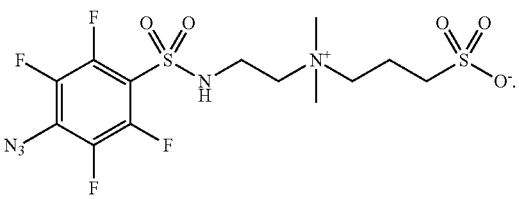

In some embodiments, the charged compound is:

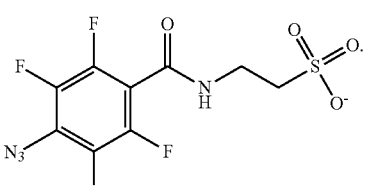

In some embodiments, the charged compound is:

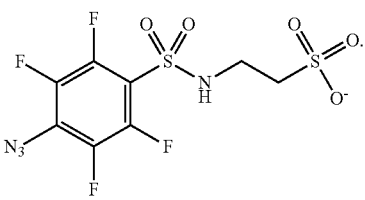 [SMILES: [N-]=[N+]=Nc1c(F)c(F)c(S(=O)(=O)NCCS(=O)(=O)[O-])c(F)c1F]

In some embodiments, the charged compound is:

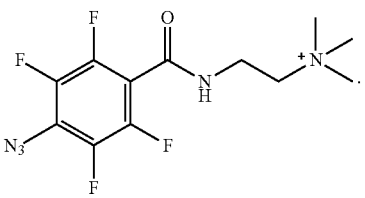

In some embodiments, the charged compound is:

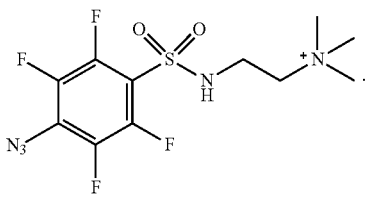 [SMILES: C[N+](C)(C)CCNS(=O)(=O)c1c(F)c(F)c(N=[N+]=[N-])c(F)c1F]

In some embodiments, the charged compound is:

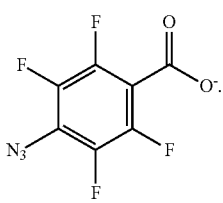

In some embodiments, the charged compound is:

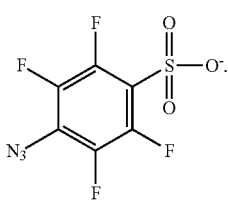

In some embodiments, disclosed herein is a charged or zwitterionic compound that has the structure of Formula IIa:

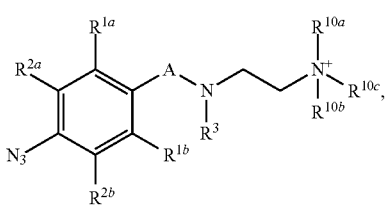

Formula IIa wherein A is selected from —C(=O)— and —(SO$_2$)—; each of $R^{1a}$ and $R^{1b}$ is independently selected from hydrogen and halogen; each of $R^{2a}$ and $R^{2b}$ is halogen; $R^3$ is selected from hydrogen and C1-C4 alkyl; $R^{10a}$ and $R^{10b}$ are independently selected from C1-C4 alkyl; and $R^{10c}$ is selected from —(C1-C8alkylene)SO$_3^-$, —(C1-C8alkylene)SO$_3$H, —(C1-C8alkylene)CO$_2^-$, and —(C1-C8alkylene)CO$_2$H.

In some embodiments, A is —(SO$_2$)—. In some embodiments, A is —C(=O)—. In some embodiments, $R^{1a}$, $R^{1b}$, $R^{2a}$, and $R^{2b}$ are each independently selected from —Cl or —F. In some embodiments, $R^{1a}$, $R^{1b}$, $R^{2a}$, and $R^{2b}$ are each —F. In some embodiments, $R^3$ is hydrogen. In some embodiments, $R^3$ is C1-C4 alkyl. In some embodiments, $R^{10a}$ and $R^{10b}$ are each methyl. In some embodiments, $R^{10c}$ is —CH$_2$CH$_2$CH$_2$—SO$_3^-$, —CH$_2$CH$_2$CH$_2$—SO$_3$H, —CH$_2$CH$_2$CH$_2$—CO$_2^-$, or —CH$_2$CH$_2$CH$_2$—CO$_2$H. In some embodiments, $R^{10c}$ is —CH$_2$CH$_2$CH$_2$—SO$_3^-$ or —CH$_2$CH$_2$CH$_2$—CO$_2^-$.

In some embodiments, the zwitterionic compound is:

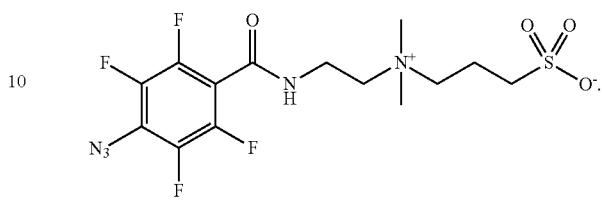

In some embodiments, the zwitterionic compound is:

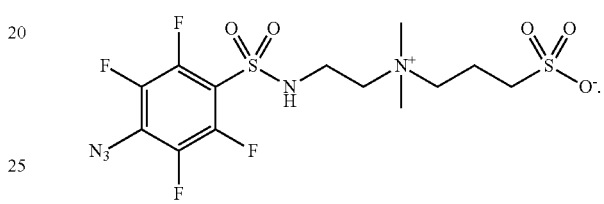

In some embodiments, disclosed herein is a charged compound that has the structure of Formula IIa:

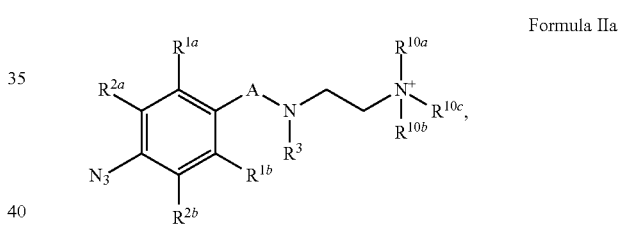

Formula IIa wherein A is selected from —C(=O)— and —(SO$_2$)—; each of $R^{1a}$ and $R^{1b}$ is independently selected from hydrogen and halogen; each of $R^{2a}$ and $R^{2b}$ is halogen; $R^3$ is selected from hydrogen and C1-C4 alkyl; and $R^{10a}$, $R^{10b}$, and $R^{10c}$ are independently selected from C1-C4 alkyl.

In some embodiments, A is —(SO$_2$)—. In some embodiments, A is —C(=O)—. In some embodiments, $R^{1a}$, $R^{1b}$, $R^{2a}$, and $R^{2b}$ are each independently selected from —Cl or —F. In some embodiments, $R^{1a}$, $R^{1b}$, $R^{2a}$, and $R^{2b}$ are each —F. In some embodiments, $R^3$ is hydrogen. In some embodiments, $R^{10a}$, $R^{10b}$ and $R^{10c}$ are each methyl.

In some embodiments, charged compound is:

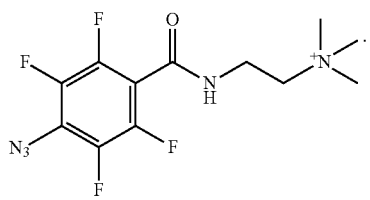 [SMILES: C[N+](C)(C)CCNC(=O)c1c(F)c(F)c(N=[N+]=[N-])c(F)c1F]

In some embodiments, the charged compound is:

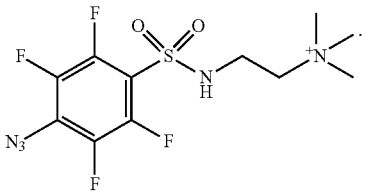 [SMILES: C[N+](C)(C)CCNS(=O)(=O)c1c(F)c(F)c(N=[N+]=[N-])c(F)c1F]

In some embodiments, disclosed herein is a charged compound that has the structure of Formula IIb:

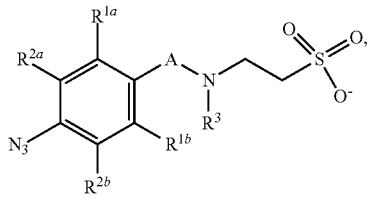

Formula IIb wherein A is selected from —C(=O)— and —(SO$_2$)—; each of R$^{1a}$ and R$^{1b}$ is independently selected from hydrogen and halogen; each of R$^{2a}$ and R$^{2b}$ is halogen; and R$^3$ is selected from hydrogen and C1-C4 alkyl.

In some embodiments, A is —(SO$_2$)—. In some embodiments, A is —(C=O)—. In some embodiments, R$^{1a}$, R$^{1b}$, R$^{2a}$, and R$^{2b}$ are each independently selected from —Cl or —F. In some embodiments, R$^{1a}$, R$^{1b}$, R$^{2a}$, and R$^{2b}$ are each —F. In some embodiments, R$^3$ is hydrogen.

In some embodiments, the charged compound is:

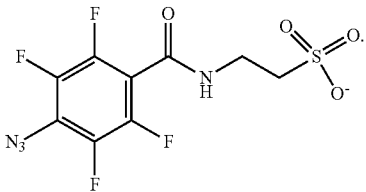 [SMILES: [N-]=[N+]=Nc1c(F)c(F)c(C(=O)NCCS(=O)(=O)[O-])c(F)c1F]

In some embodiments, the charged compound is:

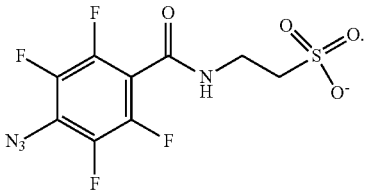 [SMILES: [N-]=[N+]=Nc1c(F)c(F)c(C(=O)NCCS(=O)(=O)[O-])c(F)c1F]

In one aspect, m is an integer selected from 0, 1, 2, 3, 4, 5, 6, 7, and 8. In a further aspect, m is an integer selected from 0, 1, 2, 3, 4, 5, 6, and 7. In a still further aspect, m is an integer selected from 0, 1, 2, 3, 4, 5, and 6. In yet a further aspect, m is an integer selected from 0, 1, 2, 3, 4, and 5. In an even further aspect, m is an integer selected from 0, 1, 2, 3, and 4. In a still further aspect, m is an integer selected from 0, 1, 2, and 3. In yet a further aspect, m is an integer selected from 0, 1, and 2. In an even further aspect, m is an integer selected from 0 and 1. In a still further aspect, m is 0. In yet a further aspect, m is 1. In an even further aspect, m is 2. In a still further aspect, m is 3. In yet a further aspect, m is 4. In an even further aspect, m is 5. In a still further aspect, m is 6. In yet a further aspect, m is 6. In an even further aspect, m is 7. In a still further aspect, m is 8.

a. A and L Groups

In one aspect, A is selected from —C(=O)— and —(SO$_2$)—. In a further aspect, A is —C(=O)—. In a still further aspect, A is —(SO$_2$)—.

In one aspect, L is selected from —OQ, —O$^-$, —N+R$^3$HQ and —NR$^3$Q. In a still further aspect, L is —OQ. In a still further aspect, L is —N+R$^3$HQ. In a still further aspect, L is —NR$^3$Q.

In a still further aspect, A is —C(=O)— and L is —OQ. In a still further aspect, A is —C(=O)— and L is —N+R$^3$HQ. In a still further aspect, A is —C(=O)— and L is —NR$^3$Q. In a still further aspect, A is —(SO$_2$)— and L is —OQ. In a still further aspect, A is —(SO$_2$)— and L is —N+R$^3$HQ. In a still further aspect, A is —(SO$_2$)— and L is —NR$^3$Q.

c. Z Groups

In a further aspect, Z is selected from —CR$^{6a}$R$^{6b}$—, —C(=O)—, —C(=NH)—, and —C(=NH)NR$^7$—. In a still further aspect, Z is —CR$^{6a}$R$^{6b}$—. In a still further aspect, Z is —C(=O)—. In a still further aspect, Z is —C(=NH)—. In a still further aspect, Z is —C(=NH)NR$^7$—.

d. R$^{1a}$ and R$^{1b}$ Groups

In one aspect, each of R$^{1a}$ and R$^{1b}$ is independently selected from hydrogen and halogen. In a further aspect, each of R$^{1a}$ and R$^{1b}$ is hydrogen.

In a further aspect, each of R$^{1a}$ and R$^{1b}$ is halogen. In a still further aspect, each of R$^{1a}$ and R$^{1b}$ is independently selected from —Cl and —F. In yet a further aspect, each of R$^{1a}$ and R$^{1b}$ is —Cl. In an even further aspect, each of R$^{1a}$ and R$^{1b}$ is —F. In a still further aspect, R$^{1a}$ is —Cl and R$^{1b}$ is —F.

In a further aspect, R$^{1b}$ is hydrogen and R$^{1a}$ is halogen. In a still further aspect, R$^{1b}$ is hydrogen and R$^{1a}$ is selected from —Cl and —F. In yet a further aspect, R$^{1b}$ is hydrogen and R$^{1a}$ is —Cl. In an even further aspect, R$^{1b}$ is hydrogen and R$^{1a}$ is —F.

e. R$^{2a}$ and R$^{2b}$ Groups

In one aspect, each of R$^{2a}$ and R$^{2b}$ is halogen. In a further aspect, each of R$^{2a}$ and R$^{2b}$ is independently selected from —Cl and —F. In a still further aspect, each of R$^{2a}$ and R$^{2b}$ is —Cl. In yet a further aspect, each of R$^{2a}$ and R$^{2b}$ is —F. In an even further aspect, R$^{2a}$ is —Cl and R$^{2b}$ is —F.

f. R$^3$ Groups

In one aspect, R$^3$, when present, is selected from hydrogen and C1-C4 alkyl. In a further aspect, R$^3$, when present, is selected from hydrogen, methyl, ethyl, and propyl. In a still further aspect, R$^3$, when present, is selected from hydrogen, methyl, and ethyl. In yet a further aspect, R$^3$, when present, is selected from hydrogen and methyl. In an even further aspect, R$^3$, when present, is hydrogen.

g. R$^{4a}$ and R$^{4b}$ Groups

In one aspect, each of R$^{4a}$ and R$^{4b}$, when present, is independently selected from hydrogen, halogen, —CN, —OH, —NR$^{8a}$R$^{8b}$, —NR$^{8a}$R$^{8b}$H+, C1-C4 alkyl, C1-C4 monohaloalkyl, C1-C4 polyhaloalkyl, —SO$_3^-$, —SO$_3$R$^9$, —CO$_2^-$, and —CO$_2$R$^9$. In a further aspect, each of R$^{4a}$ and R$^{4b}$, when present, is independently selected from hydrogen, —F, —Cl, —CN, —OH, —NR$^{8a}$R$^{8b}$, —NR$^{8a}$R$^{8b}$H+, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —F, —Cl, —CN, —OH, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from hydrogen, —F, —Cl, —CN, —OH, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from hydrogen, —F, —Cl, —CN, —OH, —NH$_2$, —NH$_3^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from halogen, —CN, —OH, —NR$^{8a}$R$^{8b}$, —NR$^{8a}$R$^{8b}$H+, C1-C4 alkyl, C1-C4 monohaloalkyl, C1-C4 polyhaloalkyl, —SO$_3^-$, —SO$_3$R$^9$, —CO$_2^-$, and —CO$_2$R$^9$. In a still further aspect, each of R$^{4a}$ and R$^{4b}$, when present, is independently selected from —F, —Cl, —CN, —OH, —NR$^{8a}$R$^{8b}$, NR$^{8a}$R$^{8b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from —F, —Cl, —CN, —OH, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from —F, —Cl, —CN, —OH, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In a still further aspect, each of R$^{4a}$ and R$^{4b}$, when present, is independently selected from —F, —Cl, —CN, —OH, —NR$^{8a}$R$^{8a}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, halogen, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3$, —SO$_3$R$^9$, —CO$_2^-$, and —CO$_2$R$^9$. In an even further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —F, —Cl, —NR$^{8a}$R$^{8b}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$. In a still further aspect, each of R$^{4a}$ and R$^{4b}$, when present, is independently selected from hydrogen, —NR$^{8a}$R$^{8b}$, —NR$^{8a}$R$^{8b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In yet a further aspect, each of R$^{4a}$ and R$^{4b}$, when present, is independently selected from hydrogen, —NR$^{8a}$R$^{8b}$, —NR$^{8a}$R$^{8b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^9$, —CO$_2^-$, and —CO$_2$R$^9$. In an even further aspect, each of R$^{4a}$ and R$^{4b}$, when present, is independently selected from hydrogen, —NR$^{8a}$R$^{8b}$, —NR$^{8a}$R$^{8b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{98}$, —CO$_2^-$, and —CO$_2$R$^9$. In a still further aspect, each of R$^{4a}$ and R$^{4b}$, when present, is independently selected from hydrogen, —NR$^{8a}$R$^{8b}$, —NR$^{8a}$R$^{8b}$H$^+$, —CF$_3$, —CCl$_3$, —SO$_3^-$, —SO$_3$R$^9$, —CO$_2^-$, and —CO$_2$R$^9$.

In a further aspect, each of R$^{4a}$ and R$^{4b}$, when present, is independently selected from hydrogen, —NR$^{8a}$R$^{8b}$, and —NR$^{8a}$R$^{8b}$H$^+$. In a still further aspect, each of R$^{4a}$ and R$^{4b}$, when present, is independently selected from hydrogen and —NR$^{8a}$R$^{8b}$H$^+$. In yet a further aspect, each of R$^{4a}$ and R$^{4b}$, when present, is hydrogen. In an even further aspect, each of R$^{4a}$ and R$^{4b}$, when present, is —NR$^{8a}$R$^{8b}$H$^+$. In a still further aspect, each of R$^{4a}$ and R$^{4b}$, when present, is —NR$^{8a}$R$^{8b}$.

In a further aspect, each of R$^{4a}$ and R$^{4b}$, when present, is independently selected from hydrogen, —SO$_3^-$, and —SO$_3$R$^9$. In a still further aspect, each of R$^{4a}$ and R$^{4b}$, when present, is independently selected from hydrogen and —SO$_3^-$. In yet a further aspect, each of R$^{4a}$ and R$^{4b}$, when present, is —SO$_3^-$. In an even further aspect, each of R$^{4a}$ and R$^{4b}$, is —SO$_3$R$^9$.

In a further aspect, each of R$^{4a}$ and R$^{4b}$, when present, is independently selected from hydrogen, —CO$_2^-$, and —CO$_2$R$^9$.

In a still further aspect, each of R$^{4a}$ and R$^{4b}$, when present, is independently selected from hydrogen and —CO$_2^-$. In yet a further aspect, each of R$^{4a}$ and R$^{4b}$, when present, is —CO$_2^-$. In an even further aspect, each of R$^{4a}$ and R$^{4b}$, is —CO$_2$R$^9$.

h. R$^{5a}$, R$^{5b}$, and R$^{5c}$ Groups

In one aspect, each of R$^{5a}$, R$^{5b}$ and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$. In a further aspect, each of R$^{5a}$, R$^{5b}$, and R$^{5c}$ is independently selected from hydrogen, —F, —Cl, —CN, —OH, —NR$^{10a}$R$^{10b}$, —NR$^{10a}$R$^{10b}$R$^{10c+}$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In a still further aspect, each of each of R$^{5a}$, R$^{5b}$, and R$^{5c}$ is independently selected from hydrogen, —F, —Cl, —CN, —OH, —NR$^{10a}$R$^{10b}$, —NR$^{10a}$R$^{10b}$R$^{10c+}$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In yet a further aspect, each of R$^{5a}$, R$^{5b}$, and R$^{5c}$ is independently selected from hydrogen, —F, —Cl, —CN, —OH, —NR$^{10a}$R$^{10b}$, —NR$^{10a}$R$^{10b}$R$^{10c+}$, methyl, —CH$_2$F, —CH$_2$Cl, —CHF$_2$, —CF$_3$, —CHCl$_2$, —CCl$_3$, —SO$_3^-$, —SO$_3$R$^{11}$, —CO$_2^-$, and —CO$_2$R$^{11}$. In an even further aspect, each of R$^{5a}$, R$^{5b}$, and R$^{5c}$, is independently selected from hydrogen, —F, —Cl, —CN, —OH, —NR$^{10a}$R$^{10b}$, —NR$^{10a}$R$^{10b}$R$^{10c+}$, —CF$_3$, —CCl$_3$, —SO$_3^-$, —SO$_3$R$^{11}$, —CO$_2^-$, and —CO$_2$R$^{11}$.

In a further aspect, each of $R^{5a}$, $R^{5b}$, and $R^{5c}$ is independently selected from halogen, —CN, —OH, —$NR^{10a}R^{10b}$, —$NR^{10a}R^{10b}R^{10c+}$, C1-C4 alkyl, C1-C4 monohaloalkyl, C1-C4 polyhaloalkyl, —$SO_3^-$, —$SO_3R^{11}$, —$CO_2^-$, and —$CO_2R^{11}$. In a still further aspect, each of $R^{5a}$, $R^{5b}$, and $R^{5c}$, when present, is independently selected from —F, —Cl, —CN, —OH, —$NR^{10a}R^{10b}$, —$NR^{10a}R^{10b}R^{10c+}$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In yet a further aspect, each of $R^{5a}$, $R^{5b}$, and $R^{5c}$ is independently selected from —F, —Cl, —CN, —OH, —$NR^{10a}R^{10b}$, —$NR^{10a}R^{10b}R^{10c+}$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In an even further aspect, each of $R^{5a}$, $R^{5b}$, and $R^{5c}$ is independently selected from —F, —Cl, —CN, —OH, —$NR^{10a}R^{10b}$, —$NR^{10a}R^{10b}R^{10c+}$, methyl, —$CH_2F$, —$CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In a still further aspect, each of $R^{5a}$, $R^{5b}$, and $R^{5c}$ is independently selected from —F, —Cl, —CN, —OH, —$NR^{10a}R^{10b}$, —$NR^{10a}R^{10b}R^{10c+}$, —$CF_3$, —$CCl_3$, —$SO_3^-$, —$SO_3R^{11}$, —$CO_2^-$, and —$CO_2R^{11}$.

In a further aspect, each of $R^{5a}$, $R^{5b}$, and $R^{5c}$ is independently selected from hydrogen, halogen, —$NR^{10a}R^{10b}$, —$NR^{10a}R^{10b}R^{10c+}$, C1-C4 alkyl, C1-C4 monohaloalkyl, C1-C4 polyhaloalkyl, —$SO_3^-$, —$SO_3R^{11}$, —$CO_2^-$, and —$CO_2R^{11}$. In a still further aspect, each of $R^{5a}$, $R^{5b}$, and $R^{5c}$ is independently selected from hydrogen, —F, —Cl, —$NR^{10a}R^{10b}$, —$NR^{10a}R^{10b}R^{10c+}$, methyl, ethyl, propyl, —$CH_2F$, —$CH_2Cl$, $CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In yet a further aspect, each of $R^{5a}$, $R^{5b}$, and $R^{5c}$ is independently selected from hydrogen, —F, —Cl, —$NR^{10a}R^{10b}$, —$NR^{10a}R^{10b}R^{10c+}$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In an even further aspect, each of $R^{5a}$, $R^{5b}$, and $R^{5c}$ is independently selected from hydrogen, —F, —Cl, —$NR^{10a}R^{10b}$, —$NR^{10a}R^{10b}R^{10c+}$, methyl, —$CH_2F$, —$CH_2C$, —$CHF_2$, —$CF_3$, —$CHCl_2$, —$CCl_3$, —$SO_3^-$, —$SO_3R^{11}$, —$CO_2^-$, and —$CO_2R^{11}$. In a still further aspect, each of $R^{5a}$, $R^{5b}$, and $R^{5c}$ is independently selected from hydrogen, —F, —Cl, —$NR^{10a}R^{10b}$, —$NR^{10a}R^{10b}R^{10c+}$, —$CF_3$, —$CCl_3$, —$SO_3^-$, —$SO_3R^{11}$, —$CO_2^-$, and —$CO_2R^{11}$.

In a further aspect, each of $R^{5a}$, $R^{5b}$, and $R^{5c}$ is independently selected from hydrogen, —$NR^{10a}R^{10b}$, —$NR^{10a}R^{10b}R^{10c+}$, C1-C4 alkyl, C1-C4 monohaloalkyl, C1-C4 polyhaloalkyl, —$SO_3^-$, —$SO_3R^{11}$, —$CO_2^-$, and —$CO_2R^{11}$. In a still further aspect, each of $R^{5a}$, $R^{5b}$, and $R^{5c}$ is independently selected from hydrogen, —$NR^{10a}R^{10b}$, —$NR^{10a}R^{10b}R^{10c+}$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3$, —$SO_3R^{11}$, —$CO_2^-$, and —$CO_2R^{11}$. In yet a further aspect, each of $R^{5a}$, $R^{5b}$, and $R^{5c}$ is independently selected from hydrogen, —$NR^{10a}R^{10b}$, —$NR^{10a}R^{10b}R^{10c+}$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In an even further aspect, each of $R^{5a}$, $R^{5b}$, and $R^{5c}$ is independently selected from hydrogen, —$NR^{10a}R^{10b}$, —$NR^{10a}R^{10b}R^{10c+}$, methyl, —$CH_2F$, —$CH_2Cl$, —$CHF_2$, —$CF_3$, —$CHCl_2$, —$CCl_3$, —$SO_3^-$, —$SO_3R^{11}$, —$CO_2^-$, and —$CO_2R^{11}$. In a still further aspect, each of $R^{5a}$, $R^{5b}$, and $R^{5c}$ is independently selected from hydrogen, —$NR^{10a}R^{10b}$, —$NR^{10a}R^{10b}R^{10c+}$, —$CF_3$, —$CCl_3$, —$SO_3^-$, —$SO_3R^{11}$, —$CO_2^-$, and —$CO_2R^{11}$.

In a further aspect, each of $R^{5a}$, $R^{5b}$, and $R^{5c}$ is independently selected from hydrogen, —$NR^{10a}R^{10b}$, and —$NR^{10a}R^{10b}R^{10c+}$. In a still further aspect, each of $R^{5a}$, $R^{5b}$, and $R^{5c}$ is independently selected from hydrogen and —$NR^{10a}R^{10b}H^+$. In yet a further aspect, each of $R^{5a}$, $R^{5b}$, and $R^{5c}$ is hydrogen. In an even further aspect, each of $R^{5a}$, $R^{5b}$, and $R^{5c}$ is —$NR^{10a}R^{10b}R^{10c+}$. In a still further aspect, each of $R^{5a}$, $R^{5b}$, and $R^{5c}$ is —$NR^{10a}R^{10b}$.

In a further aspect, each of $R^{5a}$, $R^{5b}$, and $R^{5c}$ is independently selected from hydrogen, —$SO_3^-$, and —$SO_3R^{11}$. In a still further aspect, each of $R^{5a}$, $R^{5b}$, and $R^{5c}$ is independently selected from hydrogen and —$SO_3^-$. In yet a further aspect, each of $R^{5a}$, $R^{5b}$, and $R^{5c}$ is —$SO_3^-$. In an even further aspect, each of $R^{5a}$, $R^{5b}$, and $R^{5c}$ is —$SO_3R^{11}$.

In a further aspect, each of $R^{5a}$, $R^{5b}$, and $R^{5c}$ is independently selected from hydrogen, —$CO_2^-$, and —$CO_2R^{11}$. In a still further aspect, each of $R^{5a}$, $R^{5b}$, and $R^{5c}$ is independently selected from hydrogen and —$CO_2^-$. In yet a further aspect, each of $R^{5a}$, $R^{5b}$, and $R^{5c}$ is —$CO_2^-$. In an even further aspect, each of $R^{5a}$, $R^{5b}$, and $R^{5c}$ is —$CO_2R^{11}$.

i. $R^{6a}$ and $R^{6b}$ Groups

In one aspect, each of $R^{6a}$ and $R^{6b}$, when present, is independently selected from hydrogen, halogen, —CN, —OH, —$NR^{12a}R^{12b}$, —$NR^{12a}R^{12b}H^+$, C1-C4 alkyl, C1-C4 monohaloalkyl, C1-C4 polyhaloalkyl, —$SO_3^-$, —$SO_3R^{13}$, —$CO_2^-$, and —$CO_2R^{13}$. In a further aspect, each of $R^{6a}$ and $R^{6b}$, when present, is independently selected from hydrogen, —F, —Cl, —CN, —OH, —$NR^{12a}R^{12b}$, —$NR^{12a}R^{12b}H^+$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In a still further aspect, each of each of $R^{6a}$ and $R^{6b}$, when present, is independently selected from hydrogen, —F, —Cl, —CN, —OH, —$NR^{12a}R^{12b}$, —$NR^{12a}R^{12b}H^+$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In yet a further aspect, each of $R^{6a}$ and $R^{6b}$, when present, is independently selected from hydrogen, —F, —Cl, —CN, —OH, —$NR^{12a}R^{12b}$, —$NR^{12a}R^{12b}H^+$, methyl, —$CH_2F$, —$CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In an even further aspect, each of $R^{6a}$ and $R^{6b}$, when present, is independently selected from hydrogen, —F, —Cl, —CN, —OH, —$NR^{12a}R^{12b}$, —$NR^{12a}R^{12b}H^+$, —$CF_3$, —$CCl_3$, —$SO_3^-$, —$SO_3R^{13}$, —$CO_2^-$, and —$CO_2R^{13}$.

In a further aspect, each of $R^{6a}$ and $R^{6b}$, when present, is independently selected from halogen, —CN, —OH, —$NR^{12a}R^{12b}$, —$NR^{12a}R^{12b}H^+$, C1-C4 alkyl, C1-C4 monohaloalkyl, C1-C4 polyhaloalkyl, —$SO_3^-$, —$SO_3R^{13}$, —$CO_2^-$, and —$CO_2R^{13}$. In a still further aspect, each of $R^{6a}$ and $R^{6b}$, when present, is independently selected from —F, —Cl, —CN, —OH, —$NR^{12a}R^{12b}$, —$NR^{12a}R^{12b}H^+$, methyl, ethyl, propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In yet a further aspect, each of $R^{6a}$ and $R^{6b}$, when present, is independently selected from —F, —Cl, —CN, —OH, —$NR^{12a}R^{12b}$, —$NR^{12a}R^{12b}H^+$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$SO_3^-$, —$SO_3R^{13}$, —$CO_2^-$, and —$CO_2R^{13}$. In an even further aspect, each of $R^{6a}$ and $R^{6b}$, when present, is independently selected from —F, —Cl, —CN, —OH, —$NR^{12a}R^{12b}$, —$NR^{12a}R^{12b}H^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from —F, —Cl, —CN, —OH, —NR$^{12a}$R$^{12b}$, —NR$^{12a}$R$^{12b}$H$^+$, —CF$_3$, —CCl$_3$, —SO$_3^-$, —SO$_3$R$^{13}$, —CO$_2^-$, and —CO$_2$R$^{13}$.

In a further aspect, each of R$^{6a}$ and R$^{6b}$, when present, is independently selected from hydrogen, halogen, —NR$^{12a}$R$^{12b}$, —NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In yet a further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In an even further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from hydrogen, —F, —Cl, —NR$^{12a}$R$^{12b}$, —NR$^{12a}$R$^{12b}$H$^+$, —CF$_3$, —CCl$_3$, —SO$_3^-$, —SO$_3$R$^{13}$, —CO$_2^-$, and —CO$_2$R$^{13}$.

In a further aspect, each of R$^{6a}$ and R$^{6b}$, when present, is independently selected from hydrogen, —NR$^{12a}$R$^{12b}$, —NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from hydrogen, —NR$^{12a}$R$^{12b}$, —NR$^{12a}$R$^{12b}$H$^+$, methyl, ethyl, propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In yet a further aspect, each of R$^{6a}$ and R$^{6b}$, when present, is independently selected from hydrogen, —NR$^{12a}$R$^{12b}$, —NR$^{12a}$R$^{12b}$H$^+$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In an even further aspect, each of R$^{6a}$ and R$^{6b}$, when present, is independently selected from hydrogen, —NR$^{12a}$R$^{12b}$, —NR$^{12a}$R$^{12b}$H$^+$, methyl, —CH$_2$F, —CH$_2$Cl, —CHF$_2$, —CF$_3$, —CHCl$_2$, —CCl$_3$, —SO$_3^-$, —SO$_3$R$^{13}$, —CO$_2^-$, and —CO$_2$R$^{13}$. In a still further aspect, each of R$^{6a}$ and R$^{6b}$, when present, is independently selected from hydrogen, —NR$^{12a}$R$^{12b}$, —NR$^{12a}$R$^{12b}$H$^+$, —CF$_3$, —CCl$_3$, —SO$_3^-$, —SO$_3$R$^{13}$, —CO$_2^-$, and —CO$_2$R$^{13}$.

In a further aspect, each of R$^{6a}$ and R$^{6b}$, when present, is independently selected from hydrogen, —NR$^{12a}$R$^{12b}$, and —NR$^{12a}$R$^{12b}$H$^+$. In a still further aspect, each of R$^{6a}$ and R$^{6b}$, when present, is independently selected from hydrogen and —NR$^{12a}$R$^{12b}$H$^+$. In yet a further aspect, each of R$^{6a}$ and R$^{6b}$, when present, is hydrogen. In an even further aspect, each of R$^{6a}$ and R$^{6b}$ when present, is —NR$^{12a}$R$^{12b}$H$^+$. In a still further aspect, each of R$^{6a}$ and R$^{6b}$, when present, is —NR$^{12a}$R$^{12b}$.

In a further aspect, each of R$^6$ and R$^{6b}$, when present, is independently selected from hydrogen, —SO$_3^-$, and —SO$_3$R$^{13}$. In a still further aspect, each of R$^{6a}$ and R$^{6b}$, when present, is independently selected from hydrogen and —SO$_3^-$. In yet a further aspect, each of R$^{6a}$ and R$^{6b}$, when present, is —SO$_3^-$. In an even further aspect, each of R$^{6a}$ and R$^{6b}$, when present, is —SO$_3$R$^{13}$.

In a further aspect, each of R$^{6a}$ and R$^{6b}$, when present, is independently selected from hydrogen, —CO$_2^-$, and —CO$_2$R$^{13}$. In a still further aspect, each of R$^{6a}$ and R$^{6b}$, when present, is independently selected from hydrogen and —CO$_2^-$. In yet a further aspect, each of R$^{6a}$ and R$^{6b}$, when present, is —CO$_2^-$. In an even further aspect, each of R$^{6a}$ and R$^{6b}$, when present, is —CO$_2$R$^{13}$.

j. R$^7$ Groups

In one aspect, R$^7$, when present, is selected from hydrogen and C1-C4 alkyl. In a further aspect, R$^7$, when present, is selected from hydrogen, methyl, ethyl, and propyl. In a still further aspect, R$^7$, when present, is selected from hydrogen, methyl, and ethyl. In yet a further aspect, R$^7$, when present, is selected from hydrogen and methyl. In an even further aspect, R$^7$, when present, is hydrogen.

k. R$^{8a}$ and R$^{8b}$ Groups

In one aspect, each of R$^{8a}$ and R$^{8b}$, when present, is selected from hydrogen and C1-C4 alkyl. In a further aspect, each of R$^{8a}$ and R$^{8b}$, when present, is selected from hydrogen, methyl, ethyl, and propyl. In a still further aspect. each of R$^{8a}$ and R$^{8b}$, when present, is selected from hydrogen, methyl, and ethyl. In yet a further aspect, each of R$^{8a}$ and R$^{8b}$, when present, is selected from hydrogen and methyl. In an even further aspect, each of R$^{8a}$ and R$^{8b}$, when present, is hydrogen.

l. R$^9$ Groups

In one aspect, R$^9$, when present, is selected from hydrogen and C1-C4 alkyl. In a further aspect, R$^9$, when present, is selected from hydrogen, methyl, ethyl, and propyl. In a still further aspect, R$^9$, when present, is selected from hydrogen, methyl, and ethyl. In yet a further aspect, R$^9$, when present, is selected from hydrogen and methyl. In an even further aspect, R$^9$, when present, is hydrogen.

m. R$^{10a}$, R$^{10b}$, and R$^{10c}$ Groups

In one aspect, each of R$^{10a}$, R$^{10b}$, and R$^{10c}$, when present, is selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H.

In a further aspect, each of R$^{10a}$, R$^{10b}$, and R$^{10c}$, when present, is selected from hydrogen. In a further aspect, each of R$^{10a}$, R$^{10b}$, and R$^{10c}$, when present is selected from methyl, ethyl, and propyl. In a still further aspect, each of R$^{10a}$, R$^{10b}$, and R$^{10c}$, when present, is selected from methyl, and ethyl. In yet a further aspect, each of R$^{10a}$, R$^{10b}$, and R$^{10c}$, when present, is methyl. In an even further aspect. each of R$^{10a}$, R$^{10b}$, and R$^{10c}$, when present, is hydrogen.

In a further aspect, each of R$^{10a}$, R$^{10b}$, and R$^{10c}$, when present, is selected from —(C1-C8alkylene)SO$_3^-$, —(C1-C8alkylene)SO$_3$H, —(C1-C8alkylene)CO$_2^-$, and —(C1-C8alkylene)CO$_2$H. In a still further aspect, each of R$^{10a}$, R$^{10b}$, and R$^{10c}$, when present, is —(C1-C8alkylene)SO$_3^-$, —(C1-C7alkylene)SO$_3^-$, —(C1-C6alkylene)SO$_3^-$, —(C1-C5alkylene)SO$_3^-$, —(C1-C4alkylene)SO$_3^-$, —(C1-C3alkylene)SO$_3^-$, or —(C1-C2alkylene)SO$_3^-$. In a still further aspect, each of R$^{10a}$, R$^{10b}$, and R$^{10c}$, when present, is —(CH$_2$)$_8$SO$_3^-$, —(CH$_2$)$_7$SO$_3^-$, —(CH$_2$)$_6$SO$_3^-$, —(CH$_2$)$_5$SO$_3^-$, —(CH$_2$)$_4$SO$_3^-$, —(CH$_2$)$_3$SO$_3^-$, —(CH$_2$)$_2$SO$_3^-$, or —CH$_2$SO$_3^-$.

In a still further aspect, each of R$^{10a}$, R$^{10b}$, and R$^{10c}$, when present, is —(C1-C8alkylene)SO$_3$H. In a still further aspect, each of R$^{10a}$, R$^{10b}$, and R$^{10c}$, when present, is —(C1-C8alkylene)SO$_3$H, —(C1-C7alkylene)SO$_3$H, —(C1-C6alkylene)SO$_3$H, —(C1-C5alkylene)SO$_3$H, —(C1-C4alkylene)SO$_3$H, —(C1-C3alkylene)SO$_3$H, or —(C1-C2alkylene)SO$_3$H. In a still further aspect, each of R$^{10a}$, $R^{10b}$, and $R^{10c}$, when present, is —$(CH_2)_8SO_3H$, —$(CH_2)_7SO_3H$, —$(CH_2)_6SO_3H$, —$(CH_2)_5SO_3H$, —$(CH_2)_4SO_3H$, —$(CH_2)_3SO_3H$, —$(CH_2)_2SO_3H$, or —$CH_2SO_3H$.

In a still further aspect, each of $R^{10a}$, $R^{10b}$, and $R^{10c}$, when present, is —(C1-C8alkylene)$CO_2^-$. In a still further aspect, $R^{10}$, when present, is —(C1-C8alkylene)$CO_2^-$, —(C1-C7alkylene)$CO_2^-$, —(C1-C6alkylene)$CO_2^-$, —(C1-C5alkylene)$CO_2^-$, —(C1-C4alkylene)$CO_2^-$, —(C1-C3alkylene)$CO_2^-$, or —(C1-C2alkylene)$CO_2^-$. In a still further aspect, each of $R^{10a}$, $R^{10b}$, and $R^{10c}$, when present, is —$(CH_2)_8CO_2^-$, —$(CH_2)_7CO_2^-$, —$(CH_2)_6CO_2^-$, —$(CH_2)_5CO_2$, —$(CH_2)_4CO_2^-$, —$(CH_2)_3CO_2^-$, —$(CH_2)_2CO_2$, or —$CH_2CO_2^-$.

In a still further aspect, each of $R^{10a}$, $R^{10b}$, and $R^{10c}$, when present, is —(C1-C8alkylene)$CO_2H$. In a still further aspect, each of $R^{10a}$, $R^{10b}$, and $R^{10c}$, when present, is —(C1-C8alkylene)$CO_2H$, —(C1-C7alkylene)$CO_2H$, —(C1-C6alkylene)$CO_2H$, —(C1-C5alkylene)$CO_2H$, —(C1-C4alkylene)$CO_2H$, —(C1-C3 alkylene)$CO_2H$, or —(C1-C2alkylene)$CO_2H$. In a still further aspect, each of $R^{10a}$, $R^{10b}$, and $R^{10c}$, when present, is —$(CH_2)_8CO_2H$, —$(CH_2)_7CO_2H$, —$(CH_2)_6CO_2H$, —$(CH_2)_5CO_2H$, —$(CH_2)_4CO_2H$, —$(CH_2)_3CO_2H$, —$(CH_2)_2CO_2H$, or —$CH_2CO_2H$.

n. $R^{11}$ Groups

In one aspect, $R^{11}$, when present, is selected from hydrogen and C1-C4 alkyl. In a further aspect, $R^{11}$, when present, is selected from hydrogen, methyl, ethyl, and propyl. In a still further aspect, $R^{11}$, when present, is selected from hydrogen, methyl, and ethyl. In yet a further aspect, $R^{11}$, when present, is selected from hydrogen and methyl. In an even further aspect, $R^{11}$, when present, is hydrogen.

o. $R^{12a}$ and $R^{12b}$ Groups

In one aspect, each of $R^{12a}$ and $R^{12b}$, when present, is selected from hydrogen and C1-C4 alkyl. In a further aspect, each of $R^{12a}$ and $R^{12b}$, when present, is selected from hydrogen, methyl, ethyl, and propyl. In a still further aspect, each of $R^{12a}$ and $R^{12b}$, when present, is selected from hydrogen, methyl, and ethyl. In yet a further aspect, each of $R^{12a}$ and $R^{12b}$, when present, is selected from hydrogen and methyl. In an even further aspect, each of $R^{12a}$ and $R^{12b}$, when present, is hydrogen.

p. $R^{13}$ Groups

In one aspect, $R^{13}$, when present, is selected from hydrogen and C1-C4 alkyl. In a further aspect, $R^{13}$, when present, is selected from hydrogen, methyl, ethyl, and propyl. In a still further aspect, $R^{13}$, when present, is selected from hydrogen, methyl, and ethyl. In yet a further aspect, $R^{13}$, when present, is selected from hydrogen and methyl. In an even further aspect, $R^{13}$, when present, is hydrogen.

pH

In some embodiments, the compounds described herein are charged or zwitterionic at a pH from about 1 to about 12. In some embodiments, the compounds are charged or zwitterionic at a pH of about 1, about 2, about 3, about 4, about 5, about 6, about 7, about 8, about 9, about 10, about 11, or about 12. In some embodiments, the compounds are charged or zwitterionic at a pH of less than about 1, less than about 2, less than about 3, less than about 4, less than about 5, less than about 6, less than about 7, less than about 8, less than about 9, less than about 10, less than about 11, or less than about 12. In some embodiments, the compounds are charged or zwitterionic at a pH of greater than about 1, greater than about 2, greater than about 3, greater than about 4, greater than about 5, greater than about 6, greater than about 7, greater than about 8, greater than about 9, greater than about 10, greater than about 11, or greater than about 12.

In some embodiments, the compound has carboxylate group as a negatively charged component. In some embodiments, the compound has a sulfonate group as a negatively charged component. In some embodiments, the compound has a —$NH_3^+$ as a positively charged component. In some embodiments, the compound has a —$NR_2H^+$ as a positively charged component, wherein each R is independently alkyl, heteroalkyl, cycloalkyl, alkenyl, cycloalkenyl, alkynyl, cycloalkynyl, aryl, or heteroaryl group. In some embodiments, the compound has a —$NR_3^+$ as a positively charged component, wherein each R is independently alkyl, heteroalkyl, cycloalkyl, alkenyl, cycloalkenyl, alkynyl, cycloalkynyl, aryl, or heteroaryl group In some embodiments, the compound has a sulfonate group as a negatively charged component and a —$NH_3^+$ as a positively charged component. In some embodiments, the compound has a carboxylate group as a negatively charged component and a —$NH_3^+$ as a positively charged component. In some embodiments, the compound has a sulfonate group as a negatively charged component and a —$NR_2H^+$ as a positively charged component, wherein each R is independently alkyl, heteroalkyl, cycloalkyl, alkenyl, cycloalkenyl, alkynyl, cycloalkynyl, aryl, heteroaryl group, or —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, the compound has a carboxylate group as a negatively charged component and a —$NR_2H^+$ as a positively charged component, wherein each R is independently alkyl, heteroalkyl, cycloalkyl, alkenyl, cycloalkenyl, alkynyl, cycloalkynyl, aryl, heteroaryl group, —(C1-C8alkylene)$SO_3^-$, —(C1-C8alkylene)$SO_3H$, —(C1-C8alkylene)$CO_2^-$, or —(C1-C8alkylene)$CO_2H$. In some embodiments, the compound has a sulfonate group as a negatively charged component and a —$NR_3^+$ as a positively charged component, wherein each R is independently alkyl, heteroalkyl, cycloalkyl, alkenyl, cycloalkenyl, alkynyl, cycloalkynyl, aryl, heteroaryl group, —(C1-C8alkylene) $SO_3^-$, (C1-C8alkylene)$SO_3H$, —(C1-C8alkylene)$CO_2^-$, or —(C1-C8alkylene)$CO_2H$. In some embodiments, the compound has a carboxylate group as a negatively charged component and a —$NR_3^+$ as a positively charged component, wherein each R is independently alkyl, heteroalkyl, cycloalkyl, alkenyl, cycloalkenyl, alkynyl, cycloalkynyl, aryl, heteroaryl group, —(C1-C8alkylene)$SO_3^-$, —(C1-C8alkylene)$SO_3H$, —(C1-C8alkylene)$CO_2^-$, or —(C1-C8alkylene)$CO_2H$.

Energy Providing Devices

In some embodiments, described herein include an energy providing device that comprises a charged compound modified substrate or zwitterion modified substrate. In some instances, the charged compound modified substrate or zwitterion modified substrate comprises a compound having the structure of Formula I described supra. In some instances, also described herein include an energy providing device comprising an electrolyte comprising a perhalogenatedphenyl azide charged or zwitterion compound. In some cases, the perhalogenatedphenyl azide charged or zwitterion compound is a compound having the structure of Formula I described supra. In some instances, Formula I is

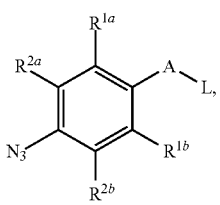

in which A is selected from —C(=O)— and —(SO₂)—; L is selected from —OQ, —O⁻, —N⁺R³HQ and —NR³Q; Q is a structure represented by a formula:

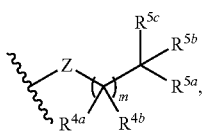

Z is selected from —CR$^{6a}$R$^{6b}$—, —C(=O)—, —C(=NH)—, and —C(=NH)NR⁷—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R³, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H⁺, C1-C4 alkyl, C1-C4 monohaloalkyl, C1-C4 polyhaloalkyl, —SO₃⁻, —SO₃R⁹, —CO₂⁻, and —CO₂R⁹; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO₃⁻, —SO₃R¹¹, —CO₂⁻, and —CO₂R¹¹; each of R$^{6a}$ and R$^{6b}$, when present, is independently selected from hydrogen, halogen, —CN, —OH, —NR$^{12a}$R$^{12b}$, —NR$^{12a}$R$^{12b}$ H⁺, C1-C4 alkyl, C1-C4 monohaloalkyl, C1-C4 polyhaloalkyl, —SO₃⁻, —SO₃R¹³, —CO₂⁻, and —CO₂R¹³; R⁷, when present, is selected from hydrogen and C1-C4 alkyl; each of R$^{8a}$ and R$^{8b}$, when present, is independently selected from hydrogen and C1-C4 alkyl; R⁹, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO₃⁻, —(C1-C8alkylene)SO₃H, —(C1-C8alkylene)CO₂⁻, and —(C1-C8alkylene)CO₂H; R¹¹, when present, is selected from hydrogen and C1-C4 alkyl; each of R$^{12a}$ and R$^{12b}$, when present, is independently selected from hydrogen and C1-C4 alkyl; R¹³, when present, is selected from hydrogen and C1-C4 alkyl, and provided that the compound is charged or zwitterionic.

Separators

In some instances, a substrate described herein includes a separator. In some cases, a separator comprises a separator for an energy storage device, such as batteries. In some cases, a substrate described herein includes a carbon-based separator. In such cases, a carbon-based separator comprises a separator for an energy storage device, such as a supercapacitor. In some cases, a substrate is modified with a charged or zwitterion compound of Formula Ia described above. In some cases, a substrate is modified with a charged or zwitterion compound of Formula Ib described above. In other cases, a substrate is modified with a charged or zwitterion compound of Formula IIa. In additional cases, a substrate is modified with zwitterion compound

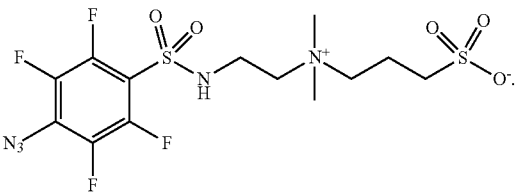

In additional cases, a substrate is modified with zwitterion compound

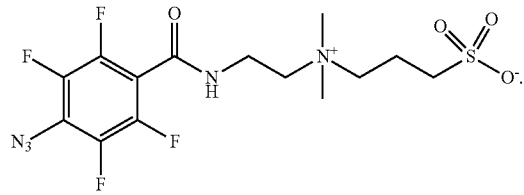

In additional cases, a substrate is modified with charged compound

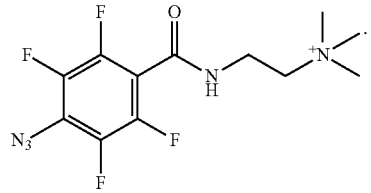 [SMILES: C[N+](C)(C)CCNC(=O)c1c(F)c(F)c(N=[N+]=[N-])c(F)c1F]

In additional cases, a substrate is modified with charged compound

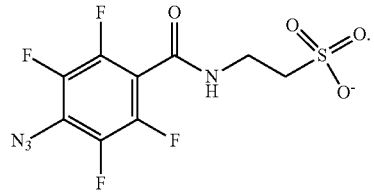

In additional cases, a substrate is modified with charged compound

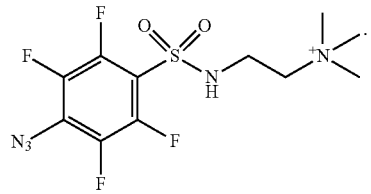 [SMILES: C[N+](C)(C)CCNS(=O)(=O)c1c(F)c(F)c(N=[N+]=[N-])c(F)c1F]

In additional cases, a substrate is modified with charged compound

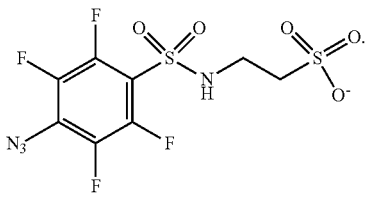

In additional cases, a substrate is modified with charged compound

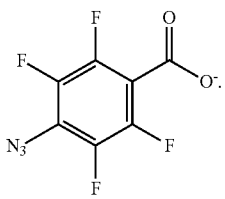

In additional cases, a substrate is modified with charged compound

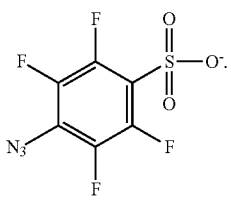

As used herein, a separator is a component that divides or "separates" the positive electrode from the negative electrode within an energy storage device.

In some embodiments, a substrate described herein comprises a polymer-based separator. In some cases, a polymer-based separator comprises a polyolefinic separator. Exemplary polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some instances, a polymer-based separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some cases, the polymer-based separator is a battery separator.

In some embodiments, a separator comprises a microporous separator, a nonwoven separator, an ion-exchange membrane, a supported liquid membrane, or a solid ion conductor. In some instances, a substrate described herein comprises a microporous separator. In some cases, a microporous separator is a polymer-based separator, optionally comprising a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some instances, a substrate described herein comprises a nonwoven separator. In some cases, a nonwoven separator is a polymer-based separator, optionally comprising a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some instances, a substrate described herein comprises an ion-exchange membrane. In some cases, an ion-exchange membrane is a polymer-based separator, optionally comprising a separator modified with polyethylene (PE), polypropylene (PP), polyamide (PA), polytetrafluoroethylene (PTFE), polyvinylidene fluoride (PVDF), polyvinyl chloride (PVC), or a combination thereof. In some cases, an ion-exchange membrane is a Teflon-based film. In some instances, a substrate described herein comprises a supported liquid membrane. In some cases, a supported liquid membrane is a polymer-based separator, optionally comprising a separator modified by polypropylene, polysulfone, polytetrafluoroethylene, cellulose acetate or a combination thereof. In some instances, a substrate described herein comprises a solid ion conductor.

In some embodiments, a substrate described herein comprises a carbon-based separator. In some instances, a carbon-based substrate comprises a polymer moiety. In some cases, the carbon-based substrate comprises a polyolefin moiety. In some cases, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

In some embodiments, a carbon-based separator comprises a graphene-based electrode. In some cases, the graphene-based electrode comprises a porous graphene matrices. In some cases, the porous graphene matrices comprises a three-dimensional intercalated network of single or multiple layers of graphene sheets. In some cases, the graphene-based electrode comprises a corrugated carbon-carbon network. In additional cases, electrolytes that comprise a perhalogenatedphenyl azide charged or zwitterion compound described supra is further deposited on the corrugated carbon-carbon network.

Types of Energy Providing Devices

In some cases, the energy providing device comprises a battery, a supercapacitor, or a fuel cell. In some embodiments, a battery described herein comprises a charged compound modified substrate or zwitterion-modified substrate. In some cases, a battery described herein comprises an electrolyte comprising perhalogenatedphenyl azide charged or zwitterion compound. In some instances, a supercapacitor described herein comprises a charged compound modified substrate or zwitterion-modified substrate. In some cases, a supercapacitor described herein comprises an electrolyte comprising perhalogenatedphenyl azide charged or zwitterion compound. In some instances, a fuel cell described herein comprises a charged compound modified substrate or zwitterion-modified substrate. In some cases, a fuel cell described herein comprises an electrolyte comprising perhalogenatedphenyl azide charged or zwitterion compound. In some embodiments, the charged compound modified substrate or zwitterion modified substrate comprises a compound having the structure of Formula I described supra. In some cases, the perhalogenatedphenyl azide charged or zwitterion compound is a compound having the structure of Formula I described supra.

Types of Energy Providing Devices—Battery

In some embodiments, described herein include a battery that comprises a charged compound modified substrate or zwitterion modified substrate. In some instances, also described herein include a battery that comprises an electrolyte comprising a perhalogenatedphenyl azide charged or zwitterion compound. In some instances, the battery comprises a primary cell or a secondary cell. In some instances the primary, non-rechargeable cell, comprises an alkaline battery, an aluminium-air battery, an aluminium-ion battery, an atomic battery such as a betavoltaics, an optoelectric nuclear battery or a nuclear micro-battery, a bunsen cell, a chromic acid cell (poggendorff cell), a clark cell, a daniell cell, a dry cell, a earth battery, a frog battery, a galvanic cell, a grove cell, a leclanché cell, a lemon/potato battery, a lithium battery, a lithium air battery, a magnesium battery, a mercury battery, a molten salt battery, a nickel oxyhydroxide battery, an organic radical battery, a paper battery, a pulvermacher's chain, a silver-oxide battery, a solid-state battery, a voltaic pile such as a penny battery or a trough battery, a water-activated battery, a weston cell, a zinc-air battery, a zinc-carbon battery, or a zinc chloride battery.

In some instances the secondary, rechargeable cell comprises a flow battery such as a vanadium redox battery, a zinc-bromine battery, or a zinc-cerium battery; a lead-acid battery such as a deep cycle battery, a vrla battery, a agm battery, or a gel battery; a lithium air battery; a lithium-ion battery such as a lithium ion lithium cobalt oxide battery (icr), a lithium ion manganese oxide battery (imr), a lithium ion polymer battery, a lithium iron phosphate battery, a lithium-sulfur battery, a lithium-titanate battery, or a thin film lithium-ion battery; a magnesium-ion battery; a molten salt battery; a nickel-cadmium battery; a nickel hydrogen battery; a nickel-iron battery; a nickel metal hydride battery such as a low self-discharge nimh battery; a nickel-zinc battery; an organic radical battery; a polymer-based battery; a polysulfide bromide battery; a potassium-ion battery; a rechargeable alkaline battery; a rechargeable fuel battery; a silicon air battery; a silver-zinc battery; a silver calcium battery; a sodium-ion battery; a sodium-sulfur battery; a sugar battery; a super iron battery; or an ultrabattery.

In some cases, an atomic, battery (alternatively called a nuclear battery, tritium battery or a radioisotope generator) is a type of primary cell which emits energy from the decay of a radioactive isotope to generate electricity. In most instances, atomic batteries are used as power sources for equipment that must operate unattended for long periods of time, such as spacecraft, pacemakers, underwater systems and automated scientific stations in remote parts of the world, due to their extremely long life and high energy density.

In some cases, a rechargeable flow battery, or redox flow battery is a type of secondary battery composed of two chemical components dissolved in liquids contained within the system and separated by a membrane allow for rechargeability. In some instances, ion exchange occurs through the membrane while both liquids circulate in their own respective space. In some instances, the energy capacity is a function of the electrolyte volume and the power to the surface area of the electrodes. Different classes of flow batteries include redox, hybrid, membrane-less, organic, metal-hydride, nano-network and semi-solid. As flow batteries, can be laid out in a flexible array, have a long cycle life, can be setup quickly, and produce no harmful emissions, they are often used for large-scale energy storage.

In some cases, a lead acid is a secondary energy storage means which employs the reaction of lead and lead oxide with a sulfuric acid electrolyte to produce produces a voltage differential. Lead acid batteries are commonly used for automobile ignition and as backup power supplies.

In some cases, a lithium-ion battery (alternatively called a Li-ion battery or LIB) is a secondary battery in which lithium ions move from the negative electrode, through an electrolyte, to the positive electrode during discharge and are then transferred in reverse to recharge. In some instances, rechargeable lithium-ion batteries use an intercalated lithium compound as one electrode material. In other instances, non-rechargeable lithium-ion batteries use metallic lithium as one electrode material. As lithium-ion batteries display a high energy density, a low memory effect, and a low self-discharge, they are commonly used in in home and portable electronics. Additionally, lithium-ion batteries are becoming a common replacement for the lead acid batteries that have been used historically for golf carts and utility vehicles.

In some cases a water-activated battery is a primary disposable reserve battery that does not contain an electrolyte and hence produces no voltage unless it is soaked in water or an aqueous solution for several minutes. Typically, a large variety of aqueous solutions can be used in place of plain water.

In some cases, one or more of the above batteries are used in combination.

Types of Energy Providing Devices—Supercapacitor

Some embodiments described herein include a supercapacitor that comprises a charged compound modified substrate or zwitterion modified substrate. In some instances, also included herein is a supercapacitor that comprises an electrolyte comprising a perhalogenatedphenyl azide charged or zwitterion compound. In some instances, the supercapacitor comprises an electrochemical double-layer capacitor (EDLC), a pseudocapacitor, or a hybrid supercapacitor.

In some cases, electric double-layer capacitors (EDLC) are electrochemical capacitors, which are a form of supercapacitor. In some instances, double-layer capacitance, electrostatic storage of the electrical energy is achieved by a static separation of charge in a Helmholtz double layer at the interface between the surface of a conductor electrode and an electrolytic solution electrolyte.

In some cases, a pseudocapcacitor (asymmetric supercapacitor) utilizes an underpotential deposition process, redox, or intercalation process in energy storage. In some instances, underpotential deposition is a deposition of, e.g., a metal onto the electrode surface of a second compound (e.g., a second metal) at a reduction potential higher than that when it is deposited onto itself. In some instances, a redox reaction (or Faradaic process) is a charge transfer between an electrode and an electrolyte. In some instances, an intercalation refers to an insertion of cations into the bulk lattice of a solid electrode.

In some cases, a hybrid supercapacitor is a type of asymmetrical supercapacitor which employs electrodes with differing characteristics: one exhibiting mostly electrostatic capacitance and the other mostly electrochemical capacitance.

Types of Energy Providing Devices—Fuel Cell

In some embodiments, a fuel cell is a device that converts a fuel's chemical energy into electricity through a chemical reaction of positively charged hydrogen ions with oxygen or another oxidizing agent. In some embodiments, fuel cells can produce electricity continuously for as long as a continuous source of fuel and oxygen or air to sustain the chemical reaction is supplied.

In some embodiments, a fuel cell is a Polymer electrolyte membrane (PEM) fuel cells, or alternatively named a Proton Exchange Membrane fuel cells, employ a membrane to conduct protons, but not electrons, from the anode to the cathode. Such polymer electrolyte membranes are impermeable to the gases and serve as a solid electrolyte. As such, the chemical energy stored in hydrogen fuel is directly efficiently converted to electrical energy with water as the only byproduct.

In some embodiments, described herein include a polymer electrolyte membrane that comprises a charged or zwitterion compound, e.g., a compound having the structure of Formula I.

Methods of Preparing a Charged Compound Modified Substrate or Zwitterion Modified Substrate In some embodiments, also disclosed herein is a method of preparing a charged or zwitterion modified substrate. In some instances, the method comprises incubating the substrate with a solution comprising a charged or zwitterion compound for at least 40 minutes; and exposing the treated substrate of step a) under a light source for at least one minute, thereby generating the charged compound modified substrate or zwitterion modified substrate. In additional instances, the method comprises (a) contacting a substrate with an alcohol for a time sufficient for the alcohol to saturate the substrate; (b) incubating the saturated substrate with a solution comprising a charged or zwitterion compound for at least 30 seconds; and (c) exposing the substrate of step b) under a light source for at least 30 seconds, thereby generating the charged compound modified substrate or zwitterion modified substrate.

In some embodiments, described herein is a method to modify both monolayer and trilayer separators for use in lithium ion batteries through the functionalization of the polyolefin backbone with charged small molecules. Unlike commercial separators, the modified separators described herein are rapidly and completely wetted upon contact with polar electrolyte liquids resulting in increased electrolyte uptake values, lowered resistance to Li-ion migration, and overall superior battery performance. In some embodiments, the method is scalable. In some embodiments, the modified separators allow for the commercial use of thermally stable, cyclic carbonate-based electrolytes which have been previously hindered by incompatibility with polyolefin separators.

In some embodiments, perfluorophenylazide (PFPA) photochemistry is used to covalently link PFPA containing molecules to the polyolefin chains comprising the separator, including interior pores, through exposure to low-power UV light. In some embodiments, a zwitterionic PFPA derivative is synthesized. In some embodiments, a charged PFPA derivative is synthesized.

In some embodiments, described herein is a method utilizing roll-to-roll production of a polyolefin separator covalently linked to PFPA modified with a charged or zwitterionic compound. In some embodiments, the polyolefin separator is a strip of material that is partially wrapped or leveraged around a series of cylinders or "rolls" which rotate to facilitate the movement of the polyolefin separator along a path. In some embodiments, the polyolefin separator passes through a series of separate solutions. In some embodiments, the polyolefin separator passes through a solution containing a charged or zwitterion compound. In some embodiments, the polyolefin separator passes through a solution containing PFPA modified by charged or zwitterion compound.

In some embodiments, a charged or zwitterion compound comprises a charged or zwitterion compound disclosed above. In some instances, a charged or zwitterion compound is a compound that has the structure of Formula I:

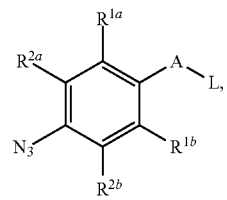

Formula I wherein A is selected from —C(=O)— and —(SO$_2$)—; L is selected from —OQ, —O$^-$, —N$^+$R$^3$HQ and —NR$^3$Q; Q is a structure represented by a formula:

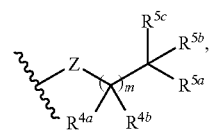

Z is selected from —CR$^{6a}$R$^{6b}$—, —C(=O)—, —C(=NH)—, and —C(=NH)NR$^7$—; m is an integer selected from 0, 1, 2, 3, 4, 5, 6, 7, and 8; each of R$^{1a}$ and R$^{1b}$ is independently selected from hydrogen and halogen; each of R$^{2a}$ and R$^{2b}$ is halogen; R$^3$, when present, is selected from hydrogen and C1-C4 alkyl; each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$; each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$; each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and CO$_2$R$^{13}$; R$^7$, when present, is selected from hydrogen and C1-C4 alkyl; each of R$^{8a}$ and R$^{8b}$, when present, is independently selected from hydrogen and C1-C4 alkyl; R$^9$, when present, is selected from hydrogen and C1-C4 alkyl; each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H; R$^{11}$, when present, is selected from hydrogen and C1-C4 alkyl; each of R$^{12a}$ and R$^{12b}$, when present, is independently selected from hydrogen and C1-C4 alkyl; R$^{13}$, when present, is selected from hydrogen and C1-C4 alkyl, and provided that the compound is charged or zwitterionic.

In some embodiments, the solution in which the substrate in incubated with is a water-alcohol solution. In some instances, the solution in which the substrate in incubated in is a first water-alcohol solution. In some cases, the first water-alcohol solution comprises a water to alcohol ratio of about 90:10, 80:20, 70:30, 60:40, 50:50, 40:60, 33:67, 30:70, 20:80, or 10:90. In some cases, the first water-alcohol solution comprises a water to alcohol ratio of about 90:10. In some cases, the first water-alcohol solution comprises a water to alcohol ratio of about 80:20. In some cases, the first water-alcohol solution comprises a water to alcohol ratio of about 70:30. In some cases, the first water-alcohol solution comprises a water to alcohol ratio of about 60:40. In some cases, the first water-alcohol solution comprises a water to alcohol ratio of about 50:50. In some cases, the first water-alcohol solution comprises a water to alcohol ratio of about 40:60. In some cases, the first water-alcohol solution comprises a water to alcohol ratio of about 33:67. In some cases, the first water-alcohol solution comprises a water to alcohol ratio of about 30:70. In some cases, the first water-alcohol solution comprises a water to alcohol ratio of about 20:80. In some cases, the first water-alcohol solution comprises a water to alcohol ratio of about 10:90. In some cases, the first water-alcohol solution comprises a water to alcohol ratio of at least about 90:10, 80:20, 70:30, 60:40, 50:50, 40:60, 33:67, 30:70, 20:80, or 10:90 and/or no more than about 90:10, 80:20, 70:30, 60:40, 50:50, 40:60, 33:67, 30:70, 20:80, or 10:90.

In some cases, the alcohol comprises methanol, ethanol, 1-propanol, 2-propanol, 2-methyl-2-propanol, 3-methyl-1-butanol, 2,2-dimethyl-1-propanol, cyclopentanol, 1-hexanol, or cyclohexanol. In some cases, the alcohol comprises methanol. In some cases, the alcohol comprises ethanol. In some cases, the alcohol comprises 1-propanol. In some cases, the alcohol comprises 2-propanol. In some cases, the alcohol comprises 2-methyl-2-propanol. In some cases, the alcohol comprises 3-methyl-1-butanol.

In some instances, the concentration of the charged or zwitterion compound of Formula I in the solution is between 1 mM and 10 mM, between 1 mM and 9 mM, between 1 mM and 8 mM, between 1 mM and 7 mM, between 1 mM and 6 mM, between 1 mM and 5 mM, between 1 mM and 4 mM, between 1 mM and 3 mM, between 1 mM and 2 mM, between 1.5 mM and 10 mM, between 1.5 mM and 9 mM, between 1.5 mM and 8 mM, between 1.5 mM and 7 mM, between 1.5 mM and 6 mM, between 1.5 mM and 5 mM, between 1.5 mM and 4 mM, between 1.5 mM and 3 mM, between 1.5 mM and 2 mM, between 2 mM and 10 mM, between 2 mM and 9 mM, between 2 mM and 8 mM, between 2 mM and 7 mM, between 2 mM and 6 mM, between 2 mM and 5 mM, between 2 mM and 4 mM, between 2 mM and 3 mM, between 3 mM and 10 mM, between 3 mM and 8 mM, between 3 mM and 6 mM, between 4 mM and 10 mM, between 4 mM and 8 mM, between 4 mM and 6 mM, between 5 mM and 10 mM, between 5 mM and 8 mM, between 6 mM and 10 mM, or between 8 mM and 10 mM. In some instances, the solution is a water/alcohol mixture. In some instances, the concentration of the charged or zwitterion compound of Formula I in the solution is at least about 1 mM, 2 mM, 3 mM, 4 mM, 5 mM, 6 mM, 7 mM, 8 mM, 9 mM, or 10 mM and/or no more than about 1 mM, 2 mM, 3 mM, 4 mM, 5 mM, 6 mM, 7 mM, 8 mM, 9 mM, or 10 mM.

In some embodiments, a charged or zwitterion compound of Formula I is dissolved in water. In some cases, the concentration of a charged or zwitterion compound of Formula I dissolved in water is between 0.1 mM and 5 mM, between 0.1 mM and 4 mM, between 0.1 mM and 3 mM, between 0.1 mM and 2 mM, between 0.1 mM and 1 mM, between 0.5 mM and 5 mM, between 0.5 mM and 4 mM, between 0.5 mM and 3 mM, between 0.5 mM and 2 mM, between 0.5 mM and 1 mM, between 1 mM and 5 mM, between 1 mM and 4 mM, between 1 mM and 3 mM, between 1 mM and 2 mM, between 1.5 mM and 5 mM, between 1.5 mM and 4 mM, between 1.5 mM and 3 mM, between 1.5 mM and 2 mM, between 2 mM and 5 mM, between 2 mM and 4 mM, between 2 mM and 3 mM, between 3 mM and 5 mM, between 3 mM and 4 mM, or between 4 mM and 5 mM. In some cases, the concentration of a charged or zwitterion compound of Formula I dissolved in water is at least about 0.1 mM, 0.5 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, 5 mM, 6 mM, 7 mM, 8 mM, 9 mM, or 10 mM and/or no more than about 0.1 mM, 0.5 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, 5 mM, 6 mM, 7 mM, 8 mM, 9 mM, or 10 mM.

In some cases, the concentration of a charged or zwitterion compound of Formula I dissolved in water is about 0.1 mM, 0.5 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, 5 mM, 6 mM, 7 mM, 8 mM, 9 mM, or 10 mM. In some instances, the concentration of a charged or zwitterion compound of Formula I dissolved in water is about 0.1 mM. In some instances, the concentration of a charged or zwitterion compound of Formula I dissolved in water is about 0.5 mM. In some instances, the concentration of a charged or zwitterion compound of Formula I dissolved in water is about 1 mM. In some instances, the concentration of a charged or zwitterion compound of Formula I dissolved in water is about 1.1 mM. In some instances, the concentration of a charged or zwitterion compound of Formula I dissolved in water is about 1.2 mM. In some instances, the concentration of a charged or zwitterion compound of Formula I dissolved in water is about 1.3 mM. In some instances, the concentration of a charged or zwitterion compound of Formula I dissolved in water is about 1.4 mM. In some instances, the concentration of a charged or zwitterion compound of Formula I dissolved in water is about 1.5 mM. In some instances, the concentration of a charged or zwitterion compound of Formula I dissolved in water is about 1.6 mM. In some instances, the concentration of a charged or zwitterion compound of Formula I dissolved in water is about 1.7 mM. In some instances, the concentration of a charged or zwitterion compound of Formula I dissolved in water is about 1.8 mM. In some instances, the concentration of a charged or zwitterion compound of Formula I dissolved in water is about 1.9 mM. In some instances, the concentration of a charged or zwitterion compound of Formula I dissolved in water is about 2 mM. In some instances, the concentration of a charged or zwitterion compound of Formula I dissolved in water is about 2.1 mM. In some instances, the concentration of a charged or zwitterion compound of Formula I dissolved in water is about 2.2 mM. In some instances, the concentration of a charged or zwitterion compound of Formula I dissolved in water is about 2.3 mM. In some instances, the concentration of a charged or zwitterion compound of Formula I dissolved in water is about 2.4 mM. In some instances, the concentration of a charged or zwitterion compound of Formula I dissolved in water is about 2.5 mM. In some instances, the concentration of a charged or zwitterion compound of Formula I dissolved in water is about 2.6 mM. In some instances, the concentration of a charged or zwitterion compound of Formula I dissolved in water is about 2.7 mM. In some instances, the concentration of a charged or zwitterion compound of Formula I dissolved in water is about 2.8 mM. In some instances, the concentration of a charged or zwitterion compound of Formula I dissolved in water is about 2.9 mM. In some instances, the concentration of a charged or zwitterion compound of Formula I dissolved in water is about 3 mM. In some instances, the concentration of a charged or zwitterion compound of Formula I dissolved in water is about 4 mM. In some instances, the concentration of a charged or zwitterion compound of Formula I dissolved in water is about 5 mM. In some instances, the concentration of a charged or zwitterion compound of Formula I dissolved in water is about 6 mM. In some instances, the concentration of a charged or zwitterion compound of Formula I dissolved in water is about 7 mM. In some instances, the concentration of a charged or zwitterion compound of Formula I dissolved in water is about 8 mM. In some instances, the concentration of a charged or zwitterion compound of Formula I dissolved in water is about 9 mM. In some instances, the concentration of a charged or zwitterion compound of Formula I dissolved in water is about 10 mM.

In some embodiments, the concentration of the charged or zwitterion compound of Formula I is between 0.1 to 1 mL per square centimeter of the substrate. In some embodiments, the concentration of the charged or zwitterion compound of Formula I is about 0.1, 0.2, 0.3, 0.4, 0.5, 0.6, 0.7, 0.8, 0.9, or 1 mL per square centimeter of the substrate. In some instances, the concentration of the charged or zwitterion compound of Formula I about 0.1 mL per square centimeter of the substrate. In some instances, the concentration of the charged or zwitterion compound of Formula I about 0.2 mL per square centimeter of the substrate. In some instances, the concentration of the charged or zwitterion compound of Formula I about 0.3 mL per square centimeter of the substrate. In some instances, the concentration of the charged or zwitterion compound of Formula I about 0.4 mL per square centimeter of the substrate. In some instances, the concentration of the charged or zwitterion compound of Formula I about 0.5 mL per square centimeter of the substrate. In some instances, the concentration of the charged or zwitterion compound of Formula I about 0.6 mL per square centimeter of the substrate. In some instances, the concentration of the charged or zwitterion compound of Formula I about 0.7 mL per square centimeter of the substrate. In some instances, the concentration of the charged or zwitterion compound of Formula I about 0.8 mL per square centimeter of the substrate. In some instances, the concentration of the charged or zwitterion compound of Formula I about 0.9 mL per square centimeter of the substrate. In some instances, the concentration of the charged or zwitterion compound of Formula I about 1 mL per square centimeter of the substrate. In some embodiments, the concentration of the charged or zwitterion compound of Formula I is at least about 0.1, 0.2, 0.3, 0.4, 0.5, 0.6, 0.7, 0.8, 0.9, or 1 mL per square centimeter of the substrate and/or no more than about 0.1, 0.2, 0.3, 0.4, 0.5, 0.6, 0.7, 0.8, 0.9, or 1 mL per square centimeter of the substrate.

In some instances, the time sufficient for an alcohol to saturate a substrate described herein is at least about 2 seconds, about 3 seconds, about 4 seconds, about 5 seconds, about 10 seconds, about 15 seconds, about 20 seconds, about 30 seconds, or more. In some cases, the time sufficient for the alcohol to saturate the substrate is at least 2 seconds. In some cases, the time sufficient for the alcohol to saturate the substrate is at least 3 seconds. In some cases, the time sufficient for the alcohol to saturate the substrate is at least 4 seconds. In some cases, the time sufficient for the alcohol to saturate the substrate is at least 5 seconds. In some cases, the time sufficient for the alcohol to saturate the substrate is at least 10 seconds. In some cases, the time sufficient for the alcohol to saturate the substrate is at least 15 seconds. In some cases, the time sufficient for the alcohol to saturate the substrate is at least 30 seconds.

In some instances, the time sufficient for an alcohol to saturate a substrate described herein is less than about 5 seconds, less than about 10 seconds, less than about 15 seconds, less than about 20 seconds, less than about 30 seconds, or less than about 1 minute. In some instances, the time sufficient for the alcohol to saturate the substrate is less than 5 seconds. In some instances, the time sufficient for the alcohol to saturate the substrate is less than 10 seconds. In some instances, the time sufficient for the alcohol to saturate the substrate is less than 15 seconds. In some instances, the time sufficient for the alcohol to saturate the substrate is less than 30 seconds. In some instances, the time sufficient for the alcohol to saturate the substrate is less than 1 minute.

In some instances, the time sufficient for an alcohol to saturate a substrate described herein is at least about 1 second, 2 seconds, 3 seconds, 4 seconds, 5 seconds, 10 seconds, 15 seconds, 20 seconds, or about 30 seconds and/or no more than about 1 second, 2 seconds, 3 seconds, 4 seconds, 5 seconds, 10 seconds, 15 seconds, 20 seconds, or about 30 seconds.

In some cases, an alcohol used for saturating a substrate described herein prior to incubating the substrate with a charged or zwitterion compound comprises methanol, ethanol, 1-propanol, 2-propanol, 2-methyl-2-propanol, 3-methyl-1-butanol, 2,2-dimethyl-1-propanol, cyclopentanol, 1-hexanol, cyclohexanol, acetone, methyl ethyl ketone, dimethyl sulfoxide, dimethylformamide, N-methylpyrrolidone, dimethylacetamide, or diethyl carbonate. In some cases, the alcohol is ethanol.

In some cases, an alcohol used for saturating a substrate described herein prior to incubating the substrate with a charged or zwitterion compound comprises less than 10%, 9%, 8%, 7%, 6%, 5%, 4%, 3%, 2%, 1%, 0.5%, or 0.05% water. In some cases, the alcohol comprises less than 1% water. In some cases, the alcohol comprises less than 0.5% water. In some cases, the alcohol comprises less than 0.05% water. In some cases, the alcohol is pure alcohol (e.g., comprising less than 1%, 0.5%, or 0.05% water). In some cases, an alcohol used for saturating a substrate described herein prior to incubating the substrate with a charged or zwitterion compound comprises at least about 0.05%, 0.5%, 1%, 2%, 3%, 4%, 5%, 6%, 7%, 8%, 9%, or about 10% water and/or no more than about 0.05%, 0.5%, 1%, 2%, 3%, 4%, 5%, 6%, 7%, 8%, 9%, or about 10% water.

In some instances, the incubating step lasts for at least 45 minutes, at least 50 minutes, at least 55 minutes, at least 60 minutes, at least 65 minutes, at least 70 minutes, at least 80 minutes, at least 90 minutes, or at least 120 minutes. In some cases, the incubating step lasts for at least 45 minutes. In some cases, the incubating step lasts for at least 50 minutes. In some cases, the incubating step lasts for at least 55 minutes. In some cases, the incubating step lasts for at least 60 minutes. In some cases, the incubating step lasts for at least 70 minutes. In some cases, the incubating step lasts for at least 80 minutes. In some cases, the incubating step lasts for at least 90 minutes.

In some instances, the incubating step lasts for at least 1 minutes, at least 1.5 minutes, at least 2 minutes, at least 3 minutes, at least 4 minutes, at least 5 minutes, at least 10 minutes, at least 15 minutes, or at least 20 minutes. In some cases, the incubating step lasts for at least 1 minutes. In some cases, the incubating step lasts for at least 1.5 minutes. In some cases, the incubating step lasts for at least 2 minutes. In some cases, the incubating step lasts for at least 3 minutes. In some cases, the incubating step lasts for at least 4 minutes.

In some cases, the incubating step lasts for at least 5 minutes. In some cases, the incubating step lasts for at least 10 minutes.

In some instances, the incubating step is less than 30 minutes, less than 20 minutes, less than 15 minutes, less than 10 minutes, less than 9 minutes, less than 8 minutes, less than 7 minutes, less than 6 minutes, less than 5 minutes, less than 4 minutes, less than 3 minutes, less than 2 minutes, or less than 1 minutes.

In some instances, the incubating step is at least about 1, 2, 3, 4, 5, 6, 7, 8, 9, 10, 15, 20, 25, 30, 35, 40, 45, 50, 55, or 60 minutes and/or no more than about 1, 2, 3, 4, 5, 6, 7, 8, 9, 10, 15, 20, 25, 30, 35, 40, 45, 50, 55, or 60 minutes.

In some cases, the incubating step further comprises heating the substrate with the perfluorophenylazide charged or zwitterion derivative of Formula I at a temperature of between 45° C. and 80° C., between 45° C. and 70° C., between 45° C. and 65° C., between 45° C. and 60° C., between 45° C. and 55° C., between 45° C. and 50° C., between 50° C. and 80° C., between 50° C. and 70° C., between 50° C. and 60° C., between 55° C. and 80° C., between 55° C. and 70° C., between 55° C. and 60° C., between 60° C. and 80° C. or between 60° C. and 70° C. In some instances, the substrate is heated when the step of contacting the substrate with pure alcohol is omitted.

In some cases, the incubating step further comprises heating the substrate with the charged or zwitterion compound of Formula I at a temperature of at least 45° C., 50° C., 55° C., 60° C., 65° C., 70° C., 75° C. or 80° C. and/or no more than 45° C., 50° C., 55° C., 60° C., 65° C., 70° C., 75° C. or 80° C. In some cases, the incubating step further comprises heating the substrate with the charged or zwitterion compound of Formula I at a temperature of at least 45° C. In some cases, the incubating step further comprises heating the substrate with the charged or zwitterion compound of Formula I at a temperature of at least 50° C. In some cases, the incubating step further comprises heating the substrate with the charged or zwitterion compound of Formula I at a temperature of at least 55° C. In some cases, the incubating step further comprises heating the substrate with the charged or zwitterion compound of Formula I at a temperature of at least 60° C. In some cases, the incubating step further comprises heating the substrate with the charged or zwitterion compound of Formula I at a temperature of at least 65° C. In some cases, the incubating step further comprises heating the substrate with the charged or zwitterion compound of Formula I at a temperature of at least 70° C. In some cases, the incubating step further comprises heating the substrate with the charged or zwitterion compound of Formula I at a temperature of at least 75° C. In some cases, the incubating step further comprises heating the substrate with the charged or zwitterion compound of Formula I at a temperature of at least 80° C. In some instances, the substrate is heated when the step of contacting the substrate with pure alcohol is omitted.

In some instances, the substrate is not heated at the incubating step when the step of contacting the substrate with pure alcohol (e.g., comprising less than 1%, 0.5%, or 0.05% water) occurs prior to the incubating step.

In some instances, the exposure of the treated substrate under the light source is for at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes. In some cases, the exposure is for at least 2 minutes. In some cases, the exposure is for at least 3 minutes. In some cases, the exposure is for at least 4 minutes. In some cases, the exposure is for at least 5 minutes. In some cases, the exposure is for at least 6 minutes. In some cases, the exposure is for at least 7 minutes. In some cases, the exposure is for at least 8 minutes. In some cases, the exposure is for at least 9 minutes. In some cases, the exposure is for at least 10 minutes. In some cases, the exposure is for at least 15 minutes. In some cases, the exposure is for at least 20 minutes. In some cases, the exposure is for at least 30 minutes. In some instances, the exposure of the treated substrate under the light source is at least about 1, 2, 3, 4, 1, 2, 3, 4, 5, 6, 7, 8, 9, 10, 15, 20, 25, 30, 35, 40, 45, 50, 55, or 60 minutes and/or no more than about 1, 2, 3, 4, 5, 6, 7, 8, 9, 10, 15, 20, 25, 30, 35, 40, 45, 50, 55, or 60 minutes.

In some embodiments, the light source is an ultraviolet light source. In some cases, the ultraviolet light source has an intensity of at least 900 W/cm$^2$. In other cases, the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm. In additional cases, the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm. In additional cases, the ultraviolet light source has a wavelength of no more than 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

In some embodiments, the charged compound modified substrate or zwitterion modified substrate is further incubated in a water-alcohol solution (e.g., a second water-alcohol solution described herein) after exposure with the light source. In some cases, the water-alcohol solution (e.g., a second water-alcohol solution described herein) comprises a water to alcohol ratio of about 90:10, 80:20, 70:30, 60:40, 50:50, 40:60, 33:67, 30:70, 20:80 or 10:90. In some cases, the water-alcohol solution (e.g., a second water-alcohol solution described herein) comprises a water to alcohol ratio of about 90:10. In some cases, the water-alcohol solution (e.g., a second water-alcohol solution described herein) comprises a water to alcohol ratio of about 80:20. In some cases, the water-alcohol solution (e.g., a second water-alcohol solution described herein) comprises a water to alcohol ratio of about 70:30. In some cases, the water-alcohol solution (e.g., a second water-alcohol solution described herein) comprises a water to alcohol ratio of about 60:40. In some cases, the water-alcohol solution (e.g., a second water-alcohol solution described herein) comprises a water to alcohol ratio of about 50:50. In some cases, the water-alcohol solution (e.g., a second water-alcohol solution described herein) comprises a water to alcohol ratio of about 40:60. In some cases, the water-alcohol solution (e.g., a second water-alcohol solution described herein) comprises a water to alcohol ratio of about 33:67. In some cases, the water-alcohol solution (e.g., a second water-alcohol solution described herein) comprises a water to alcohol ratio of about 30:70. In some cases, the water-alcohol solution (e.g., a second water-alcohol solution described herein) comprises a water to alcohol ratio of about 20:80. In some cases, the water-alcohol solution (e.g., a second water-alcohol solution described herein) comprises a water to alcohol ratio of about 10:90.

In some cases, the water-alcohol solution (e.g., a second water-alcohol solution described herein) comprises a water to alcohol ratio of at least about 90:10, 80:20, 70:30, 60:40, 50:50, 40:60, 33:67, 30:70, 20:80 or 10:90 and/or no more than about 90:10, 80:20, 70:30, 60:40, 50:50, 40:60, 33:67, 30:70, 20:80 or 10:90.

In some cases, the alcohol comprises methanol, ethanol, 1-propanol, 2-propanol, 2-methyl-2-propanol, 3-methyl-1-butanol, 2,2-dimethyl-1-propanol, cyclopentanol, 1-hexanol or cyclohexanol. In some cases, the alcohol comprises methanol. In some cases, the alcohol comprises ethanol. In some cases, the alcohol comprises 1-propanol. In some cases, the alcohol comprises 2-propanol. In some cases, the alcohol comprises 2-methyl-2-propanol. In some cases, the alcohol comprises 3-methyl-1-butanol.

In some cases, this incubation step further comprises sonicating the modified substrate in the second water-alcohol solution. In some cases, the sonication is for at least 1 minutes, 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes. In some cases, the sonication is for no more than 1 minutes, 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

In some cases, upon incubation of the modified substrate in the water-alcohol solution (e.g., a second water-alcohol solution described herein), the modified substrate is further dried. In some cases, the modified substrate is air-dried. In other cases, the modified substrate is dried under vacuum.

As discussed elsewhere herein, a modified substrate sometimes is a separator. In some instances, the separator comprises a polymer-based separator. In some cases, the polymer-based separator comprises a polyolefinic separator. In some cases, the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof.

In some instances, the separator comprises a microporous separator, a nonwoven separator, an ion-exchange membrane, a supported liquid membrane, or a solid ion conductor.

In some cases, the substrate comprises a carbon-based substrate containing a moiety capable of binding with the charged or zwitterion compound of Formula I.

In some cases, the carbon-based substrate comprises a polymer moiety. In some cases, the carbon-based substrate comprises a polyolefin moiety. In some cases, the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

Certain Terminology

Unless defined otherwise, all technical and scientific terms used herein have the same meaning as is commonly understood by one of skill in the art to which the claimed subject matter belongs. It is to be understood that the description provided herein is exemplary and explanatory only and is not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance may or may not occur, and that the description includes instances where said event or circumstance occurs and instances where it does not.

As used herein, the terms "effective amount" and "amount effective" refer to an amount that is sufficient to achieve the desired result or to have an effect on an undesired condition.

The term "stable", as used herein, refers to compositions that are not substantially altered when subjected to conditions to allow for their production, detection, and, in certain aspects, their recovery, purification, and use for one or more of the purposes disclosed herein.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "homopolymer" refers to a polymer formed from a single type of repeating unit (monomer residue).

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "cross-linked polymer" refers to a polymer having bonds linking one polymer chain to another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, sulfonate, carboxylate, or thiol, as described herein. A "lower alkyl" group is an alkyl group containing from one to six (e.g., from one to four) carbon atoms. Non-limiting examples of alkyls include C1-18 alkyl, C1-C12 alkyl, C1-C8 alkyl, C1-C6 alkyl, C1-C3 alkyl, and C1 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The term "alkenyl" as used herein is a hydrocarbon group of 2 to 24 carbon atoms with a structural formula containing at least one carbon-carbon double bond. The alkenyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkenyls include C2-18 alkenyl, C2-12 alkenyl, C2-8 alkenyl, C2-6 alkenyl, and C2-3 alkenyl.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. Non-limiting examples of alkynyls include C2-18 alkynyl, C2-12 alkynyl, C2-8 alkynyl, C2-6 alkynyl, and C2-3 alkynyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_8$alkylene. In some embodiments, an alkylene is a $C_1$-$C_6$alkylene. In other embodiments, an alkylene is a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a C3-C6cycloalkyl.

The term "cycloalkenyl" refers to a unsaturated carbocyclyl containing one or more double bonds. Examples of monocyclic cycloalkenyls include, e.g., cyclopentenyl, cyclohexenyl, cycloheptenyl, and cyclooctenyl and the like.

The term "cycloalkynyl" refers to a unsaturated carbocyclyl containing one or more triple bonds. Examples of monocyclic cycloalkynyls include, e.g., cyclopentyne, cycloheptenyl, and cyclooctenyl, cyclooctyne, cyclononyne, and cyclodecyne and the like.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "azide" as used herein is represented by the formula —N$_3$.

The term "thiol" as used herein is represented by the formula —SH.

The term "halo" or, alternatively, "halogen" or "halide" means fluoro, chloro, bromo or iodo. In some embodiments, halogen is fluoro, chloro, or bromo. In some embodiments, halogen is fluoro. In some embodiments, halogen is chloro.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a C6-C10aryl. Depending on the structure, an aryl group is a monoradical or a diradical (i.e., an arylene group).

The term "haloalkyl" refers to an alkyl in which one or more hydrogen atoms are replaced by a halogen atom. "Monohaloalkyl" refers to an alkyl in which one hydrogen atom is replaced with a halogen atom. In some embodiments, monohaloalkyl is C1-C4 monohaloalkyl. "Polyhaloalkyl" refers to an alkyl in which more than one hydrogen atoms are replaced with halogen atoms. In one aspect, a polyahaloalkyl is a C1-C4 polyhaloalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a C1-C6heteroalkyl.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a C1-C9heteroaryl. In some embodiments, monocyclic heteroaryl is a C1-C5heteroaryl. In some embodiments, monocyclic heteroaryl is a 5-membered or 6-membered heteroaryl. In some embodiments, bicyclic heteroaryl is a C6-C9heteroaryl.

The term "zwitterion" or "zwitterionic" refers to a compound that contains both a negatively and positively charged component, wherein the charged components are connected through covalent bonding.

The term "charged compound" or "salt" refers to a compound that contains one or more charged components, wherein any associated counterions are not connected through covalent bonding. In some embodiments, the charged compound contains one or more positive charges. In some embodiments, the charged compound contains one or more negative charges. The charged compound includes counterions to balance the charge.

In some embodiments, a charged or zwitterionic compound has one or more charged components. In some embodiments, the negatively charged component of a compound is a carboxylate. In some embodiments, the negatively charged component of a compound is sulfonate. In some embodiments, the positively charged component of a compound is a protonated amine, —NH$_3^+$. In some embodiments, the positively charged component of a compound is —NR$_2$H$^+$, wherein each R is alkyl, heteroalkyl, cycloalkyl, alkenyl, cycloalkenyl, alkynyl, cycloalkynyl, aryl, heteroaryl group, —(C1-C8alkylene)SO$_3^-$, —(C1-C8alkylene)SO$_3$H, —(C1-C8alkylene)CO$_2^-$, or —(C1-C8alkylene)CO$_2$H. In some embodiments, the positively charged component of a compound is —NR$_3^+$, wherein each R is as described herein for the term amino, such as alkyl, heteroalkyl, cycloalkyl, alkenyl, cycloalkenyl, alkynyl, cycloalkynyl, aryl, heteroaryl group, —(C1-C8alkylene)SO$_3^-$, —(C1-C8alkylene)SO$_3$H, —(C1-C8alkylene)CO$_2^-$, or —(C1-C8alkylene)CO$_2$H.

In some embodiments, the counterion of the charged compounds is Li$^+$, Na$^+$, K$^+$, NH$_4^+$, NR$_4^+$, NR$_3$H$^+$, H$^+$, Mg$^{2+}$, Ca$^{2+}$, F$^-$, Cl$^-$, Br$^-$, I$^-$, OH$^-$, SO$_4^{2-}$, HSO$_4^-$, NO$_3^-$, CN$^-$, N$_3^-$, PF$_6^-$, wherein each R is alkyl.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

The section headings used herein are for organizational purposes only and are not to be construed as limiting the subject matter described.

EXAMPLES

These examples are provided for illustrative purposes only and not to limit the scope of the claims provided herein.

Pentafluorobenzenesulfonyl chloride, N,N-dimethylethylenediamine, and 1,3-propane sultone were purchased from Sigma Aldrich and used as received. All lithium hexafluorophosphate/carbonate electrolyte solutions and lithium tetrafluoroborate were purchased from Sigma Aldrich and stored in an argon-filled glove box. Gamma-butyrolactone was purchased from Sigma Aldrich, dried over $CaSO_4$, and stored over molecular sieves in an argon-filled gloved box. Chloroform, ethanol, and acetone were purchased from Fisher Scientific and used as received. $LiNi_{0.5}Mn_{0.3}Co_{0.2}O_2$ (NMC) cathodes and graphite anodes were purchased from MTI Corporation and opened and stored in an argon-filled glove box. Monolayer PE (Targray) and trilayer PE/PP/PE (Celgard 2320) separators were purchased and used as control separators. 2032 coin-cells were used for EIS and cycling testing.

Nuclear Magnetic Resonance (NMR) spectra were recorded on an Inova-400 or a Bruker-500. $^1H$, $^{13}C$, and $^{19}F$ NMR chemical shifts are given in parts per million ($\delta$) relative to an internal standard; trifluoroethanol (−77.03 ppm). Electrospray mass spectrometry data were collected with a Waters LCT Premier XE time of flight instrument. Samples were infused using a direct loop injection from a Waters Acquity UPLC into the Multi-Mode Ionization source. The flow injection solvent was 1:1 MeOH:MeCN (LCMS Grade, VWR Scientific). The lock mass standard for accurate mass determination was leucine enkephalin (Sigma L9133). UV-vis experiments were performed on a Shimadzu UV-3101PC Spectrophotometer.

Example 1. Synthesis of Perhalogenatedphenyl Azide-Zwitterion Compounds

Synthesis of N-(2-(dimethylamino)ethyl)-2,3,4,5,6-pentafluorobenzenesulfonamide

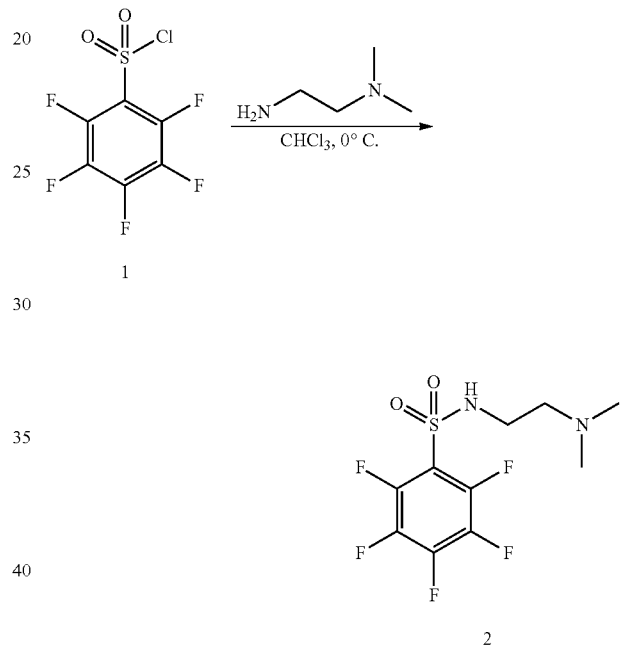

N,N-dimethylethylenediamine (417 μL, 3.82 mmol, 1 eq) and 520 μL of triethylamine were dissolved in 5 mL of $CHCl_3$ and cooled to 0° C. in an ice bath. Separately, pentafluorobenzenesulfonyl chloride (1.018 gram, 3.82 mmol, 1 mL) was dissolved in 5 mL $CHCl_3$ and cooled to 0° C. The two solutions were slowly combined by adding the solution containing the pentafluorobenzenesulfonyl chloride drop wise to the N,Ndimethylethylenediamine solution at 0° C. The ice was replaced every 15 minutes for 1 hour. After 1 hour, the reaction was removed from the ice bath and was allowed to stir at room temperature. After 2 hours, the crude mixture was partitioned between $CHCl_3/H_2O$ and washed with DI water. The organic layer was concentrated under reduced pressure to give N-(2-(dimethylamino)ethyl)-2,3,4,5,6-pentafluorobenzenesulfonamide (875 mg, 72%) as a white solid.

Spec. Data $^1H$ NMR (400 MHz, $CDCl_3$, 25° C., TMS): 2.17 (6H, s), 2.44 (2H, t), 3.19 (2H, t), 5.15 (1H, br s); $^{13}C$ NMR (400 MHz, $CDCl_3$, 25° C., TMS): 40.6, 44.8, 57.5, 116.7, 136.6, 139.2, 142.4, 143.2, 145, 145.8; $^{19}F$ NMR (400 MHz, $CDCl_3$, 25° C., TFE): −135.2 (2F, m), −144.8 (1F, m), −157.1 (2F, m).

Synthesis of 4-azido-N-(2-(dimethylamino)ethyl)-2,3,5,6-tetrafluorobenzene sulfonamide

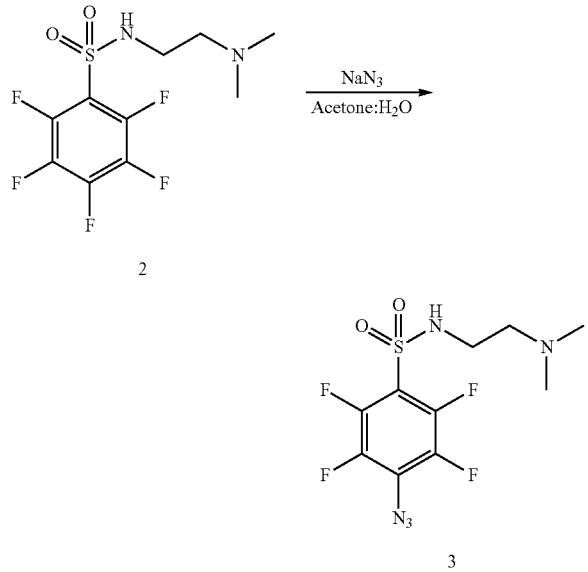

To a solution of N-(2-(dimethylamino)ethyl)-2,3,4,5,6-pentafluorobenzenesulfonamide, (711 mg, 2.23 mmol, 1 mL) in an acetone/H$_2$O mixture (24 mL acetone, 8 mL H$_2$O) was added 524 mg of sodium azide (524 mg, 8.34 mmol, 3.75 eq). The cloudy reaction mixture was allowed to stir overnight in the dark. The crude mixture was diluted with CHCl$_3$ and partitioned between CHCl$_3$/H$_2$O, then washed 3 times with copious amounts of H$_2$O. The organic layer was concentrated under reduced pressure to give 4-azido-N-(2-(dimethylamino)ethyl)-2,3,5,6-tetrafluorobenzenesulfonamide (612 mg, 80%) as an off-white solid.

Spec. Data $^1$H NMR (400 MHz, CDCl$_3$, 25° C., TMS): 2.17 (6H, s), 2.43 (2H, t), 3.17 (2H, t), 5.19 (2H, br s); $^{13}$C NMR (400 MHz, CDCl$_3$, 25° C., TMS): 40.5, 44.8, 57.2, 115.9, 124.4, 139.2, 141.9, 142.9, 145.4; $^{19}$F NMR (400 MHz, CDCl$_3$, 25° C., TFE): −138 (2F, m), −149.7 (2F, m). MS (TOF-ESI+): calculated for C$_{10}$H$_{11}$F$_4$N$_5$O$_2$S+H$^+$ 342.0648, measured 342.0654 (M+H$^+$). UV-vis (EtOH): $\lambda_{max}$=260 nm Synthesis of 3-((2-((4-azido-2,3,5,6-tetrafluorophenyl)sulfonamido)ethyl)dimethylammonio)propane-1-sulfonate

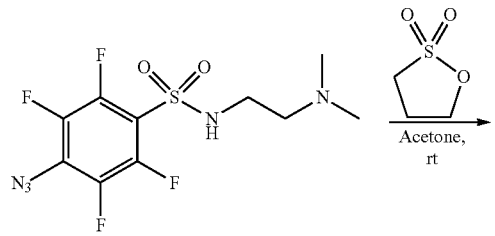

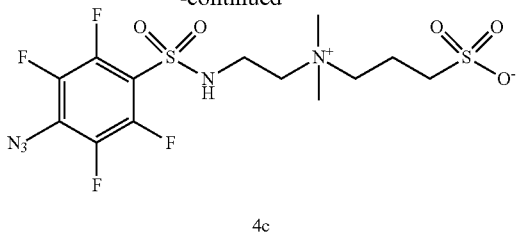

To a solution of 4-azido-N-(2-(dimethylamino)ethyl)-2,3,5,6-tetrafluorobenzenesulfonamide (800 mg, 2.3 mmol, 1 mL) in anhydrous acetone (16 mL, 0.15M) was added 1,3-propane sultone (343 mg, 2.8 mmol, 1.2 mL) in one portion. The mix was allowed to stir overnight in the dark. In the morning the mixture was filtered and the filtrate returned to the initial reaction vessel, covered and allowed to continue stirring. The filtered product was washed 3 times with acetone and dried. This process was repeated in triplicate over the course of the next 4 days to provide a total of 600 mg (52%) of 3-((2-((4-azido-2,3,5,6-tetrafluorophenyl)sulfonamido)ethyl)dimethylammonio)propane-1-sulfonate as a white powder after drying under high vacuum.

Spec. Data $^1$H NMR (500 MHz, [D$_6$]DMSO, 25° C., TMS): 1.96 (2H, m), 2.46 (2H, m), 3.06 (6H, s), 3.45 (6H, m) 9.00 (1H, br s); $^{13}$C NMR (500 MHz, [D$_6$]DMSO, 25° C., TMS): 19.3, 36.5, 47.9, 51, 61.7, 63.1, 114.8, 125.0, 139.8, 141.8, 142.9, 144.9; $^{19}$F NMR (500 MHz, [D$_6$]DMSO, 25° C., TFE): −145.4 (2F, m), −134.5 (2F, m). UV-vis (EtOH): $\lambda_{max}$=264 nm. Mass Spectroscopy: MS (TOF-ESI+): calculated for C$_{13}$H$_{17}$F$_4$N$_5$O$_5$S$_2$+H$^+$464.0685, measured 464.0684 (M+H$^+$).

Example 2. Synthesis, Characterization, and Properties of PFPA-Sulfobetaine Modified Separator A PFPA-sulfobetaine modified separator was prepared according to the procedure described below. A schematic representation illustrating the grafted PFPA-sulfobetaine molecules on the polyolefin separator is shown in FIG. 1. FIG. 1 is an SEM image of a PFPA-sulfobetaine modified polyolefin separator (left) and a schematic representation of PFPA-sulfobetaine molecules grafted onto the exterior and interior surfaces of a polyolefin separator (right). The grafting process allows for PFPA-sulfobetaine molecules to covalently attach to the inner pores of the separator in addition to the exterior surfaces.

Roll-to-Roll Method and System

A roll of commercial polyolefin separator was extruded at a rate of 2.5 cm min$^{-1}$. The separator was rolled through a bath of pure ethanol followed by a bath of 5 mM PFPA-sulfobetaine in DI water. The separator was then moved through a 254 nm UV light exposure zone. Two UV lamps were placed 1 cm apart facing the separator on each side. The separator was subject to UV exposure for 2 min and then immersed in a bath of 1:1 water:ethanol in order to remove any unbound PFPA-zwitterion. The 1:1 water:ethanol bath was continuously purified using an activated carbon filter which removes PFPA-sulfobetaine molecules from the bath. This process was then repeated with the same roll for a total of 5 cycles. The separator was then rolled and dried in a vacuum oven overnight prior to use. This method produced a PFPA-sulfobetaine modified separator.

X-Ray Photoelectron Spectroscopy (XPS)

XPS studies were carried out on a Kratos AXIS Ultra DLD with a monochromatic Al Kα X-ray source operating at 10 mA and 15 kV. Survey spectra and individual high-resolution spectra were collected using pass energies of 160 eV and 10 eV, respectively. Data processing was performed using CasaXPS 2.3 software, and spectra binding energies were calibrated by assigning the hydrocarbon peak in the C 1s high-resolution spectra to 284.6 eV.

XPS was used to confirm the presence of the PFPA-sulfobetaine molecules covalently bound to the polyolefin surfaces, with the atomic percentage relative to carbon present on each sample's surface displayed in Table 1. The commercial hydrocarbon separator surfaces contain mostly carbon with nominal fluorine content (<0.1%) likely resulting from the manufacturing process of the separators. Following the modification, the atomic percentage of fluorine on the polyolefin separator surface is increased from the fluorinated phenyl ring of the PFPA-sulfobetaine molecule. To ensure that the presence of fluorine was not due to physically adsorbed PFPA-sulfobetaine, a separator sample was included that was dipped into the solution containing PFPA-sulfobetaine and rinsed, without exposure to UV light. The surface of this sample contained 0.1% fluorine, demonstrating that a 1:1 EtOH:H$_2$O rinse bath is effective at removing any adsorbed PFPA-sulfobetaine.

TABLE 1

|  | Untreated PE | PFPA-Sulfobetaine PE | Untreated PP/PE/PP | PFPA-Sulfobetaine PP/PE/PP | No UV PFPA-Sulfobetaine PE |
|---|---|---|---|---|---|
| Relative Carbon Percentage | >99.9% | 99.05% | >99.9% | 99.58% | >99.9% |
| Relative Fluorine Percentage | <0.1% | 0.95% | <0.1% | 0.42% | <0.1% |

XPS analysis for untreated and modified separators. F1s % relative to carbon was used to determine the presence of PFPA-Sulfobetaine on the separator surface.

Contact Angle

Contact angles were measured using a First 10 Ångstroms Contact Angle Goniometer. Sessile drop contact angles were taken using DI water on samples of separator that had been desiccated for at least 24 h prior to measurement.

Evidence for surface functionalization was obtained through contact angle measurements using DI water, with the expectation that the introduction of charged functional groups onto the separator surfaces would lead to a decrease in contact angle. The untreated and treated monolayer PE separators exhibited average contact angles of 104.6° and 53.5°, respectively. The untreated trilayer separator had an average contact angle of 97.20 that decreased to 80.8° after modification. Table 2 shows the sessile contact angle measurements of the control and modified monolayer and tri-layer separators.

TABLE 2

|  | Untreated PE | PFPA-Sulfobetaine PE | Untreated PP/PE/PP | PFPA-Sulfobetaine PP/PE/PP |
|---|---|---|---|---|
| Average Contact Angle | 103.8 | 53.5 | 97.2 | 80.8 |
| Standard Deviation | 2.7 | 2.0 | 2.7 | 8.2 |

Sessile contact angle measurements were taken on samples of separator that were dried for at least 24 h prior to the measurements. Average contact angle and standard deviation are shown.

Differential Scanning Calorimetry (DSC)

Differential Scanning Calorimetry (DSC) (Perkin Elmer Differential Scanning Calorimeter) was used to determine the melting point of the untreated and modified separators. The analysis was performed under nitrogen atmosphere with a heating rate of 2° C. min$^{-1}$.

Figures 2A, 2B:
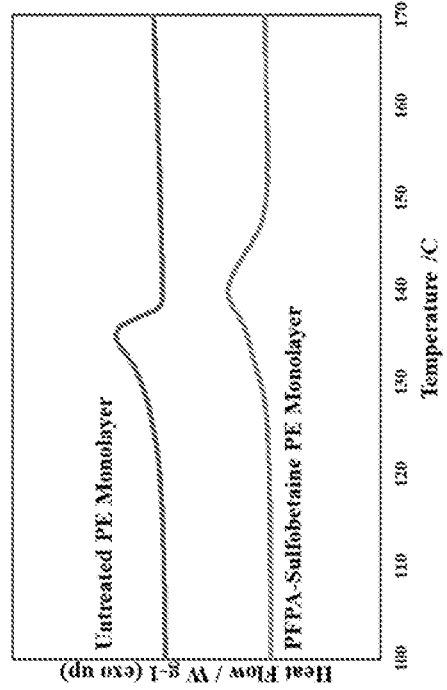
FIG. 2A shows the Differential Scanning Calorimetry (DSC) used to determine the melting temperatures of the untreated PE monolayer (top) and PFPA-sulfobetaine-modified PE monolayer (bottom) separators.
FIG. 2B shows the Differential Scanning Calorimetry (DSC) used to determine the melting temperatures of the untreated PP/PE/PP trilayer (top) and PFPA-sulfobetaine-modified PP/PE/PP trilayer (bottom) separators.

DSC was used to determine the melting point of the modified separators (FIG. 2). Both the unmodified commercial and modified mono-layer PE separators exhibit a melting point close to 135° C. The unmodified commercial and modified tri-layer separators exhibit two melting points at approximately 133° C. (PE) and 158° C. (PP). The minimal change in melting point demonstrates that the PFPA-sulfobetaine surface coating only nominally alters the thermal properties of the separator and the thermal shutdown ability is retained.

Electrolyte Uptake

The electrolyte uptake of the separators was measured by immersing a sample of the separator in an electrolyte for 1 h. The weight of the separator was measured before and after immersion. Excess electrolyte on the separator surface was removed with filter paper prior to measuring the post immersion weight. Electrolyte uptake values are calculated according to Equation 1.

$$((\text{Uptake}=100\%*(W_i-W_o)/W_o)) \quad (1)$$

where $W_i$ represents the weight of the separator post immersion and $W_o$ represents the weight of the separator pre-immersion.

Figure 3:
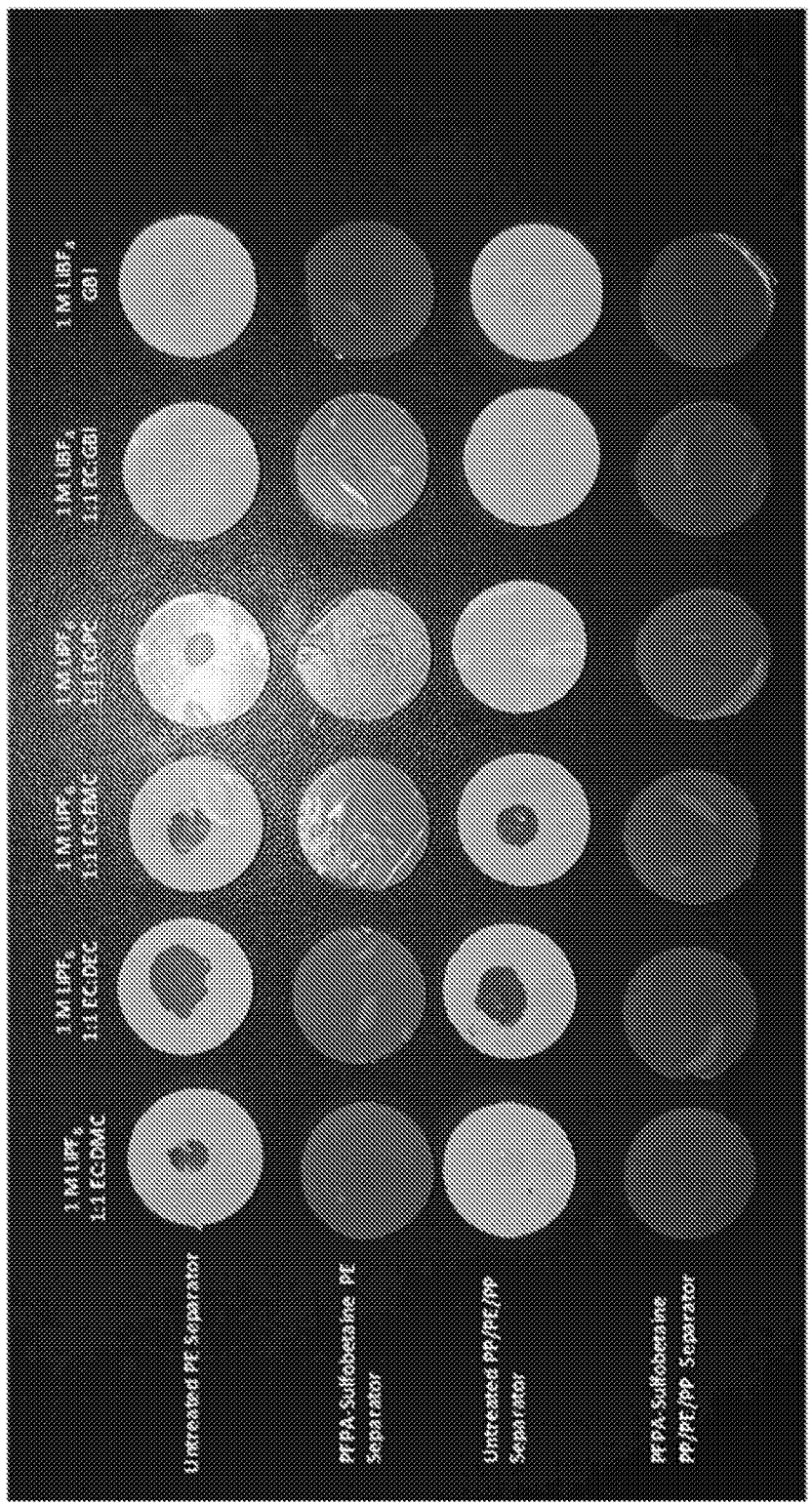
FIG. 3 shows a wettability test of untreated and PFPA-sulfobetaine modified polyolefin separators.
Figure 4:
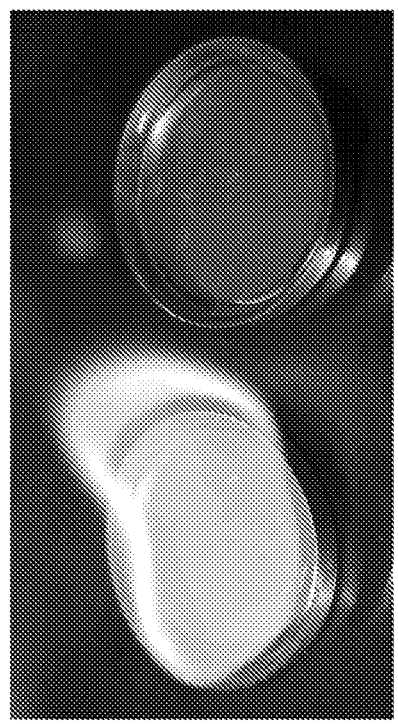
FIG. 4 shows photos of cells containing PFPA-sulfobetaine modified separator and 1.0 M $LiPF_6$ in 1:1 EC:DMC (left) and 1.0 M $LiBF_4$ in GBl (right) after brief exposure to a flame from a butane torch.

The introduction of charged functional groups to the polyolefin surface increases the surface energy of the separator allowing for better absorption of the polar electrolytes. The incorporation of PFPA-sulfobetaine into the polyolefin backbone allows for greater absorption of the electrolyte into the separator. 10 µl of six different electrolytes were pipetted onto samples of polyolefin separator with radii of 8 mm as shown in FIG. 3. 1.0 M LiPF$_6$ in 1:1 EC:DMC, 1:1 EC:EMC, and 1:1 EC:DEC were selected for their commercial applicability. Electrolytes lacking linear carbonates, 1.0 M LiPF$_6$ in 1:1 EC:PC, 1.0 M LiBF$_4$ in 1:1 EC:GBl, and 1.0 M LiBF$_4$ in gamma-butyrolactone (Gbl) were also tested. Samples of PFPA-sulfobetaine modified separators with radii of 8 mm are wetted completely by 10 µl aliquots of electrolyte. The wetting of the separator with electrolytes without linear carbonates (1:1 EC:PC, 1.0 M LiBF$_4$ in 1:1 EC:GBl, 1.0 M LiBF$_4$ in Gbl) is especially notable given the incompatibility with these electrolytes and commercial polyolefin separators. Gbl electrolytes have received attention recently due to their flame resistant nature (FIG. 4), which could potentially be used in LiBs with advanced safety characteristics. Table 3 displays the electrolyte uptake values of separators and electrolytes analogous to those displayed in FIG. 3. Electrolyte uptake values are calculated according to Equation 1.

TABLE 3

|  | 1.0M LiPF6 1:1 EC:DMC | 1.0M LiPF6 1:1 EC:DEC | 1.0M LiPF6 1:1 EC:EMC | 1.0M LiPF6 1:1 EC:PC | 1.0M LiBF4 1:1 EC:GBI | 1.0M LiBF4 1:1 EC:GBI |
|---|---|---|---|---|---|---|
| Untreated PE | 111.1 | 122.2 | 120.0 | 50.0 | 23.1 | 55.6 |
| PFPA-Sulfobetaine PE | 314.3 | 244.4 | 316.7 | 262.5 | 250.0 | 144.4 |
| Untreated PP/PE/PP | 30.0 | 126.7 | 118.2 | 55.6 | 12.5 | 25.0 |
| PFPA-Sulfobetaine PP/PE/PP | 162.5 | 206.7 | 242.9 | 190.0 | 114.3 | 100.0 |

Electrolyte uptake values for commercial vs. PFPA-sulfobetaine modified separators. The electrolyte uptake values describe the wettability of separator samples with different electrolytes.

Electrochemical Properties

Figures 5A, 5B:
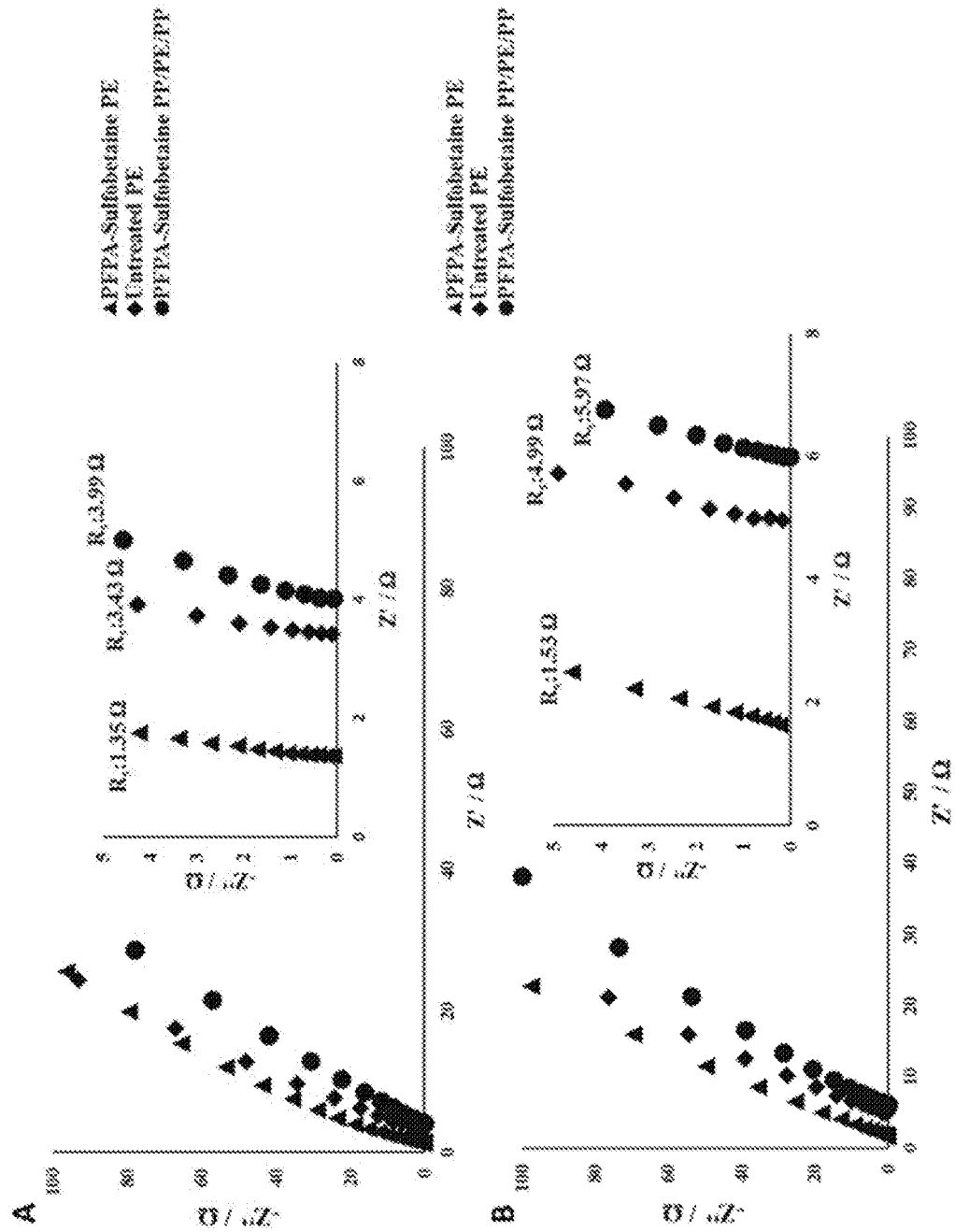
FIG. 5A shows Nyquist plots (Real (Z') vs. Imaginary (Z")) of Stainless steel/Separator/Stainless steel cells made with 1.0 M $LiPF_6$ in 1:1 EC:DMC as the electrolyte. Data for untreated PP/PE/PP trilayer separator could not be obtained due to insufficient wetting of the separator.
FIG. 5B shows Nyquist plots (Real (Z') vs. Imaginary (Z")) of Stainless steel/Separator/Stainless steel cells made with 1.0 M $LiBF_4$ in gamma-butyrolactone as the electrolyte. Data for untreated PP/PE/PP trilayer separator could not be obtained due to insufficient wetting of the separator.

Further evaluation of the effects of incorporation of PFPA-sulfobetaine into polyolefin separators was conducted by electrochemical impedance spectroscopy (EIS). Cells comprised of stainless steel current collectors (SS), electrolyte, and control and modified separators were assembled and subjected to an AC impedance test (FIG. 5). The electrolytes used for this experiment were 1.0 M $LiPF_6$ in 1:1 EC:DMC and 1.0 M $LiBF_4$ in γ-butyrolactone (Gbl). Ionic conductivity values were determined for each cell using the bulk resistance ($R_s$) of the cells. Ionic conductivity was measured by sandwiching the separator between two stainless steel electrodes (1.4 cm in diameter). The separator was soaked with the appropriate electrolyte in an argon atmosphere glovebox prior to cell assembly. The ionic conductivity was obtained using the bulk resistance measured by AC impedance analysis using a Bio-Logic VMP3 potentiostat in the frequency range from 100 Hz to 1.0 MHz. The ionic conductivity value was obtained using Equation 2.

$$\sigma = d/(Rs \cdot SA) \quad (2)$$

where σ represents the ionic conductivity, d is the separator thickness, $R_s$ is the bulk resistance, and SA represents the surface area of the stainless-steel electrodes. While ionic conductivity is mainly determined by the electrolyte, any difference observed in the ionic conductivity of the cells with the same electrolyte and current collectors can be attributed to the separator. Accurate EIS data could not be recorded for cells fabricated with untreated trilayer PP/PE/PP separators due to insufficient wetting of the separator. The observed resistance at high frequencies indicates the bulk resistance ($R_s$).

Ionic conductivity values were calculated using Equation 2. It was confirmed that an increase in the electrolyte uptake leads to a lowering of the bulk resistance of the cell and greater ionic conductivity values. For the commercial electrolyte used, 1.0 M $LiPF_6$ in EC:DMC, the ionic conductivities were 0.20 mS $cm^{-1}$, 0.47 mS $cm^{-1}$, and 0.27 mS $cm^{-1}$ for the untreated monolayer PE, modified monolayer PE membranes and modified trilayer PP/PE/PP membrane, respectively. While the PFPA-sulfobetaine modified trilayer separator exhibited a larger bulk resistance than the untreated PE monolayer separator, the difference in thickness (12 μm compared to 20 μm) results in the PFPA-sulfobetaine cell possessing greater ionic conductivity. For the advanced safety electrolyte used, 1.0 M $LiBF_4$ in Gbl, the ionic conductivities were 0.11 mS $cm^{-1}$, 0.42 mS $cm^{-1}$, and 0.21 mS $cm^{-1}$ for the untreated monolayer PE, modified monolayer PE membrane, and modified trilayer PP/PE/PP membranes, respectively. Increased ionic conductivity values are especially notable given that the small molecule PFPA-sulfobetaine coating adds no appreciable thickness to the membrane. Often, reported increases in ionic conductivity values due to functionalization of the separator are partially due to the added thickness created by the coating layer.

Battery Performance 2032 coin-cells were tested on an 8-Channel Battery Analyzer (MTI Corp). For NMC/graphite cells containing control and modified separators, the cells were cycled from 4.5-3.2 V at a specified constant current. Post cycling AC impedance analysis was carried out using a Bio-Logic VMP3 potentiostat in the frequency range from 0.1 Hz to 1.0 MHz.

Figure 6:
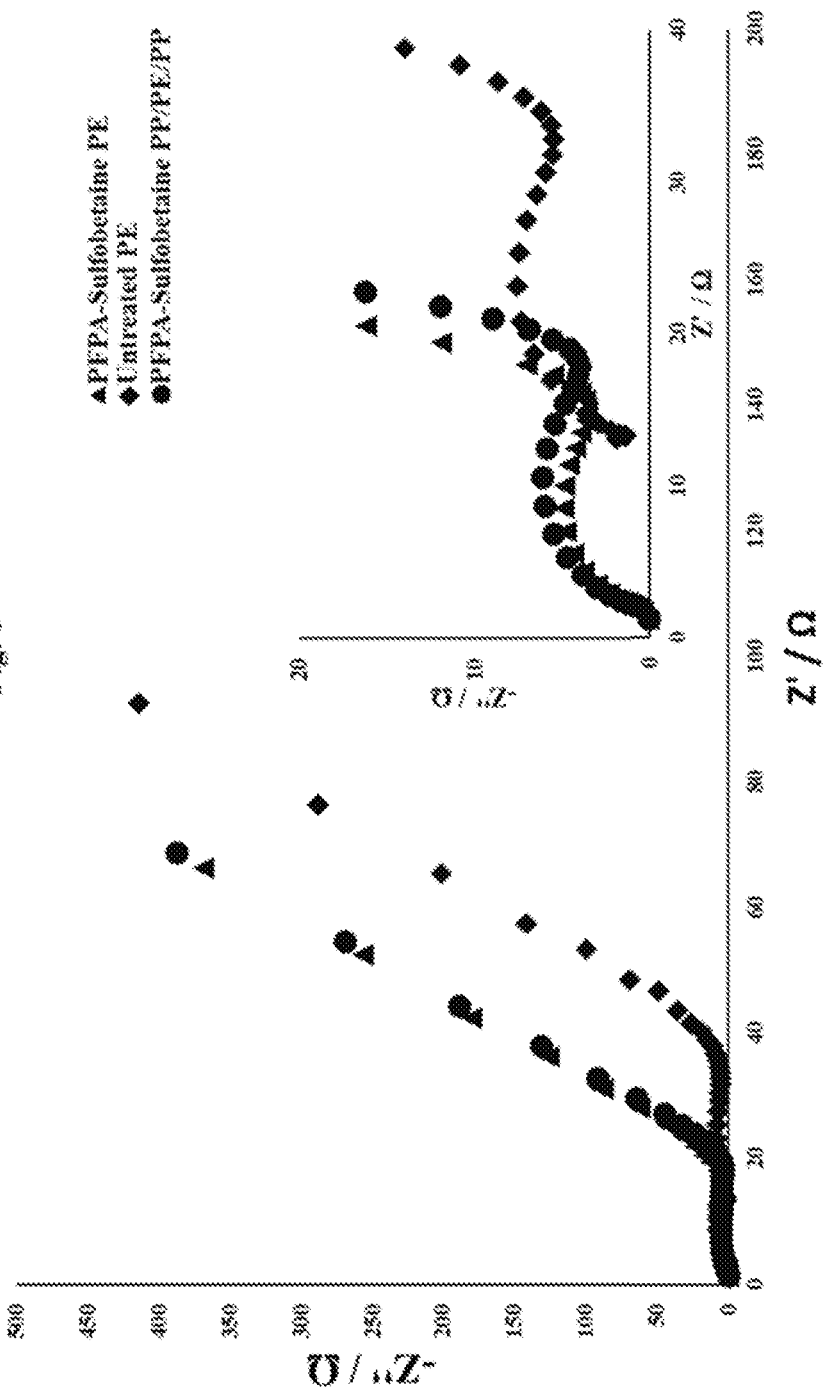
FIG. 6 shows Nyquist plots (Real (Z') vs. Imaginary (Z")) of cells composed of graphite anodes, NMC cathodes, 1.0 M $LiPF_6$ in 1:1 EC:DMC, and separator prior to cycling. Data for untreated PP/PE/PP trilayer separator could not be obtained due to insufficient wetting of the separator.

AC impedance spectra of full cells assembled with graphite anodes, NMC cathodes, 1.0 M $LiPF_6$ in 1:1 EC:DMC, and separators were analyzed. As shown in FIG. 6, the Nyquist plots are composed of one semi-circle in the high frequency range and a line in the mid to low frequency range. Bulk resistances of the cells ($R_b$) are indicated by the x-axis intercepts. Cells containing modified separators have lower bulk resistance values due to the enhanced ionic conductivity of the electrolyte. The semi-circle present in the high frequency range indicates the resistance due to lithium ion migration at the electrode-electrolyte interface ($R_{Int}$). Cells with modified separators exhibit semi-circles with slightly smaller radii than the cell containing an untreated PE separator suggesting that the PFPA-sulfobetaine modification influences the electrode-electrolyte interface. The lowered $R_b$ and $R_{Int}$ values enable faster ion diffusion and more efficient discharge reactions in cells fabricated with PFPA-sulfobetaine modified separators.

Figure 7:
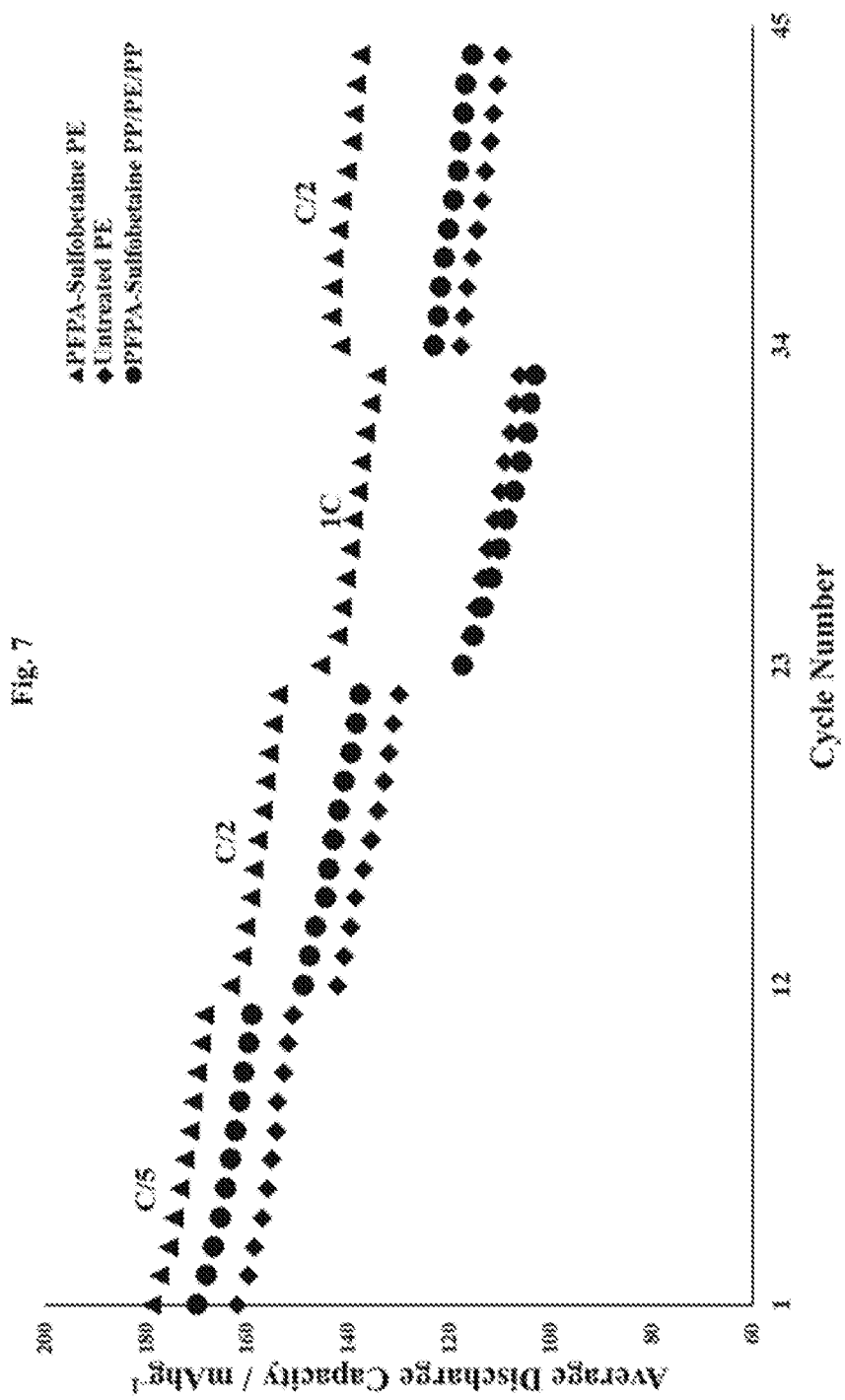
FIG. 7 shows average discharge capacities of NMC/graphite full LiB cells containing 1.0 M $LiPF_6$ 1:1 EC:DMC at C rates of C/5, C/2, and 1 C. Cells were cycled at rates of C/5, C/2, 1 C, and again at C/2 for 11 cycles at each C-rate. Three cells of each type were tested and the results averaged. Cycling data for untreated PP/PE/PP trilayer separator cells could not be obtained due to insufficient wetting of the separator.

The performance of LiB cells constructed with the modified separator was characterized by galvanotactic measurements across a range of current densities (FIG. 7). Coin cells containing graphite anodes, NMC cathodes, and 1.0 M $LiPF_6$ in 1:1 EC:DMC were cycled at rates of C/5, C/2, 1 C, and again at C/2 for 11 cycles each. Three cells were fabricated with each type of separator (untreated PE, PFPA-sulfobetaine PE, and PFPA-sulfobetaine PP/PE/PP) and the discharge capacities for each cycle were averaged. The average initial discharge capacities of the cells with the PFPA-modified PE separator and those with the untreated PE separator were 178.9±4.2 mAh $g^{-1}$ and 161.9±7.9 mAh $g^{-1}$, respectively. The high capacity may be attributed to the improved electrolyte retention and increased ionic conductivity values in cells containing the modified separators. Improved capacity retention upon higher currents (1 C) is also significant, as the cells with the modified separators retained 81.3% of the initial capacity obtained at low current (C/5), whereas the cells with the untreated separators only retained 72.3% of the initial capacity obtained at low current. Also notable was the performance of cells with trilayer separators. Trilayer separators are becoming increasingly popular in commercial LiBs. However, these separators suffer from higher resistances and a greater hindrance of ion diffusion. Therefore, there is strong interest in the mitigation of the high resistance of the trilayer separators. The untreated trilayer-separator was not sufficiently wetted by DMC containing electrolytes and thus cells were nonfunctional and no cycling data could be obtained. Modified trilayer separators, however, demonstrate good cycling capability that is comparable to the cells made with the monolayer separators with an average initial capacity of 169.9±8.1 mAh g$^{-1}$ and 69.1% retention of the initial capacity when cycled at high currents (1 C). The average Coulombic efficiencies are 98.75%, 99.14%, and 98.67% for the cells containing the untreated PE separators, PFPA-sulfobetaine modified PE separators, and PFPA-sulfobetaine modified PP/PE/PP separators, respectively.

Figure 8:
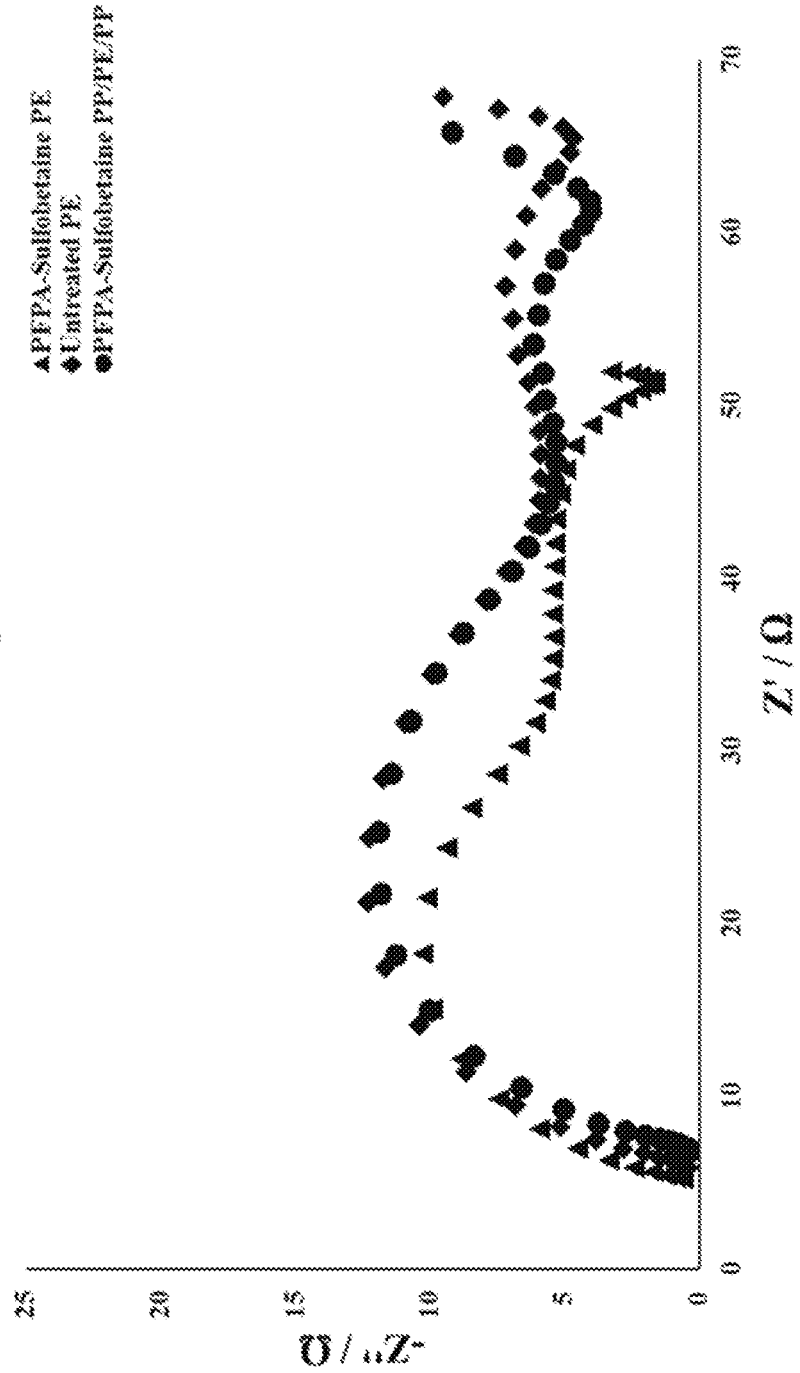
FIG. 8 shows Nyquist plots (Real (Z') vs. Imaginary (Z")) of cells composed of graphite anodes, NMC cathodes, 1.0 M $LiPF_6$ in 1:1 EC:DMC, and the untreated and treated separators after 45 cycles. Cycling data for untreated PP/PE/PP trilayer separator cells could not be obtained due to insufficient wetting of the separator.

Following the cycling tests, the AC impedance spectra of the cells were again analyzed to further elucidate effects of PFPA-sulfobetaine modified separators on cycling performance and discharge capacity, as shown in FIG. 8. In this case, the spectra are composed of two overlapping semi-circles in the mid to high frequency range and an inclined line in the low frequency range. The semi-circle present in the high frequency range (RSEI) represents the resistance to Li-ion migration through the surface films present on the electrodes, commonly known as the solid-electrolyte interface (SEI). The semi-circle present in the mid frequency range ($R_{ct}$) describes the charge transfer resistance between the electrode and electrolyte. The cell containing a PFPA-sulfobetaine PE separator exhibits a significantly smaller RSEI, suggesting that the PFPA-sulfobetaine molecules may affect the SEI formed in this cell, which could contribute to the increase in initial discharge capacity compared to cells containing untreated PE separators. Given the difference in thickness of the monolayer and trilayer separators, it is clear that the PFPA-sulfobetaine modification enhances cell performance.

Example 3. Preparation of a PFPA-Zwitterion Modified Separator

PFPA-Zwitterion in the form of a white powder was dissolved in a solvent mixture of water and ethanol (at 50/50 v/v ratio) to a concentration of 2 mMol. The solution was stirred on a stir plate set to 500 rpm to achieve full solvation of the PFPA-Zwitterion compound in the water/ethanol solvent mixture.

Polyethylene membrane separators were immersed in the PFPA-Zwitterion solution. For every square centimeter of membrane separator, a set amount of PFPA-Zwitterion solution was used. The solution and immersed membrane separator were then heated to a temperature of about 45-60° C. and allowed to soak for 1 hour.

After the one hour soaking period, while remaining immersed in the PFPA-Zwitterion solution, the membrane separator was exposed to 254 nm UV light on both sides for 5 minutes at an intensity of at least 900 μW/cm$^2$. UV exposure initiated the photochemical modification of the polyethylene membrane separator. A schematic of the photoactivated modification is shown below (scheme 1). The PFPA-Zwitterion solution changed from an entirely clear liquid to slightly yellow as it was exposed to the UV light.

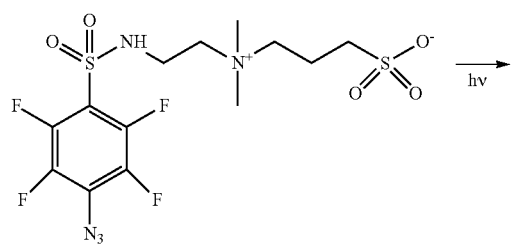

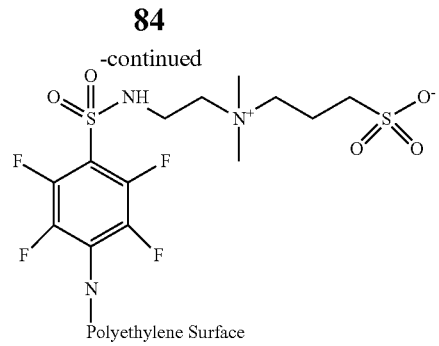

Figure 9:
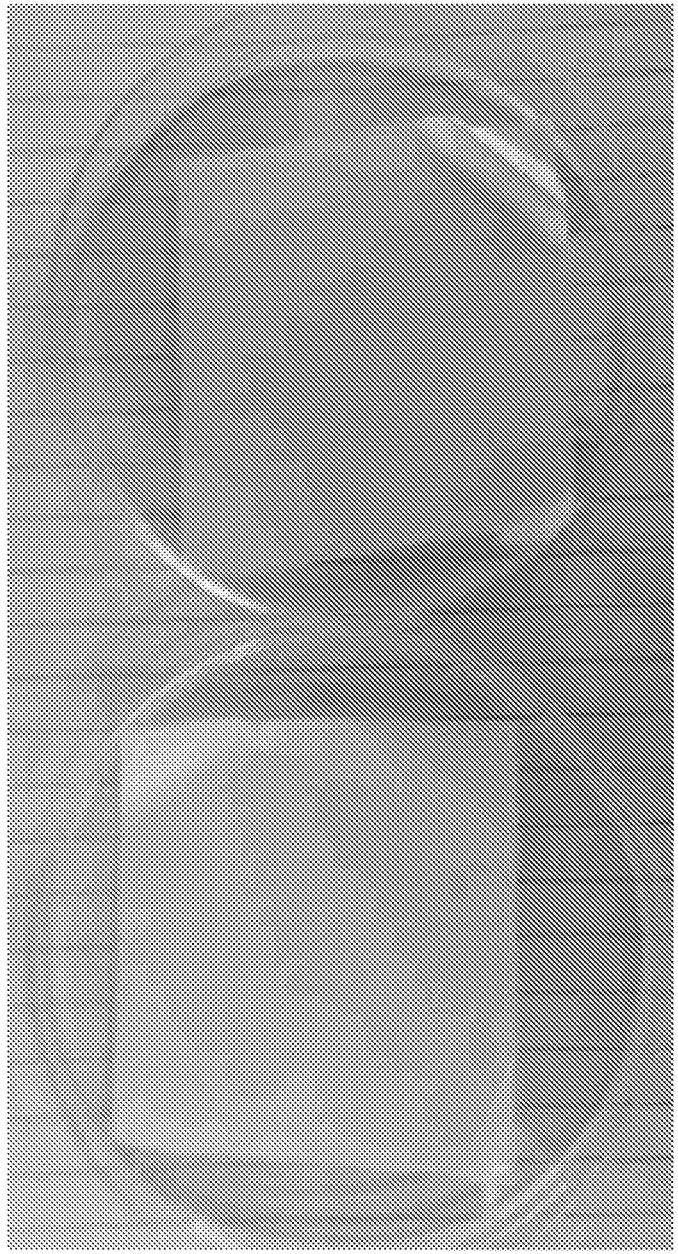
FIG. 9 illustrates an exemplary commercial membrane separator and a modified membrane separator. Upon exposure to UV light, the color of the modified membrane separator changes from clear to a light yellow color relative to the commercial membrane separator.

The modified polyethylene separator was removed from the solution and was washed 2× with a clean mixture of water and ethanol of the same volume and composition as the original modification bath. The modified membrane separator was then immersed in a clean solvent mixture and sonicated for 5 minutes. The membrane separator was then removed and dried under vacuum for 24 hours. The modified membrane separator appears slightly orange when compared to the control (FIG. 9).

Example 3. Electrolyte Uptake of Modified Membrane Separator

Figure 10:
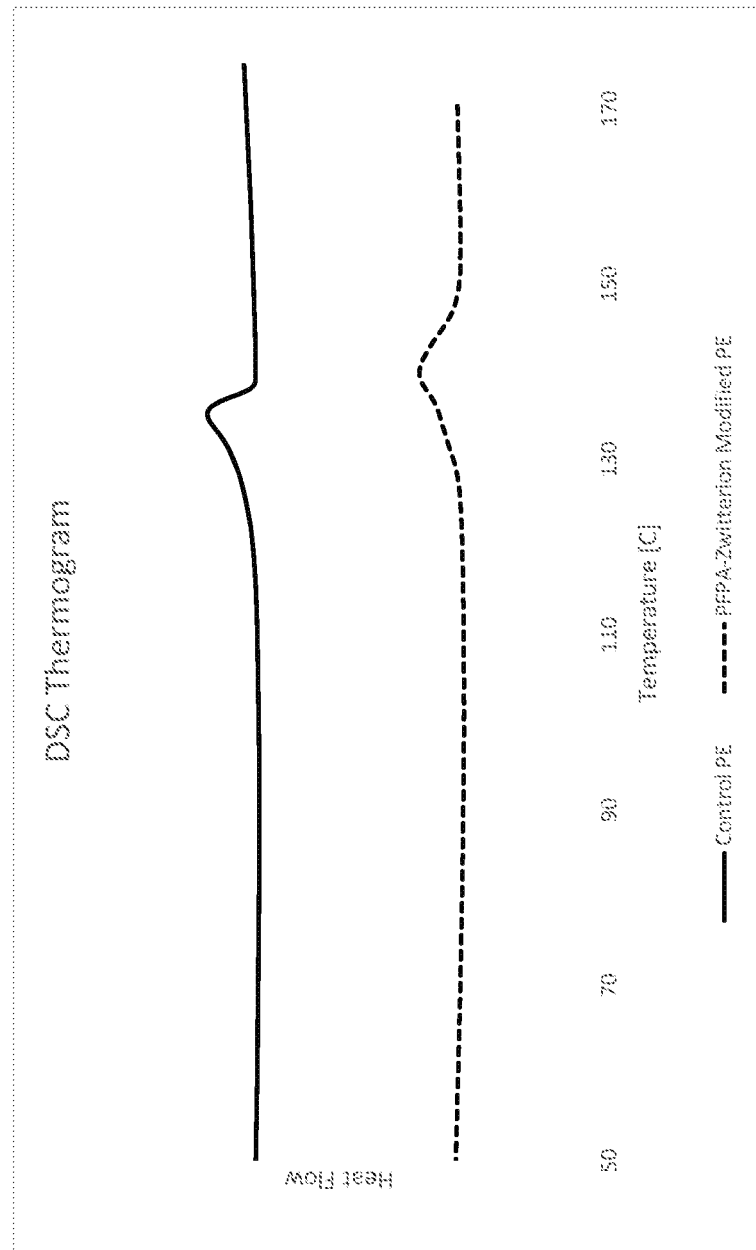
FIG. 10 shows the differential scanning calorimetry (DSC) thermogram of an illustrative modified membrane separator and the DSC thermogram of a control.

FIG. 10 shows the differential scanning calorimetry (DSC) thermogram of another illustrative modified membrane separator in comparison with a control. Each melting point was generated based on three samples. The control (Targray) shows a melting point of 135.1° C. and the illustrative PFPA-zwitterion modified membrane separator shows a melting point of 139.9° C.

Figure 11:
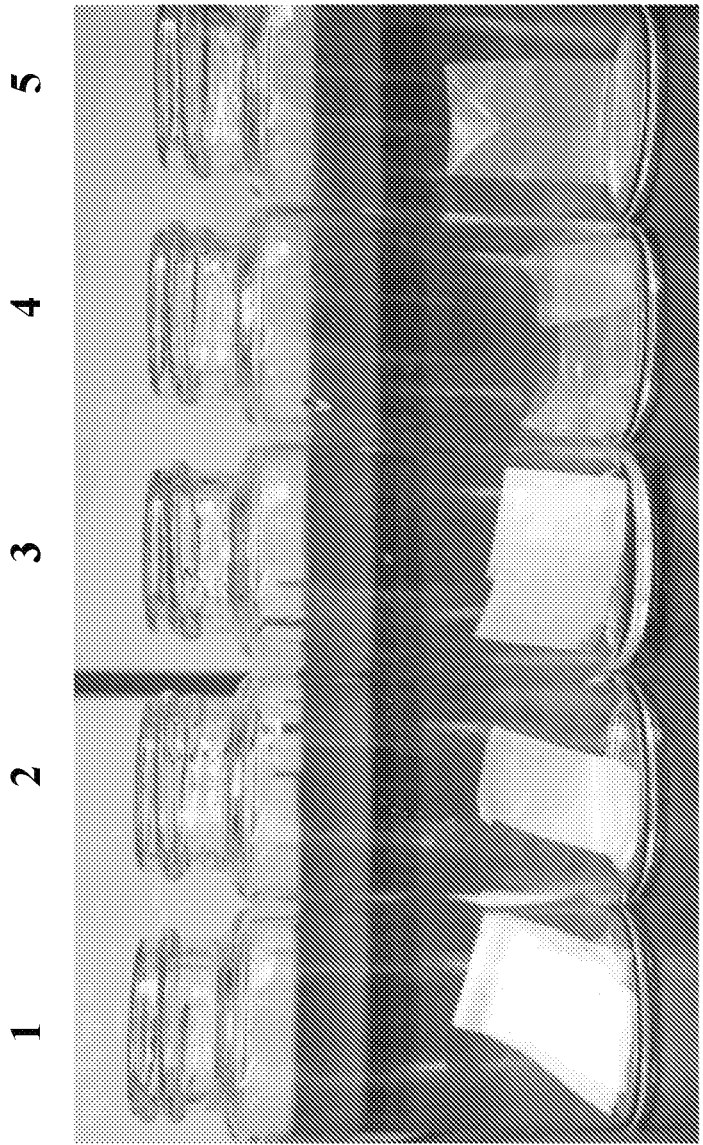
FIG. 11 shows electrolyte uptake based on different temperatures.

FIG. 11 shows electrolyte uptake based on different temperatures. Four different separators were individually immersed in an electrolyte solution of 1:1 ethylene carbonate:propylene carbonate. Sample 1 is an untreated control (Targray). Sample 2 shows a treated separator that was immersed in a PFPA-zwitterion solution at 50° C. without UV exposure. Sample 3 shows a treated separator that was immersed in a PFPA-zwitterion solution at 25° C. with UV exposure treatment for 5 minutes. Sample 4 shows a treated separator that was immersed in a PFPA-zwitterion solution at 50° C. with UV exposure treatment for 1 minute. Sample 5 shows a treated separator that was immersed in a PFPA-zwitterion solution at 50° C. with UV exposure treatment for 5 minutes.

Table 4 shows electrolyte uptake percentage. Polyethylene membrane separator samples were weighed before and after a period of one hour immersed in a lithium ion battery electrolyte solvent. Uptake percentage was calculated from $(W_f-W_o)/W_o$. EC=Ethylene Carbonate, PC=Propylene Carbonate, DMSN=Dimethyl sulfone.

TABLE 4

| ELECTROLYTE | SAMPLE | INITIAL WEIGHT | POST SOAKING WEIGHT | UPTAKE % |
|---|---|---|---|---|
| 1:1 EC:PC | Control | 31.8 | 35.5 | 11.63 |
| 1:1 EC:PC | Modified | 27.1 | 71.2 | 162.73 |
| 3:1 EC:DMSN | Control | 30.3 | 34.7 | 14.52 |
| 3:1 EC:DMSN | Modified | 26.8 | 65.5 | 144.40 |
| Sulfolane | Control | 30.9 | 35.3 | 14.24 |
| Sulfolane | Modified | 25.3 | 62.9 | 148.62 |

Figure 12A:
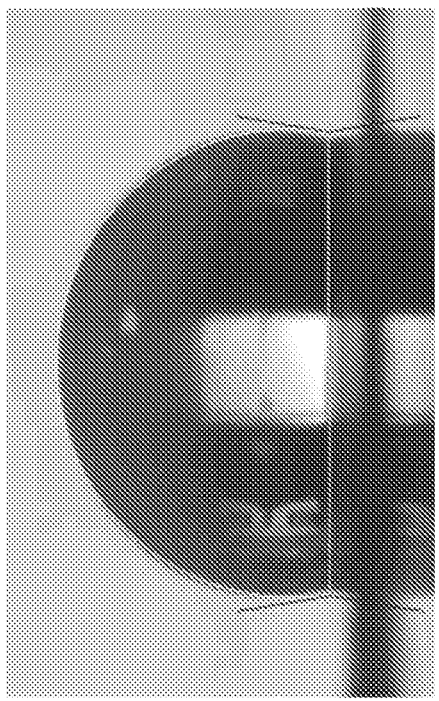
FIG. 12A shows the contact angle of a control membrane (104.77°).
Figure 12B:
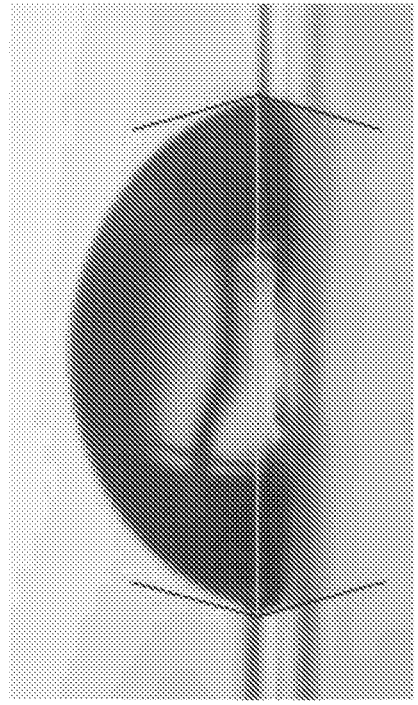
FIG. 12B shows the contact angle of a modified membrane (74.23°).

FIGS. 12A and 12B and Table 5 show the contact angle of an illustrative modified membrane in comparison with a control. FIG. 12A shows a contact angle of 104.77° for the control. FIG. 12B shows a contact angle of 74.23° for a modified membrane.

TABLE 5

|  | MEMBRANE SEPARATOR CONTROL | MODIFIED MEMBRANE SEPARATOR |
|---|---|---|
| Drop 1 | 99.57 | 71.1 |
| Drop 2 | 105.36 | 69.49 |
| Drop 3 | 106.71 | 73.66 |
| Drop 4 | 104.35 | 71.95 |
| Drop 5 | 102.78 | 90.45 |
| Drop 6 | 96.93 | 64.15 |
| Drop 7 | 105.91 | 79.17 |
| Drop 8 | 103.19 | 76.59 |
| Drop 9 | 108 | 76.61 |
| Drop 10 | 102.72 | 72.01 |
| Drop 11 | 108.8 | 77.4 |
| Drop 12 | 110.49 | 74.28 |
| Average | 104.5675 | 74.7383 |
| Average (excluding highest and lowest readings) | 104.77375 | 74.226 |

Figure 13:
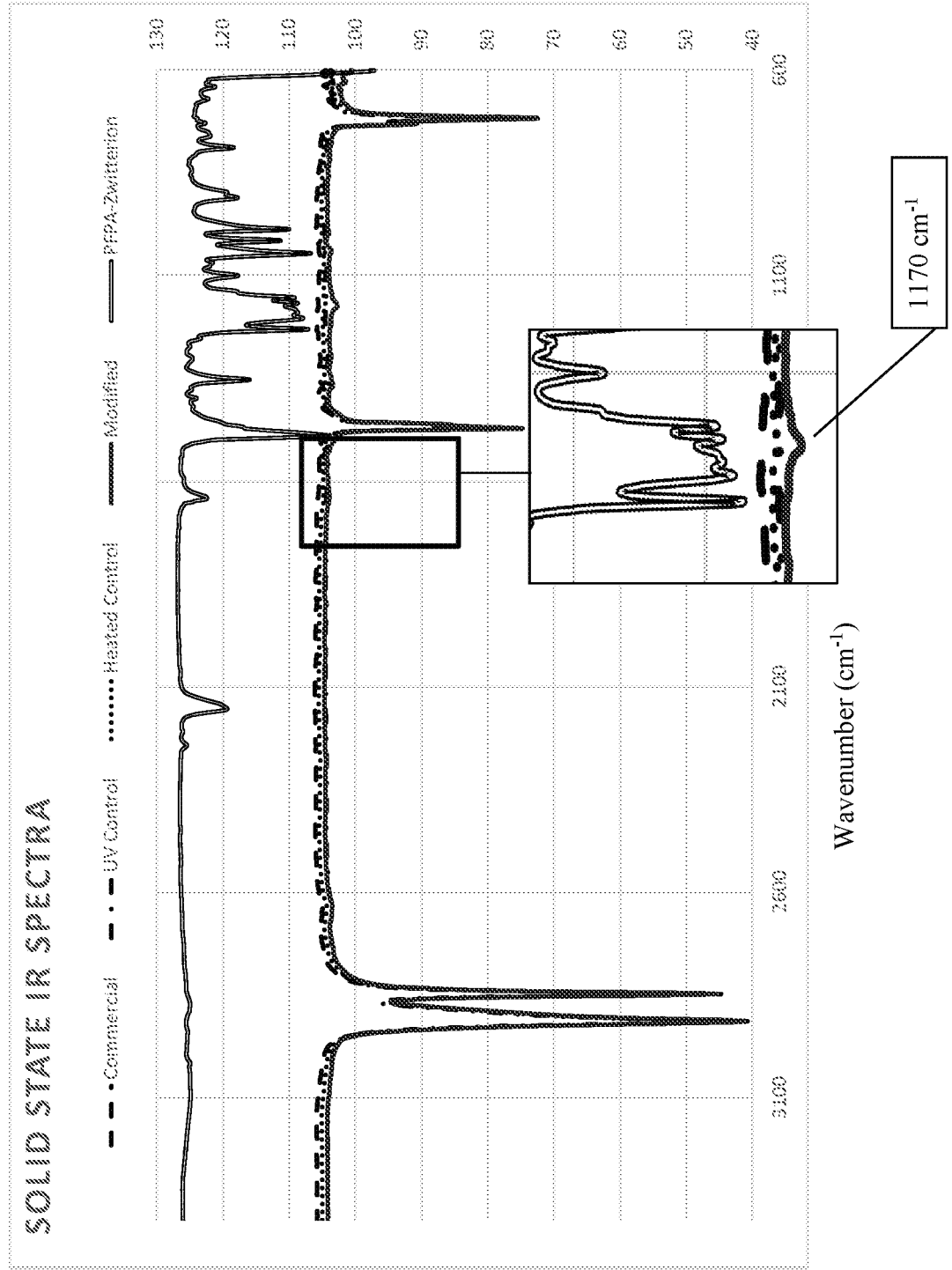
FIG. 13 shows a solid state IR spectrum of a PFPA-Zwitterion compound overlaid with the spectra of various membrane separators.

FIG. 13 shows a solid state IR spectra of a PFPA-Zwitterion compound overlayed with the spectra of various membrane separators. The yellow line represents the membrane separator fully modified with the PFPA-Zwitterion powder. Only the modified membrane separator exhibits peaks similar to those found in the PFPA-Zwitterion spectra. This is most significant on the peak at 1170 cm⁻. The prevalent peaks of 2150 and 1640 cm⁻ in the PFPA-Zwitterion spectra are due to the N3 functional group. These peaks are not apparent on the modified membrane separator due to the chemical nature of the UV activation of the coating which is shown in scheme 1.

Figure 14:
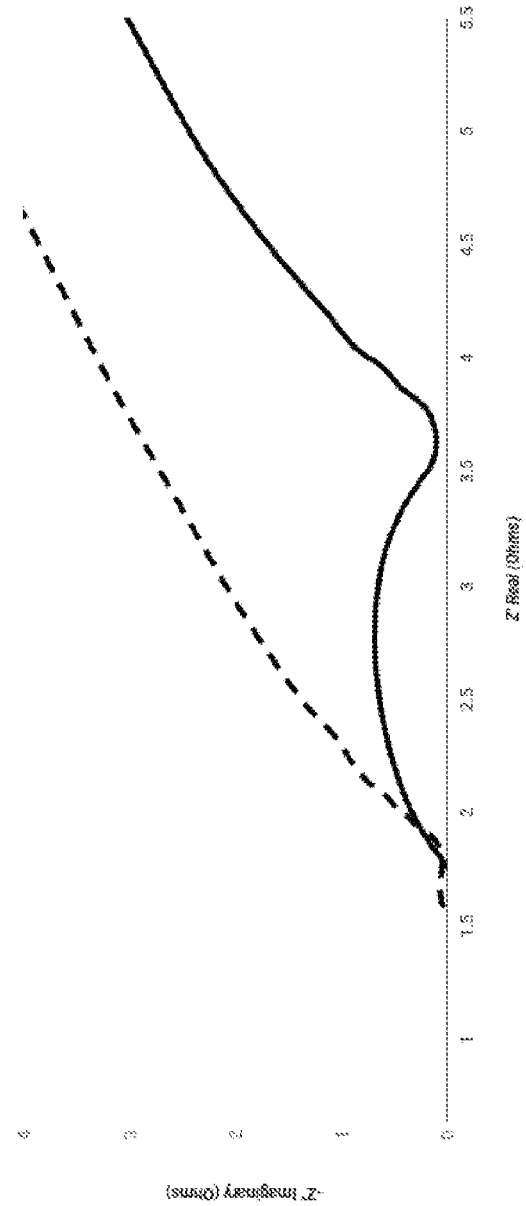
FIG. 14 shows a super capacitor electrochemical impedance spectra of membrane separators.

FIG. 14 shows a super capacitor electrochemical impedance spectra of membrane separators. In some instances, the diameters of semicircles represent the resistance between the Li electrode and the electrolyte-soaked separator. In some cases, a smaller resistance indicates ions are more able to flow through the modified separator than the commercial membrane separator.

Figure 15:
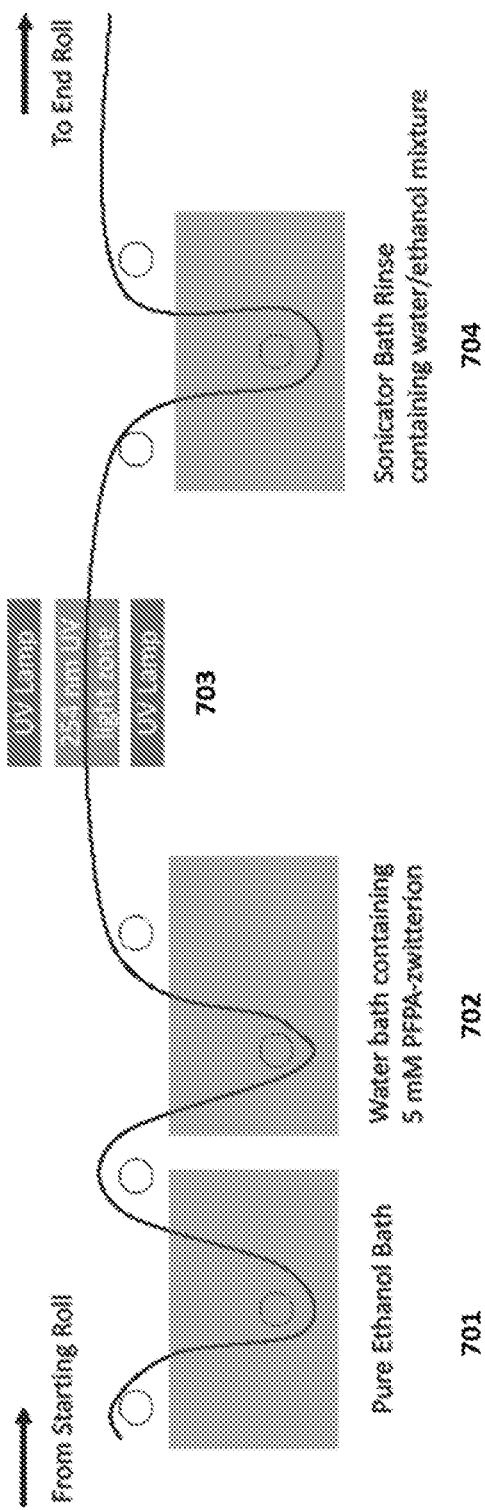
FIG. 15 illustrates a "roll-to-roll" method of preparing a PFPA-zwitterion modified separator.

Example 4. A "Roll-to-Roll" Method of Preparing a PFPA-Zwitterion Modified Separator FIG. 15 illustrates a "roll-to-roll" method of preparing a PFPA-zwitterion modified separator, in which the separator was "rolled" from one station to the next station (e.g., from 701-704). In brief, a dry separator film was soaked in a solution of pure ethanol for about 5 seconds to wet the separator (701). Then, the separator was incubated with a solution comprising about 5 mM PFPA-zwitterion dissolved in pure water (702) to exchange the PFPA-zwitterion and water with ethanol. Next, the separator that is swollen with the PFPA-zwitterion and water solvent is exposed to UV light (about 254 nm) (703) for about 30 second. The UV-treated separator was then washed and sonicated in 704 in a water/ethanol bath (50:50 v/v). After sonication, the separator was vacuum dried. This system allows for the continuous modification of commercial separators, enabling several meters to be produced under ambient conditions at low cost.

Example 5. Preparation of Sodium 4-Azido-2,3,5,6-Tetrafluorobenzoate Modified Separator Sodium 4-azido-2,3,5,6-tetrafluorobenzoate in the form of a white powder was dissolved in a solvent mixture of water and ethanol (at 50/50 v/v ratio) to a concentration of 2 mMol. The solution was stirred on a stir plate set to 500 rpm to achieve full solvation of the sodium 4-azido-2,3,5,6-tetrafluorobenzoate in the water/ethanol solvent mixture.

Polyethylene membrane separators were immersed in the sodium 4-azido-2,3,5,6-tetrafluorobenzoate solution. For every square centimeter of membrane separator, a set amount of sodium 4-azido-2,3,5,6-tetrafluorobenzoate solution was used. The solution and immersed membrane separator were then heated to a temperature of about 45-60° C. and allowed to soak for 1 hour.

After the one hour soaking period, while remaining immersed in the sodium 4-azido-2,3,5,6-tetrafluorobenzoate solution, the membrane separator was exposed to 254 nm UV light on both sides for 5 minutes at an intensity of at least 900 $\mu W/cm^2$. UV exposure initiated the photochemical modification of the polyethylene membrane separator.

The modified polyethylene separator was removed from the solution and was washed 2× with a clean mixture of water and ethanol of the same volume and composition as the original modification bath. The modified membrane separator was then immersed in a clean solvent mixture and sonicated for 5 minutes. The membrane separator was then removed and dried under vacuum for 24 hours.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

ADDITIONAL EMBODIMENTS

Embodiment 1 is an energy providing device comprising a charged compound modified substrate or zwitterion-modified substrate.

Embodiment 2 is the energy providing device of embodiment 1, wherein the charged compound modified substrate or zwitterion-modified substrate comprises a compound that has the structure of Formula I:

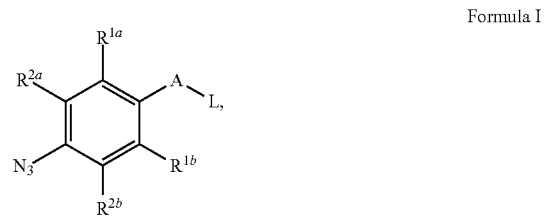

Formula I wherein
A is selected from —C(=O)— and —(SO$_2$)—;
L is selected from —OQ, —O⁻, —N⁺R³HQ and —NR³Q;

Q is a structure represented by a formula:

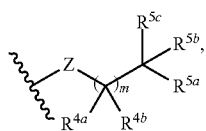

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of R$^{1a}$ and R$^{1b}$ is independently selected from hydrogen and halogen;
each of R$^{2a}$ and R$^{2b}$ is halogen;
R$^3$, when present, is selected from hydrogen and C1-C4 alkyl;
each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;
each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;
each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;
R$^7$, when present, is selected from hydrogen and C1-C4 alkyl;
each of R$^{8a}$ and R$^{8b}$, when present, is independently selected from hydrogen and C1-C4 alkyl;
R$^9$, when present, is selected from hydrogen and C1-C4 alkyl;
each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;
R$^{11}$, when present, is selected from hydrogen and C1-C4 alkyl;
each of R$^{12a}$ and R$^{12b}$, when present, is independently selected from hydrogen and C1-C4 alkyl;
R$^{13}$, when present, is selected from hydrogen and C1-C4 alkyl, and
provided that the compound is charged or zwitterionic.

Embodiment 3 is the energy providing device of embodiment 2, wherein the compound has a structure selected from:

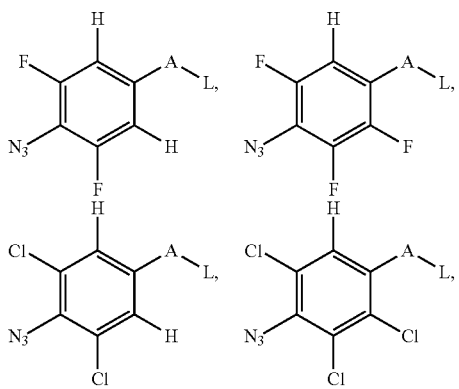

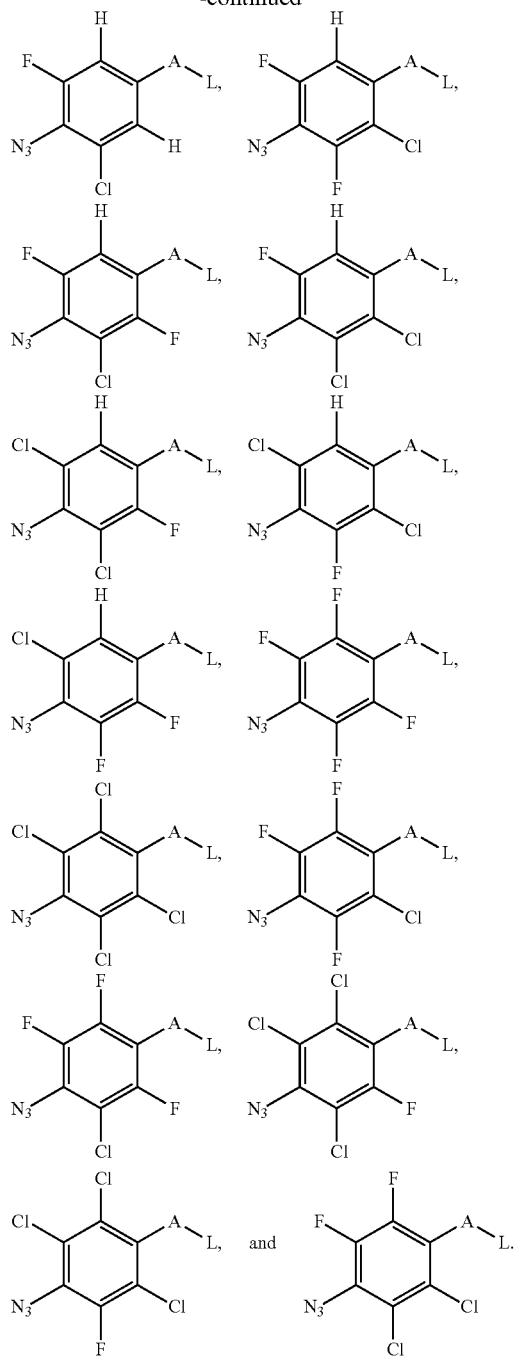

Embodiment 4 is the energy providing device of embodiments 2 or 3, wherein the compound has a structure selected from:

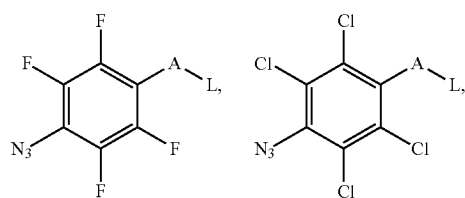

-continued

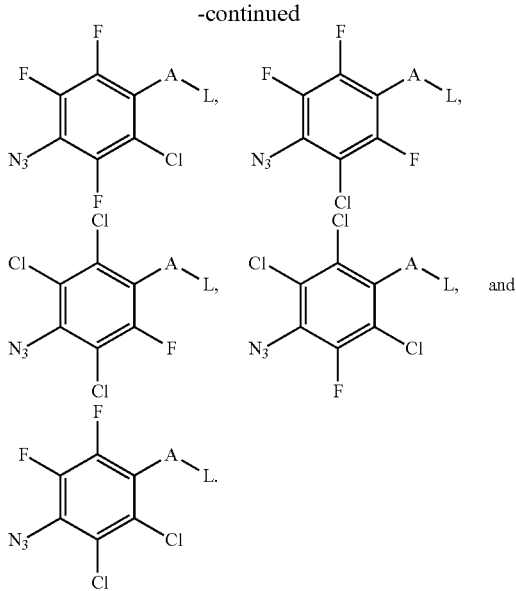

Embodiment 5 is the energy providing device of any one of embodiments 2-4, wherein the compound has the following structure:

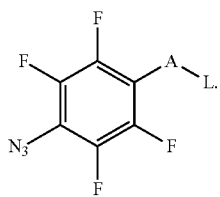

Embodiment 6 is the energy providing device of embodiment 2, wherein the compound has the structure selected from:

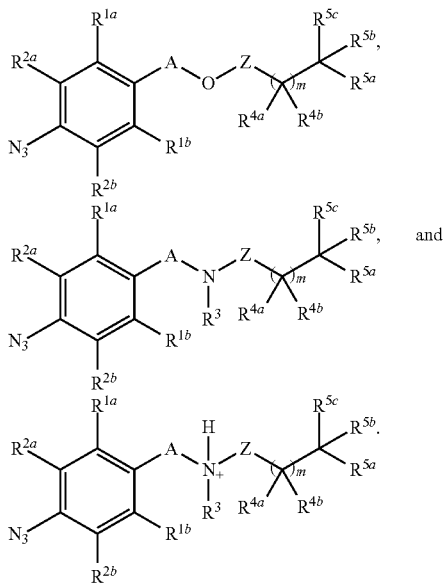

Embodiment 7 is the energy providing device of embodiment 2, wherein the compound has the following structure:

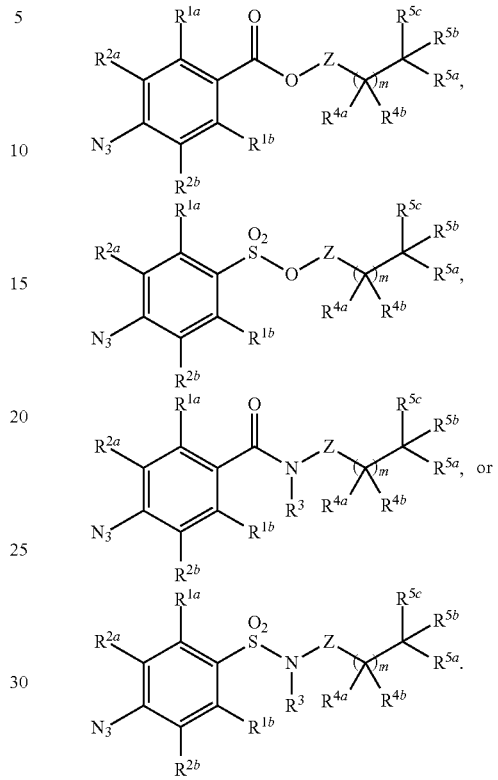

Embodiment 8 is the energy providing device of embodiments 6 or 7, wherein R1a, R1b, R2a, and $R^{2b}$ are each —F.

Embodiment 9 is the energy providing device of embodiments 2-8, wherein Q is selected from:

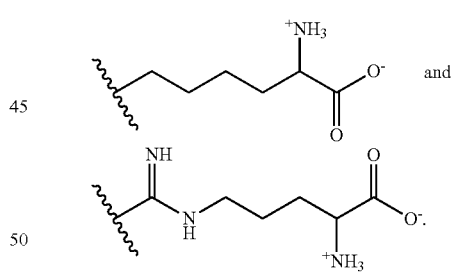

Embodiment 10 is the energy providing device of embodiments 2-8, wherein Q is:

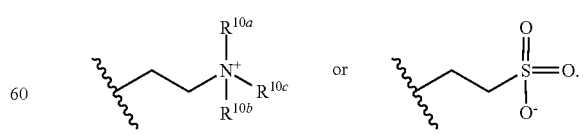

Embodiment 11 is the energy providing device of any one of embodiments 2-8, wherein Z is —$CR^{6a}R^{6b}$—.

Embodiment 12 is the energy providing device of embodiment 11, wherein $R^{6a}$ and $R^{6b}$ are each hydrogen.

Embodiment 13 is the energy providing device of any one of embodiments 2-8 and 11-12, wherein m is 0, 1, 2, or 3.

Embodiment 14 is the energy providing device of embodiment 13, wherein m is 0.

Embodiment 15 is The energy providing device of any one of embodiments 2-8 and 11-14, wherein $R^{5a}$ is —$NR^{10a}R^{10b}R^{10c+}$; $R^{5b}$ is hydrogen; and $R^{5c}$ is hydrogen.

Embodiment 16 is the energy providing device of embodiment 2, wherein the compound has the structure of Formula Ia:

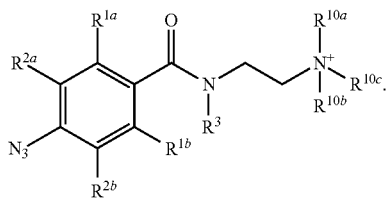

Embodiment 17 is the energy providing device of embodiment 2, wherein the compound has the structure of Formula Ib:

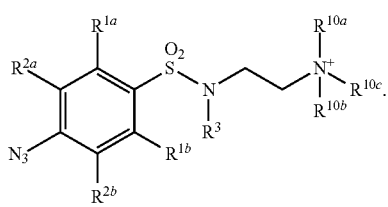

Embodiment 18 is the energy providing device of embodiments 16 or 17, wherein $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$.

Embodiment 19 is the energy providing device of any one of embodiments 16-18, wherein $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$.

Embodiment 20 is the energy providing device of embodiments 16-19, wherein $R^{10a}$ and $R^{10b}$ are each C1-C4alkyl.

Embodiment 21 is the energy providing device of embodiment 20, wherein $R^{10a}$ and $R^{10b}$ are each methyl.

Embodiment 22 is the energy providing device of any one of embodiments 16-21, wherein $R^3$ is hydrogen.

Embodiment 23 is the energy providing device of embodiment 16, wherein the zwitterionic compound is

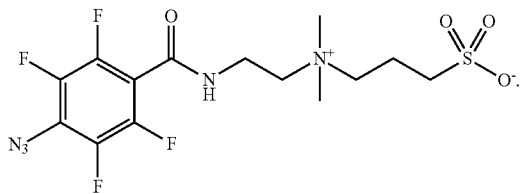

Embodiment 24 is the energy providing device of embodiment 16, wherein the charged compound is

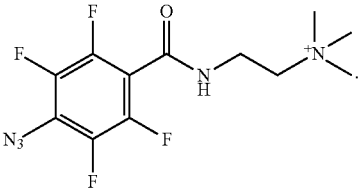

Embodiment 25 is the energy providing device of embodiment 10, wherein the charged compound is

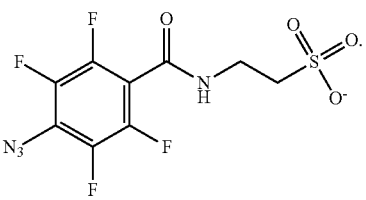 [SMILES: [N-]=[N+]=Nc1c(F)c(F)c(C(=O)NCCS(=O)(=O)[O-])c(F)c1F]

Embodiment 26 is the energy providing device of embodiment 17, wherein the zwitterionic compound is

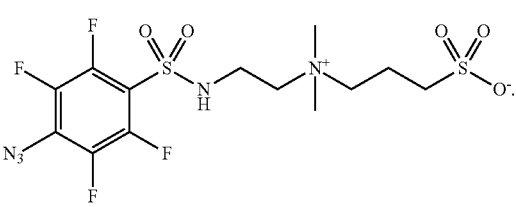

Embodiment 27 is the energy providing device of embodiment 17, wherein the charged compound is

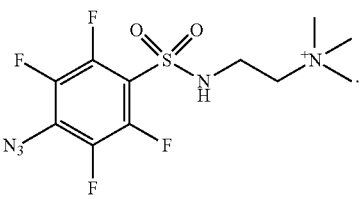 [SMILES: C[N+](C)(C)CCNS(=O)(=O)c1c(F)c(F)c(N=[N+]=[N-])c(F)c1F]

Embodiment 28 is the energy providing device of embodiment 10, wherein the charged compound is

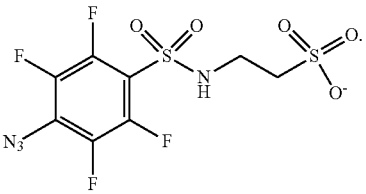 [SMILES: [N-]=[N+]=Nc1c(F)c(F)c(S(=O)(=O)NCCS(=O)(=O)[O-])c(F)c1F]

Embodiment 29 is the energy providing device of embodiment 2, wherein the charged compound is

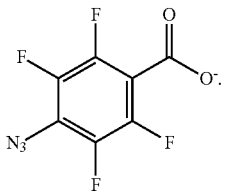

Embodiment 30 is the energy providing device of embodiment 2, wherein the charged compound is

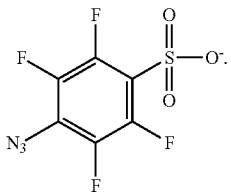

Embodiment 31 is the energy providing device of embodiment 1 or 2, wherein the substrate comprises a separator.

Embodiment 32 is the energy providing device of embodiment 31, wherein the separator comprises a polymer-based separator.

Embodiment 33 is the energy providing device of embodiment 32, wherein the polymer-based separator comprises a polyolefinic separator.

Embodiment 34 is the energy providing device of embodiment 33, wherein the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof.

Embodiment 35 is the energy providing device of any one of the embodiments 31-34, wherein the separator comprises a microporous separator, a nonwoven separator, an ion-exchange membrane, a supported liquid membrane, or a solid ion conductor.

Embodiment 36 is the energy providing device of embodiment 1 or 2, wherein the substrate comprises a carbon-based substrate containing a moiety capable of binding with a compound that has a structure of Formula I.

Embodiment 37 is the energy providing device of embodiment 36, wherein the carbon-based substrate comprises a polymer moiety.

Embodiment 38 is the energy providing device of embodiment 37, wherein the carbon-based substrate comprises a polyolefin moiety.

Embodiment 39 is the energy providing device of embodiment 38, wherein the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

Embodiment 40 is the energy providing device of embodiment 1 or 2, further comprising an electrolyte disposed onto the charged compound modified substrate or zwitterion modified substrate.

Embodiment 41 is the energy providing device of embodiment 40, wherein the electrolyte is a polar electrolyte.

Embodiment 42 is the energy providing device of embodiment 40 or 41, wherein the electrolyte comprises a carbonate-based electrolyte.

Embodiment 43 is the energy providing device of any one of the embodiments 40-42, wherein the electrolyte comprises ethylene carbonate and propylene carbonate.

Embodiment 44 is the energy providing device of any one of the embodiments 40-43, wherein the electrolyte is an aqueous electrolyte.

Embodiment 45 is the energy providing device of embodiment 1 or 2, further comprising an electrode.

Embodiment 46 is the energy providing device of embodiment 45, wherein the electrode is a carbon-based electrode.

Embodiment 47 is the energy providing device of embodiment 46, wherein the carbon-based electrode is a carbon-based substrate.

Embodiment 48 is the energy providing device of embodiment 46 or 47, wherein the graphene-based electrode comprises a porous graphene matrices.

Embodiment 49 is the energy providing device of embodiment 48, wherein the porous graphene matrices comprises a three-dimensional intercalated network of single or multiple layers of graphene sheets.

Embodiment 50 is the energy providing device of embodiment 48 or 49, wherein the graphene-based electrode comprises a corrugated carbon-carbon network.

Embodiment 51 is the energy providing device of any one of the embodiments 48-50, wherein a compound that has a structure of Formula I is further deposited on the corrugated carbon-carbon network.

Embodiment 52 is the energy providing device of embodiment 45, wherein the electrode is an anode.

Embodiment 53 is the energy providing device of embodiment 45, wherein the electrode is a cathode.

Embodiment 54 is the energy providing device of any one of the embodiments 1-53, wherein the energy providing device comprises a battery, a supercapacitor, or a fuel cell.

Embodiment 55 is the energy providing device of any one of the embodiments 1-54, wherein the energy providing device is a battery.

Embodiment 56 is the energy providing device of embodiment 55, wherein the battery comprises a primary cell or a secondary cell.

Embodiment 57 is the energy providing device of embodiment 55 or 56, wherein the battery comprises a lead acid cell, NiCad cell, NiMH cell, NaNiCl cell, Lithium Ion cell, Nickel Iron cell, Nickel Zinc cell, silver oxide, nickel hydrogen, or lithium polymer cell.

Embodiment 58 is the energy providing device of any one of the embodiments 55-57, wherein the battery comprises an ampoule battery, a flow battery, or a water activated battery.

Embodiment 59 is the energy providing device of any one of the embodiments 1-54, wherein the energy providing device is a supercapacitor.

Embodiment 60 is the energy providing device of embodiment 59, wherein the supercapacitor comprises an electrochemical double-layer capacitor (EDLC), a pseudocapacitor, or a hybrid supercapacitor.

Embodiment 61 is the energy providing device of any one of the embodiments 1-54, wherein the energy providing device is a fuel cell.

Embodiment 62 is the energy providing device of any one of the embodiments 1-61, wherein the energy providing device has a lower internal resistance relative to an equivalent energy providing device without the charged compound modified substrate or zwitterion modified substrate.

Embodiment 63 is the energy providing device of any one of the embodiments 1-62, wherein the energy providing device has an increased electrolyte uptake relative to an equivalent energy providing device without the charged compound modified substrate or zwitterion modified substrate.

Embodiment 64 is the energy providing device of any one of the embodiments 1-63, wherein the energy providing device has an increased charge transfer relative to an equivalent energy providing device without the charged compound modified substrate or zwitterion modified substrate.

Embodiment 65 is the energy providing device of embodiment 64, wherein the charge transfer is between an anode and a cathode.

Embodiment 66 is the energy providing device of embodiment 64, wherein the charge transfer is between an electrode and an electrolyte.

Embodiment 67 is the energy providing device of any one of the embodiments 1-66, wherein the energy providing device has an increased capacitance relative to an equivalent energy providing device without the charged compound modified substrate or zwitterion modified substrate.

An energy providing device comprising:
an electrolyte comprising a perhalogenatedphenyl azide charged or zwitterion compound,
wherein the perhalogenatedphenyl azide charged or zwitterion compound has the structure of Formula I:

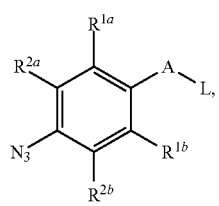

Formula I wherein
A is selected from —C(=O)— and —(SO$_2$)—;
L is selected from —OQ, —O$^-$, —N$^+$R$^3$HQ and —NR$^3$Q;
Q is a structure represented by a formula:

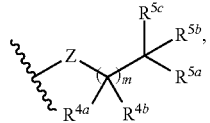

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of R$^{1a}$ and R$^{1b}$ is halogen;
each of R$^{2a}$ and R$^{2b}$ is halogen;
R$^3$, when present, is selected from hydrogen and C1-C4 alkyl;
each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;

each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;

each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;

R$^7$, when present, is selected from hydrogen and C1-C4 alkyl;

each of R$^{8a}$ and R$^{8b}$, when present, is independently selected from hydrogen and C1-C4 alkyl;

R$^9$, when present, is selected from hydrogen and C1-C4 alkyl;

each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;

R$^{11}$, when present, is selected from hydrogen and C1-C4 alkyl;

each of R$^{12a}$ and R$^{12b}$, when present, is independently selected from hydrogen and C1-C4 alkyl;

R$^{13}$, when present, is selected from hydrogen and C1-C4 alkyl, and provided that the compound is charged or zwitterionic.

Embodiment 69 is the energy providing device of embodiment 68, wherein the compound has a structure selected from:

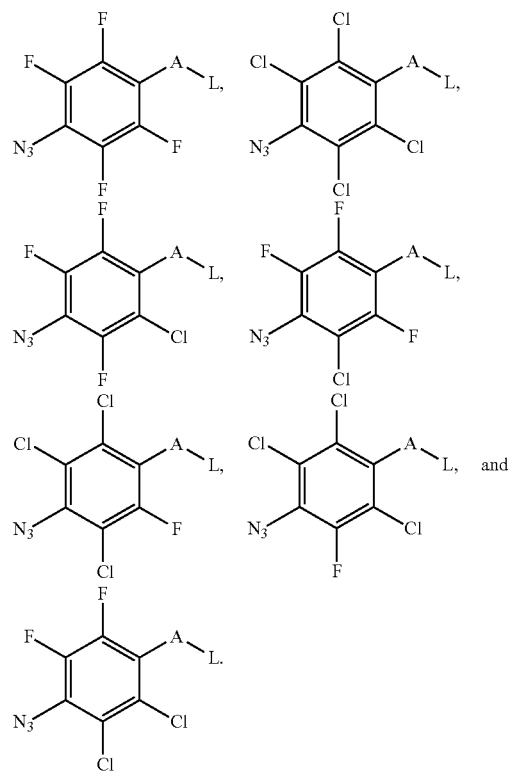

Embodiment 70 is the energy providing device of embodiments 68 or 69, wherein the compound has the following structure:

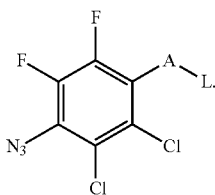

Embodiment 71 is the energy providing device of embodiment 68, wherein the compound has the structure selected from:

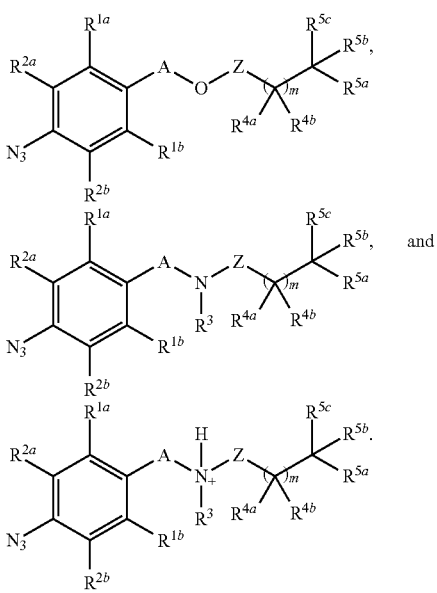

Embodiment 72 is the energy providing device of embodiment 68, wherein the compound has the following structure:

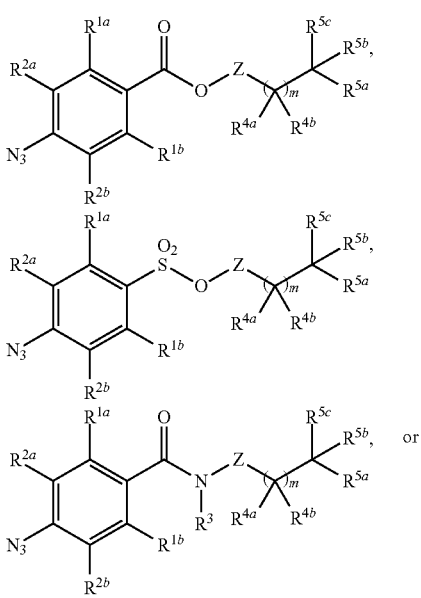

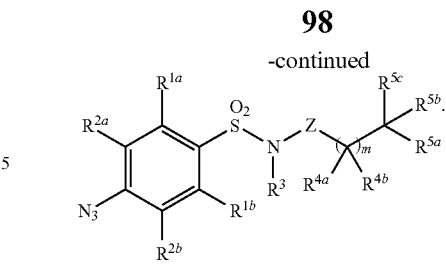

Embodiment 73 is the energy providing device of embodiments 71 or 72, wherein $R^{1a}$, $R^{1b}$, $R^{2a}$, and $R^{2b}$ are each —F.

Embodiment 74 is the energy providing device of embodiments 68-73, wherein Q is selected from:

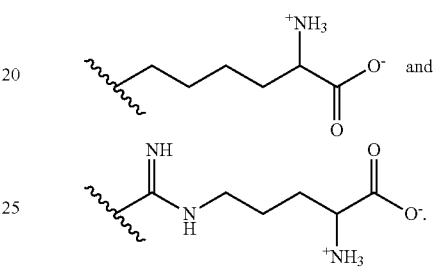

Embodiment 75 is the energy providing device of embodiments 68-73, wherein Q is:

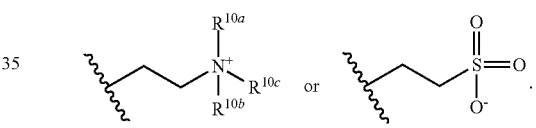

Embodiment 76 is the energy providing device of any one of embodiments 68-73, wherein Z is —$CR^{6a}R^{6b}$—.

Embodiment 77 is the energy providing device of embodiment 76, wherein $R^{6a}$ and $R^{6b}$ are each hydrogen.

Embodiment 78 is the energy providing device of any one of embodiments 68-73 and 76-77, wherein m is 0, 1, 2, or 3.

Embodiment 79 is the energy providing device of embodiment 78, wherein m is 0.

Embodiment 80 is the energy providing device of any one of embodiments 68-73 and 76-79, wherein $R^{5a}$ is —$NR^{10a}R^{10b}R^{10c+}$; $R^{5b}$ is hydrogen; and $R^{5c}$ is hydrogen.

Embodiment 81 is the energy providing device of embodiment 68, wherein the compound has the structure of Formula Ia:

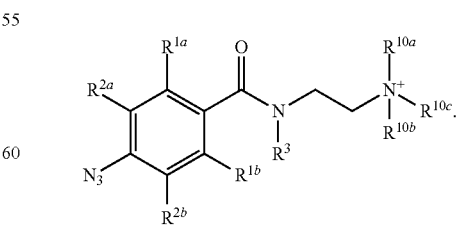

Embodiment 82 is the energy providing device of embodiment 68, wherein the compound has the structure of Formula Ib:

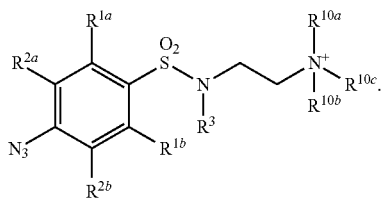

Embodiment 83 is the energy providing device of embodiments 81 or 82, wherein $R^{10c}$ is —(C1-C8alkylene)SO$_3^-$, —(C1-C8alkylene)SO$_3$H, —(C1-C8alkylene)CO$_2^-$, or —(C1-C8alkylene)CO$_2$H.

Embodiment 84 is the energy providing device of embodiments any one of embodiments 81-83 wherein $R^{10c}$ is —CH$_2$CH$_2$CH$_2$—SO$_3^-$, —CH$_2$CH$_2$CH$_2$—SO$_3$H, —CH$_2$CH$_2$CH$_2$—CO$_2^-$, or —CH$_2$CH$_2$CH$_2$—CO$_2$H.

Embodiment 85 is the energy providing device of any one of embodiments 81-84, wherein $R^{10a}$ and $R^{10b}$ are each C1-C4alkyl.

Embodiment 86 is the energy providing device of embodiment 85, wherein $R^{10a}$ and $R^{10b}$ are each methyl.

Embodiment 87 is the energy providing device of any one of embodiments 81-86, wherein $R^3$ is hydrogen.

Embodiment 88 is the energy providing device of embodiment 81, wherein the zwitterionic compound is

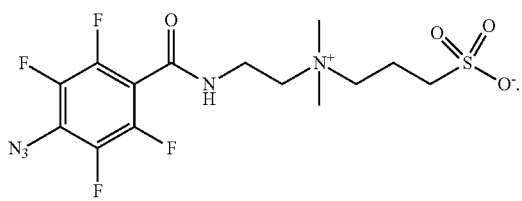

Embodiment 89 is the energy providing device of embodiment 81, wherein the charged compound is

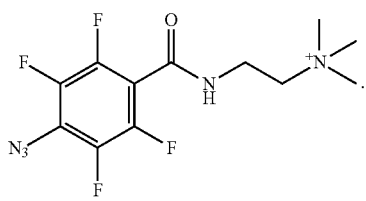

Embodiment 90 is the energy providing device of embodiment 75, wherein the charged compound is

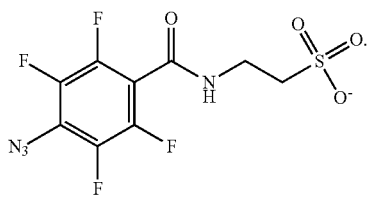

Embodiment 91 is the energy providing device of embodiment 82, wherein the zwitterionic compound is

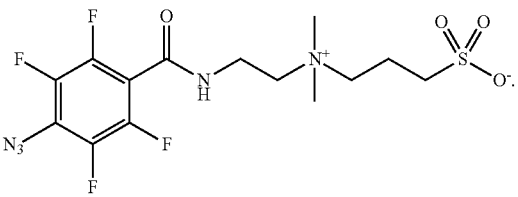

Embodiment 92 is the energy providing device of embodiment 82, wherein the charged compound is

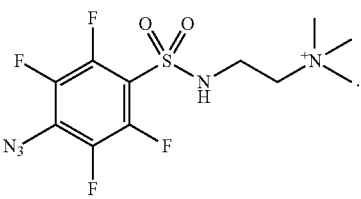

Embodiment 93 is the energy providing device of embodiment 75, wherein the charged compound is

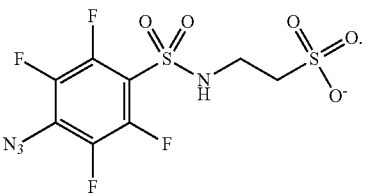 [SMILES: [N-]=[N+]=Nc1c(F)c(F)c(S(=O)(=O)NCCS(=O)(=O)[O-])c(F)c1F]

Embodiment 94 is the energy providing device of embodiment 68, wherein the charged compound is

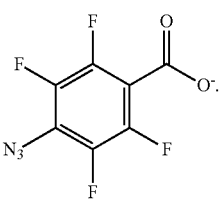

Embodiment 95 is the energy providing device of embodiment 68, wherein the charged compound is

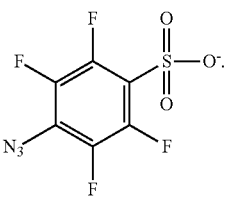

Embodiment 96 is the energy providing device of embodiment 68, wherein the electrolyte is a polar electrolyte.

Embodiment 97 is the energy providing device of embodiment 68 or 96, wherein the electrolyte comprises a carbonate-based electrolyte.

Embodiment 98 is the energy providing device of any one of the embodiments 68, 96, or 97, wherein the electrolyte comprises ethylene carbonate and propylene carbonate.

Embodiment 99 is the energy providing device of any one of the embodiments 68 or 96-98, wherein the electrolyte is an aqueous electrolyte.

Embodiment 100 is the energy providing device of embodiment 68, wherein the energy providing device further comprises a separator and an electrode.

Embodiment 101 is the energy providing device of embodiment 100, wherein the separator comprises a polymer-based separator.

Embodiment 102 is the energy providing device of embodiment 101, wherein the polymer-based separator comprises a polyolefinic separator.

Embodiment 103 is the energy providing device of embodiment 102, wherein the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof.

Embodiment 104 is the energy providing device of any one of the embodiments 100-101, wherein the separator comprises a microporous separator, a nonwoven separator, an ion-exchange membrane, a supported liquid membrane, or a solid ion conductor.

Embodiment 105 is the energy providing device of embodiment 100, wherein the electrode is a carbon-based electrode.

Embodiment 106 is the energy providing device of embodiment 105, wherein the carbon-based electrode is a graphene-based electrode.

Embodiment 107 is the energy providing device of embodiment 106, wherein the graphene-based electrode comprises a porous graphene matrices.

Embodiment 108 is the energy providing device of embodiment 107, wherein the porous graphene matrices comprises a three-dimensional intercalated network of single or multiple layers of graphene sheets.

Embodiment 109 is the energy providing device of embodiment 107 or 108, wherein the graphene-based electrode comprises a corrugated carbon-carbon network.

Embodiment 110 is the energy providing device of embodiment 109, wherein the electrolyte comprising a perhalogenatedphenyl azide charged or zwitterion compound is further deposited on the corrugated carbon-carbon network.

Embodiment 111 is the energy providing device of embodiment 100, wherein the electrode is an anode.

Embodiment 112 is the energy providing device of embodiment 100, wherein the electrode is a cathode.

Embodiment 113 is the energy providing device of any one of the embodiments 68-112, wherein the energy providing device comprises a battery, a supercapacitor, or a fuel cell.

Embodiment 114 is the energy providing device of any one of the embodiments 68-113, wherein the energy providing device is a battery.

Embodiment 115 is the energy providing device of embodiment 113 or 114, wherein the battery comprises a primary cell or a secondary cell.

Embodiment 116 is the energy providing device of any one of the embodiments 113-115, wherein the battery comprises a lead acid cell, NiCad cell, NiMH cell, NaNiCl cell, Lithium Ion cell, Nickel Iron cell, Nickel Zinc cell, silver oxide, nickel hydrogen, or lithium polymer cell.

Embodiment 117 is the energy providing device of any one of the embodiments 113-116, wherein the battery comprises an ampoule battery, a flow battery, or a water activated battery.

Embodiment 118 is the energy providing device of any one of the embodiments 68-113, wherein the energy providing device is a supercapacitor.

Embodiment 119 is the energy providing device of embodiment 118, wherein the supercapacitor comprises an electrochemical double-layer capacitor (EDLC), a pseudocapacitor, or a hybrid supercapacitor.

Embodiment 120 is the energy providing device of any one of the embodiments 68-113, wherein the energy providing device is a fuel cell.

Embodiment 121 is a method of preparing a charged compound modified substrate or zwitterion modified substrate comprising:
  a) incubating the substrate with a solution comprising a charged or zwitterion compound for at least 40 minutes; and
  b) exposing the treated substrate of step a) under a light source for at least one minute, thereby generating the charged compound modified substrate or zwitterion modified substrate.

Embodiment 122 is the method of embodiment 121, wherein the incubating of step a) is for at least 45 minutes, at least 50 minutes, at least 55 minutes, at least 60 minutes, at least 65 minutes, at least 70 minutes, at least 80 minutes, at least 90 minutes, or at least 120 minutes.

Embodiment 123 is the method of embodiment 121, wherein the incubating of step a) further comprises heating the substrate with the charged or zwitterion compound at a temperature of between 45° C. and 80° C., between 45° C. and 70° C., between 45° C. and 65° C., between 45° C. and 60° C., between 45° C. and 55° C., between 45° C. and 50° C., between 50° C. and 80° C., between 50° C. and 70° C., between 50° C. and 60° C., between 55° C. and 80° C., between 55° C. and 70° C., between 55° C. and 60° C., between 60° C. and 80° C. or between 60° C. and 70° C.

Embodiment 124 is the method of embodiment 121, wherein the incubating of step a) further comprises heating the substrate with the charged or zwitterion compound at a temperature of at least 45° C., 50° C., 55° C., 60° C., 65° C., 70° C., 75° C. or 80° C.

Embodiment 125 is the method of embodiment 121, wherein the exposing of step b) under a light source is for at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 126 is the method of embodiment 121 or 125, wherein the light source is an ultraviolet light source.

Embodiment 127 is the method of embodiment 126, wherein the ultraviolet light source has an intensity of at least 900 µW/cm$^2$.

Embodiment 128 is the method of embodiment 126 or 127, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 129 is the method of embodiment 126 or 127, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 130 is the method of embodiment 121, wherein the solution of step a) is a first water-alcohol solution.

Embodiment 131 is the method of embodiment 130, wherein the first water-alcohol solution comprises a water to alcohol ratio of about 90:10, 80:20, 70:30, 60:40, 50:50, 40:60, 33:67, 30:70, 20:80 or 10:90.

Embodiment 132 is the method of embodiment 131, wherein the alcohol comprises methanol, ethanol, 1-propanol, 2-propanol, 2-methyl-2-propanol, 3-methyl-1-butanol, 2,2-dimethyl-1-propanol, cyclopentanol, 1-hexanol, or cyclohexanol.

Embodiment 133 is the method of embodiment 121, wherein the charged or zwitterion compound is a compound that has the structure of Formula I:

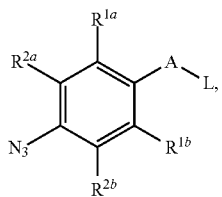

Formula I wherein
A is selected from —C(=O)— and —(SO$_2$)—;
L is selected from —OQ, —O$^-$, —N$^+$R$^3$HQ and —NR$^3$Q;
Q is a structure represented by a formula:

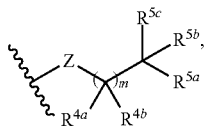

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of R$^{1a}$ and R$^{1b}$ is independently selected from hydrogen and halogen;
each of R$^{2a}$ and R$^{2b}$ is halogen;
R$^3$, when present, is selected from hydrogen and C1-C4 alkyl;
  each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;
  each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;

each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;

R$^7$, when present, is selected from hydrogen and C1-C4 alkyl;

each of R$^{8a}$ and R$^{8b}$, when present, is independently selected from hydrogen and C1-C4 alkyl;

R$^9$, when present, is selected from hydrogen and C1-C4 alkyl;

each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;

R$^{11}$, when present, is selected from hydrogen and C1-C4 alkyl;

each of R$^{12a}$ and R$^{12b}$, when present, is independently selected from hydrogen and C1-C4 alkyl;

R$^{13}$, when present, is selected from hydrogen and C1-C4 alkyl, and provided that the compound is charged or zwitterionic.

Embodiment 134 is the method of embodiment 133, wherein the compound has a structure selected from:

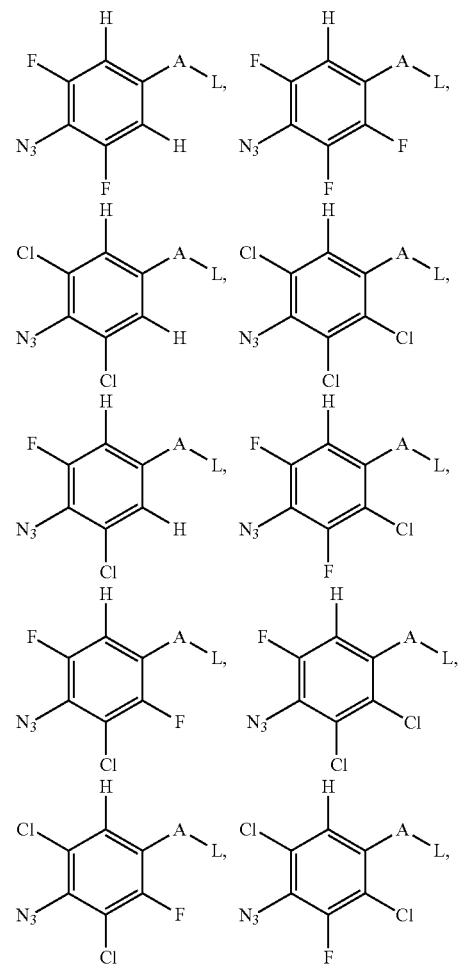

-continued

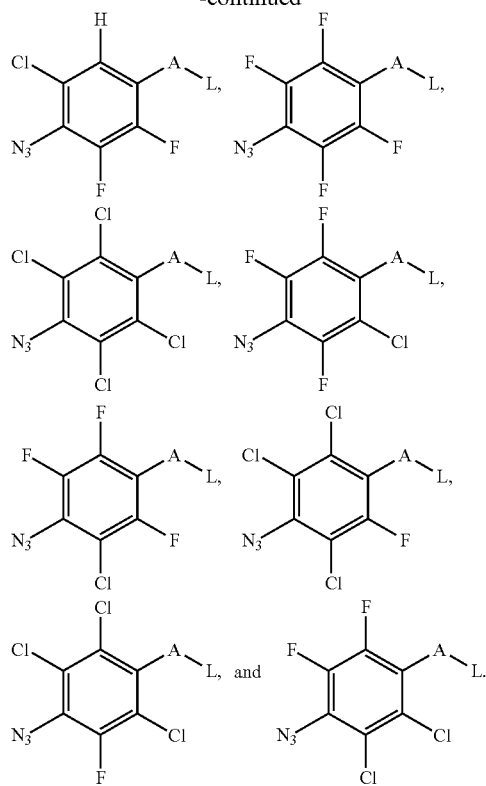

Embodiment 135 is the method of embodiments 133 or 134, wherein the compound has a structure selected from:

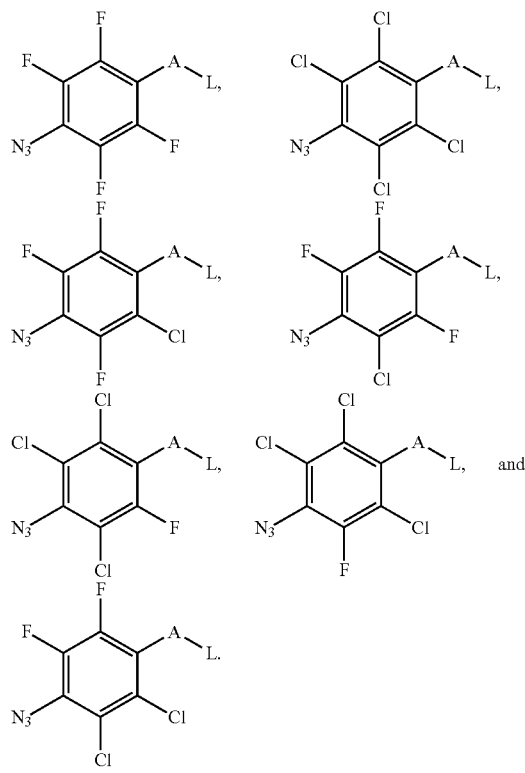

Embodiment 136 is the method of any one of embodiments 133-135, wherein the compound has the following structure:

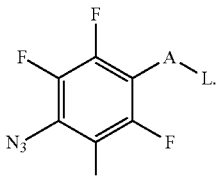

Embodiment 137 is the method of embodiment 133, wherein the compound has the structure selected from:

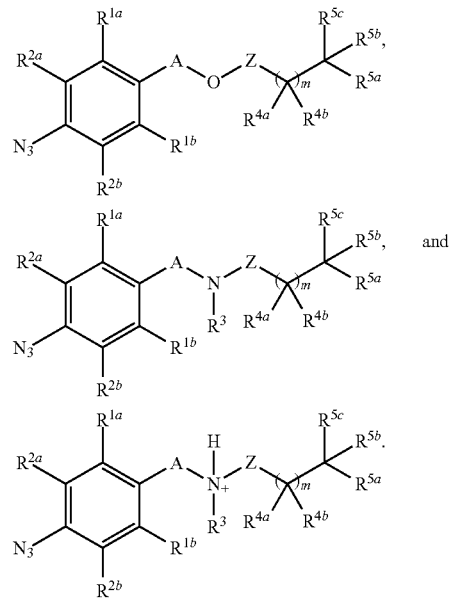

Embodiment 138 is the method of embodiment 133, wherein the compound has the following structure:

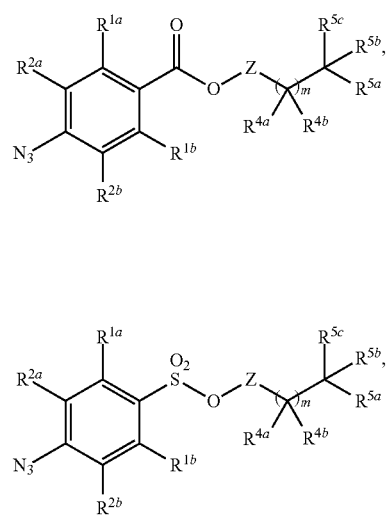

-continued

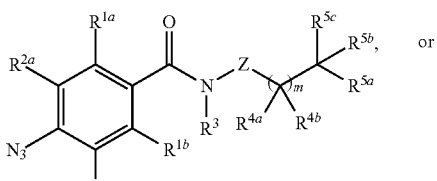

Embodiment 139 is the method of embodiments 137 or 138, wherein $R^{1a}$, $R^{1b}$, $R^{2a}$, and $R^{2b}$ are each —F.

Embodiment 140 is the method of embodiments 133-139, wherein Q is selected from:

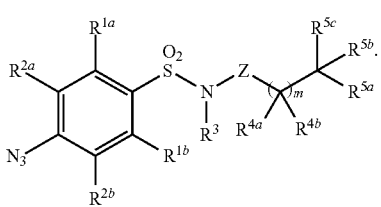

Embodiment 141 is the method of embodiments 133-139, wherein Q is:

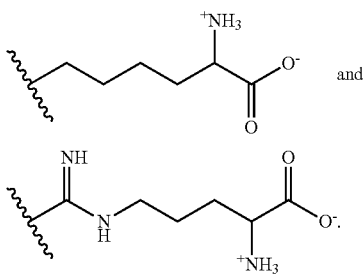

Embodiment 142 is the method of any one of embodiments 133-139, wherein Z is —$CR^{6a}R^{6b}$—.

Embodiment 143 is the method of embodiment 142, wherein $R^{6a}$ and $R^{6b}$ are each hydrogen.

Embodiment 144 is the method of any one of embodiments 133-139 and 142-143, wherein m is 0, 1, 2, or 3.

Embodiment 145 is the method of embodiment 144, wherein m is 0.

Embodiment 146 is the method of any one of embodiments 133-127 and 142-144, wherein $R^{5a}$ is —$NR^{10a}R^{10b}R^{10c+}$; $R^{5b}$ is hydrogen; and $R^{5c}$ is hydrogen.

Embodiment 147 is the method of embodiment 133, wherein the compound has the structure of Formula Ia:

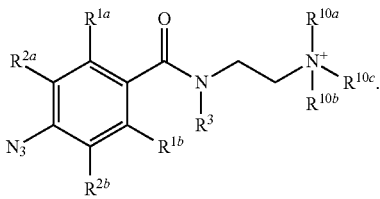

Embodiment 148 is the method of embodiment 133, wherein the compound has the structure of Formula Ib:

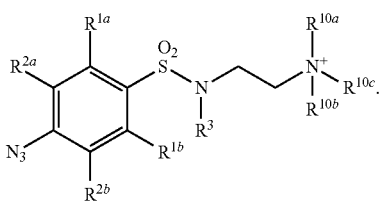

Embodiment 149 is the method of embodiments 147 or 148, wherein $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$.

Embodiment 150 is the method of any one of embodiments 147-149, wherein $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$.

Embodiment 151 is the method of any one of embodiments 147-150, wherein $R^{10a}$ and $R^{10b}$ are each C1-C4alkyl.

Embodiment 152 is the method of embodiment 151, wherein $R^{10a}$ and $R^{10b}$ are each methyl.

Embodiment 153 is the method of any one of embodiments 147-152, wherein $R^3$ is hydrogen.

Embodiment 154 is the method of embodiment 147, wherein the zwitterionic compound is

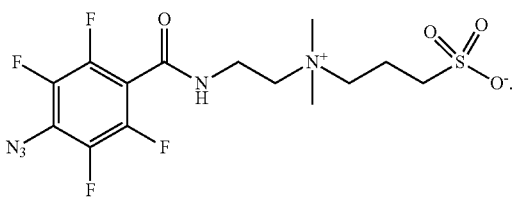

Embodiment 155 is the method of embodiment 147, wherein the charged compound is

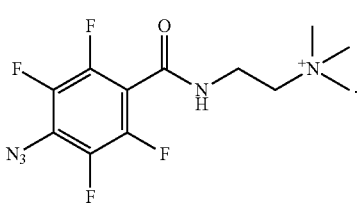 [SMILES: C[N+](C)(C)CCNC(=O)c1c(F)c(F)c(N=[N+]=[N-])c(F)c1F]

Embodiment 156 is the method of embodiment 141, wherein the charged compound is

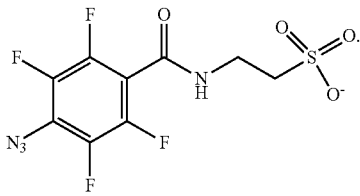 [SMILES: [N-]=[N+]=Nc1c(F)c(F)c(C(=O)NCCS(=O)(=O)[O-])c(F)c1F]

Embodiment 157 is the method of embodiment 148, wherein the zwitterionic compound is

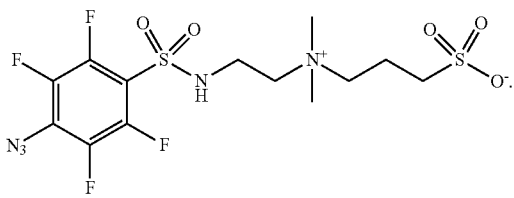

Embodiment 158 is the method of embodiment 148, wherein the charged compound is

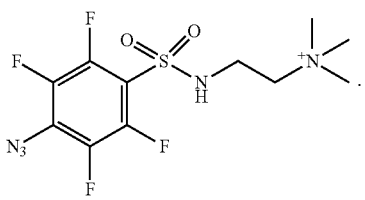 [SMILES: C[N+](C)(C)CCNS(=O)(=O)c1c(F)c(F)c(N=[N+]=[N-])c(F)c1F]

Embodiment 159 is the method of embodiment 141, wherein the charged compound is

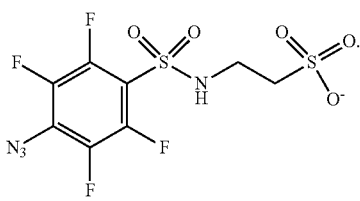 [SMILES: [N-]=[N+]=Nc1c(F)c(F)c(S(=O)(=O)NCCS(=O)(=O)[O-])c(F)c1F]

Embodiment 160 is the method of embodiment 133, wherein the charged compound is

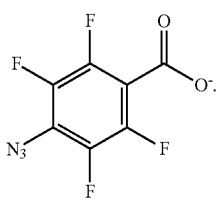

Embodiment 161 is the method of embodiment 133, wherein the charged compound is

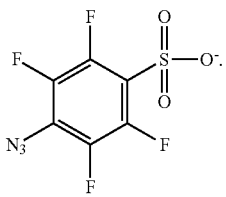

Embodiment 162 is the method of any one of the embodiments 121 or 133-161, wherein the concentration of the charged or zwitterion compound in the solution is between 1 mM and 10 mM, between 1 mM and 9 mM, between 1 mM and 8 mM, between 1 mM and 7 mM, between 1 mM and 6 mM, between 1 mM and 5 mM, between 1 mM and 4 mM, between 1 mM and 3 mM, between 1 mM and 2 mM, between 1.5 mM and 10 mM, between 1.5 mM and 9 mM, between 1.5 mM and 8 mM, between 1.5 mM and 7 mM, between 1.5 mM and 6 mM, between 1.5 mM and 5 mM, between 1.5 mM and 4 mM, between 1.5 mM and 3 mM, between 1.5 mM and 2 mM, between 2 mM and 10 mM, between 2 mM and 9 mM, between 2 mM and 8 mM, between 2 mM and 7 mM, between 2 mM and 6 mM, between 2 mM and 5 mM, between 2 mM and 4 mM, between 2 mM and 3 mM, between 3 mM and 10 mM, between 3 mM and 8 mM, between 3 mM and 6 mM, between 4 mM and 10 mM, between 4 mM and 8 mM, between 4 mM and 6 mM, between 5 mM and 10 mM, between 5 mM and 8 mM, between 6 mM and 10 mM, or between 8 mM and 10 mM.

Embodiment 163 is the method of any one of the embodiments 121 or 133-161, wherein the concentration of the charged or zwitterion compound in the solution is about 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, 5 mM, 6 mM, 7 mM, 8 mM, 9 mM, or 10 mM.

Embodiment 164 is the method of embodiment 162 or 163, wherein the concentration of the charged or zwitterion compound is between 0.1 to 1 mL per square centimeter of the substrate.

Embodiment 165 is the method of any one of the embodiments 121 or 133-161, further comprising incubating the charged compound modified substrate or zwitterion modified substrate in a second water-alcohol solution after exposure with the light source.

Embodiment 166 is the method of embodiment 165, wherein the second water-alcohol solution comprises a water to alcohol ratio of about 90:10, 80:20, 70:30, 60:40, 50:50, 40:60, 33:67, 30:70, 20:80 or 10:90.

Embodiment 167 is the method of embodiment 166, wherein the alcohol comprises methanol, ethanol, 1-propanol, 2-propanol, 2-methyl-2-propanol, 3-methyl-1-butanol, 2,2-dimethyl-1-propanol, cyclopentanol, 1-hexanol or cyclohexanol.

Embodiment 168 is the method of embodiment 165, wherein the incubating further comprises sonicating the charged compound modified substrate or zwitterion modified substrate in the second water-alcohol solution.

Embodiment 169 is the method of embodiment 168, wherein the sonication is for at least 1 minutes, 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 170 is the method of embodiment 165, further comprising drying the charged compound modified substrate or zwitterion modified substrate under vacuum after incubation in the second water-alcohol solution.

Embodiment 171 is the method of embodiment 121, wherein the zwitterion compound comprises:

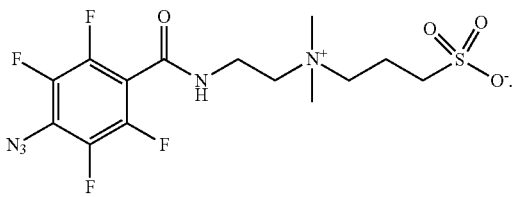

Embodiment 172 is the method of embodiment 121, wherein the charged compound comprises:

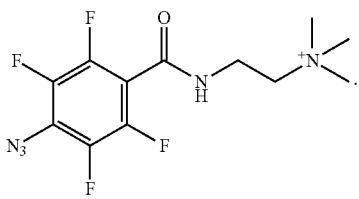 [SMILES: C[N+](C)(C)CCNC(=O)c1c(F)c(F)c(N=[N+]=[N-])c(F)c1F]

Embodiment 173 is the method of embodiment 121, wherein the charged compound comprises:

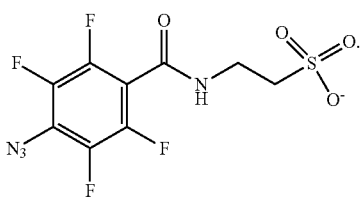 [SMILES: [N-]=[N+]=Nc1c(F)c(F)c(C(=O)NCCS(=O)(=O)[O-])c(F)c1F]

Embodiment 174 is the method of embodiment 121, wherein the zwitterion compound comprises

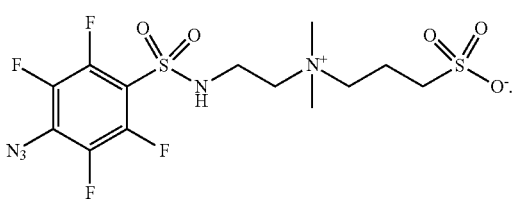

Embodiment 175 is the method of embodiment 121, wherein the charged compound comprises:

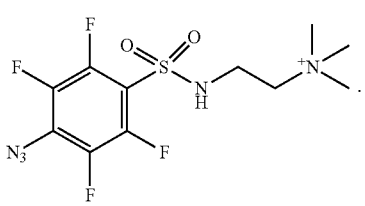 [SMILES: C[N+](C)(C)CCNS(=O)(=O)c1c(F)c(F)c(N=[N+]=[N-])c(F)c1F]

Embodiment 176 is the method of embodiment 121, wherein the charged compound comprises:

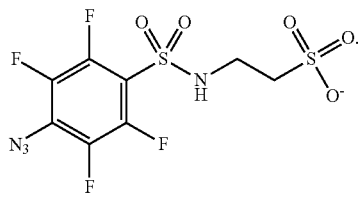 [SMILES: [N-]=[N+]=Nc1c(F)c(F)c(S(=O)(=O)NCCS(=O)(=O)[O-])c(F)c1F]

Embodiment 177 is the method of embodiment 121, wherein the charged compound comprises:

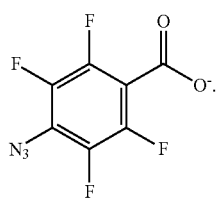

Embodiment 178 is the method of embodiment 121, wherein the charged compound comprises:

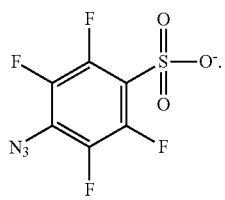

Embodiment 179 is the method of embodiment 121, wherein the substrate comprises a separator.

Embodiment 180 is the method of embodiment 179, wherein the separator comprises a polymer-based separator.

Embodiment 181 is the method of embodiment 180, wherein the polymer-based separator comprises a polyolefinic separator.

Embodiment 182 is the method of embodiment 181, wherein the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof.

Embodiment 183 is the method of any one of the embodiments 179-182, wherein the separator comprises a microporous separator, a nonwoven separator, an ion-exchange membrane, a supported liquid membrane, or a solid ion conductor.

Embodiment 184 is the method of embodiment 121, wherein the substrate comprises a carbon-based substrate containing a moiety capable of binding with the perfluorophenylazide-zwitterion derivative of Formula I.

Embodiment 185 is the method of embodiment 184, wherein the carbon-based substrate comprises a polymer moiety.

Embodiment 186 is the method of embodiment 185, wherein the carbon-based substrate comprises a polyolefin moiety.

Embodiment 187 is the method of embodiment 186, wherein the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

Embodiment 188 is a charged or zwitterionic compound that has the structure of Formula IIa:

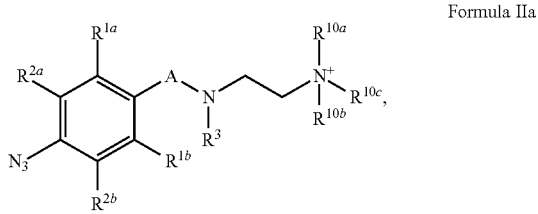

Formula IIa wherein

A is selected from —C(=O)— and —(SO$_2$)—, each of $R^{1a}$ and $R^{1b}$ is independently selected from hydrogen and halogen;

each of $R^{2a}$ and $R^{2b}$ is halogen;

$R^3$ is selected from hydrogen and C1-C4 alkyl;

$R^{10a}$ and $R^{10b}$ are independently selected from C1-C4 alkyl; and $R^{10c}$ is selected from —(C1-C8alkylene)SO$_3^-$, —(C1-C8alkylene)SO$_3$H, —(C1-C8alkylene)CO$_2^-$, and —(C1-C8alkylene)CO$_2$H.

Embodiment 189 is the compound of embodiment 188, wherein A is —(SO$_2$)—.

Embodiment 190 is the compound of embodiment 188, wherein A is —(C=O)—.

Embodiment 191 is the compound of any one of embodiments 188-190, wherein $R^{1a}$, $R^{1b}$, $R^{2a}$, and $R^{2b}$ are each independently selected from —Cl and —F.

Embodiment 192 is the compound of embodiment 191, wherein $R^{1a}$, $R^{1b}$, $R^{2a}$, and $R^{2b}$ are each —F.

Embodiment 193 is the compound of any one of embodiments 188-192, wherein $R^3$ is hydrogen.

Embodiment 194 is the compound of any one of embodiments 188-193, wherein $R^{10a}$ and $R^{10b}$ are each methyl.

Embodiment 195 is the compound of any one of embodiments 188-194, wherein $R^{10c}$ is —CH$_2$CH$_2$CH$_2$—SO$_3^-$, —CH$_2$CH$_2$CH$_2$—SO$_3$H, —CH$_2$CH$_2$CH$_2$—CO$_2^-$, or —CH$_2$CH$_2$CH$_2$—CO$_2$H.

Embodiment 196 is the compound of embodiment 195, wherein $R^{10c}$ is —CH$_2$CH$_2$CH$_2$—SO$_3^-$ or —CH$_2$CH$_2$CH$_2$—CO$_2^-$.

Embodiment 197 is the compound of embodiment 188, wherein the zwitterionic compound is

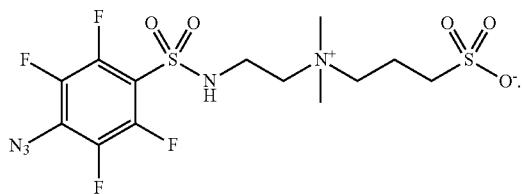

Embodiment 198 is the compound of embodiment 188, wherein the zwitterionic compound is

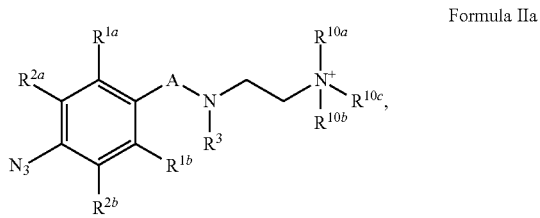

Embodiment 199 is a compound that has the structure of Formula IIa:

Formula IIa wherein

A is selected from —C(=O)— and —(SO$_2$)—;

each of $R^{1a}$ and $R^{1b}$ is independently selected from hydrogen and halogen;

each of $R^{2a}$ and $R^{2b}$ is halogen;

$R^3$ is selected from hydrogen and C1-C4 alkyl; and $R^{10a}$, $R^{10b}$, and $R^{10c}$ are independently selected from C1-C4 alkyl.

Embodiment 200 is the compound of embodiment 199, wherein A is —(SO$_2$)—.

Embodiment 201 is the compound of embodiment 199, wherein A is —(C=O)—.

Embodiment 202 is the compound of any one of embodiments 199-201, wherein $R^{1a}$, $R^{1b}$, $R^{2a}$, and $R^{2b}$ are each independently selected from —Cl and —F.

Embodiment 203 is the compound of embodiment 202, wherein $R^{1a}$, $R^{1b}$, $R^{2a}$, and $R^{2b}$ are each —F.

Embodiment 204 is the compound of any one of embodiments 199-203, wherein $R^3$ is hydrogen.

Embodiment 205 is the compound of any one of embodiments 199-204, wherein $R^{10a}$, $R^{10b}$ and $R^{10c}$ are each methyl.

Embodiment 206 is the compound of embodiment 199, wherein the charged compound is

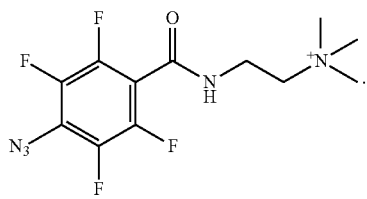

Embodiment 207 is the compound of embodiment 199, wherein the charged compound is

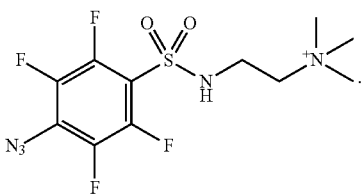

Embodiment 208 is a compound that has the structure of Formula IIb:

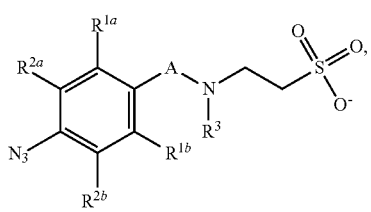

Formula IIb wherein
A is selected from —C(=O)— and —(SO$_2$)—,
each of $R^{1a}$ and $R^{1b}$ is independently selected from hydrogen and halogen;
each of $R^{2a}$ and $R^{2b}$ is halogen; and
$R^3$ is selected from hydrogen and C1-C4 alkyl.

Embodiment 209 is the compound of embodiment 208, wherein A is —(SO$_2$)—.

Embodiment 210 is the compound of embodiment 208, wherein A is —(C=O)—.

Embodiment 211 is the compound of any one of embodiments 208-210, wherein $R^{1a}$, $R^{1b}$, $R^{2a}$, and $R^{2b}$ are each independently selected from —Cl and —F.

Embodiment 212 is the compound of embodiment 211, wherein $R^{1a}$, $R^{10b}$, $R^{2a}$, and $R^{2b}$ are each —F.

Embodiment 213 is the compound of any one of embodiments 208-212, wherein $R^3$ is hydrogen.

Embodiment 214 is the compound of embodiment 208, wherein the charged compound is

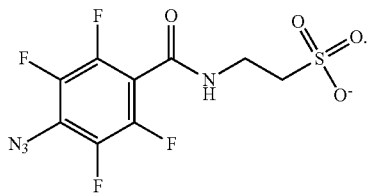 [SMILES: [N-]=[N+]=Nc1c(F)c(F)c(C(=O)NCCS(=O)(=O)[O-])c(F)c1F]

Embodiment 215 is the compound of embodiment 208, wherein the charged compound is

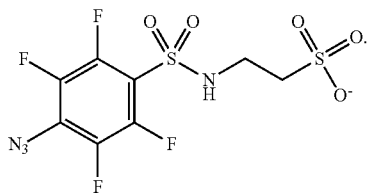 [SMILES: [N-]=[N+]=Nc1c(F)c(F)c(S(=O)(=O)NCCS(=O)(=O)[O-])c(F)c1F]

Embodiment 216 is a method of preparing a charged compound modified substrate or zwitterion modified substrate comprising:
a) contacting a substrate with an alcohol for a time sufficient for the alcohol to saturate the substrate;
b) incubating the saturated substrate with a solution comprising a charged or zwitterion compound for at least 30 seconds; and
c) exposing the substrate of step b) under a light source for at least 30 seconds, thereby generating the charged compound modified substrate or zwitterion modified substrate.

Embodiment 217 is the method of embodiment 216, wherein the alcohol comprises methanol, ethanol, 1-propanol, 2-propanol, 2-methyl-2-propanol, 3-methyl-1-butanol, 2,2-dimethyl-1-propanol, cyclopentanol, 1-hexanol, cyclohexanol, acetone, methyl ethyl ketone, dimethyl sulfoxide, dimethylformamide, N-methylpyrrolidone, dimethylacetamide, or diethyl carbonate.

Embodiment 218 is the method of embodiment 216 or 217, wherein the alcohol is ethanol.

Embodiment 219 is the method of any one of the embodiments 216-218, wherein the alcohol comprises less than 10%, 9%, 8%, 7%, 6%, 5%, 4%, 3%, 2%, 1%, 0.5%, or 0.05% water.

Embodiment 220 is the method of any one of the embodiments 216-219, wherein the time sufficient for the alcohol to saturate the substrate is about 2 seconds, 3 seconds, about 4 seconds, about 5 seconds, about 10 seconds, about 15 seconds, about 20 seconds, or more.

Embodiment 221 is the method of embodiment 216, wherein the incubating of step b) is for at least 1 minutes, at least 1.5 minutes, at least 2 minutes, at least 3 minutes, at least 4 minutes, at least 5 minutes, at least 10 minutes, at least 15 minutes, or at least 20 minutes.

Embodiment 222 is the method of embodiment 216, wherein the charged or zwitterion compound is a compound that has the structure of Formula I:

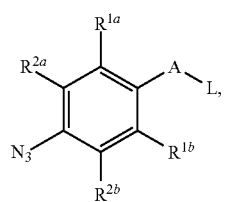

Formula I wherein
A is selected from —C(=O)— and —(SO$_2$)—;
L is selected from —OQ, —O$^-$, —N$^+$R$^3$HQ and —NR$^3$Q;
Q is a structure represented by a formula:

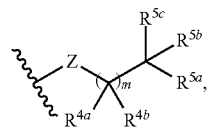

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of $R^{1a}$ and $R^{1b}$ is independently selected from hydrogen and halogen;

each of $R^{2a}$ and $R^{2b}$ is halogen;

$R^3$, when present, is selected from hydrogen and C1-C4 alkyl;

each of $R^{4a}$ and $R^{4b}$, when present, is independently selected from hydrogen, halogen, —CN, —OH, —$NR^{8a}R^{8b}$, —$NR^{8a}R^{8b}$ H⁺, C1-C4 alkyl, C1-C4 monohaloalkyl, C1-C4 polyhaloalkyl, —$SO_3^-$, —$SO_3R^9$, —$CO_2^-$, and —$CO_2R^9$;

each of $R^{5a}$, $R^{5b}$, and $R^{5c}$ is independently selected from hydrogen, halogen, —CN, —OH, —$NR^{10a}R^{10b}$, —$NR^{10a}R^{10b}R^{10c+}$, C1-C4 alkyl, C1-C4 monohaloalkyl, C1-C4 polyhaloalkyl, —$SO_3^-$, —$SO_3R^{11}$, —$CO_2^-$, and —$CO_2R^{11}$;

each of $R^{6a}$ and $R^{6b}$, when present, is independently selected from hydrogen, halogen, —CN, —OH, —$NR^{12a}R^{12b}$, —$NR^{12a}R^{12b}$ H⁺, C1-C4 alkyl, C1-C4 monohaloalkyl, C1-C4 polyhaloalkyl, —$SO_3^-$, —$SO_3R^{13}$, —$CO_2^-$, and —$CO_2R^{13}$;

$R^7$, when present, is selected from hydrogen and C1-C4 alkyl;

each of $R^{8a}$ and $R^{8b}$, when present, is independently selected from hydrogen and C1-C4 alkyl;

$R^9$, when present, is selected from hydrogen and C1-C4 alkyl;

each of $R^{10a}$, $R^{10b}$, and $R^{10c}$ when present, is independently selected from hydrogen, C1-C4 alkyl, —(C1-C8alkylene)$SO_3^-$, —(C1-C8alkylene)$SO_3H$, —(C1-C8alkylene)$CO_2^-$, and —(C1-C8alkylene)$CO_2H$;

$R^{11}$, when present, is selected from hydrogen and C1-C4 alkyl;

each of $R^{12a}$ and $R^{12b}$, when present, is independently selected from hydrogen and C1-C4 alkyl;

$R^{13}$, when present, is selected from hydrogen and C1-C4 alkyl, and provided that the compound is charged or zwitterionic.

Embodiment 223 is the method of embodiment 222, wherein the compound has a structure selected from:

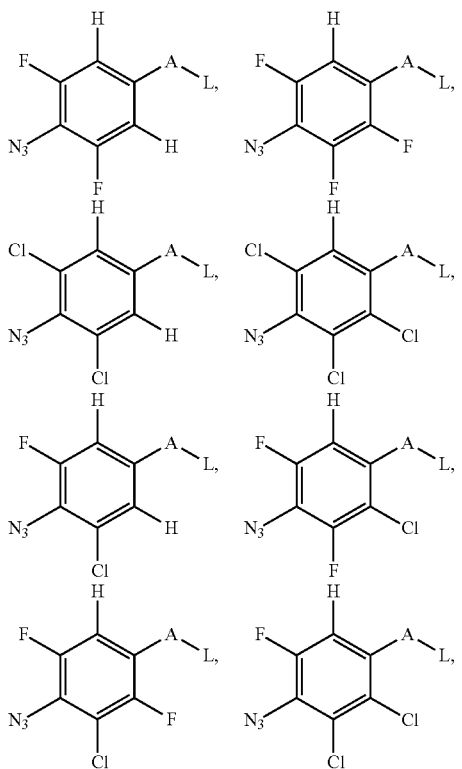

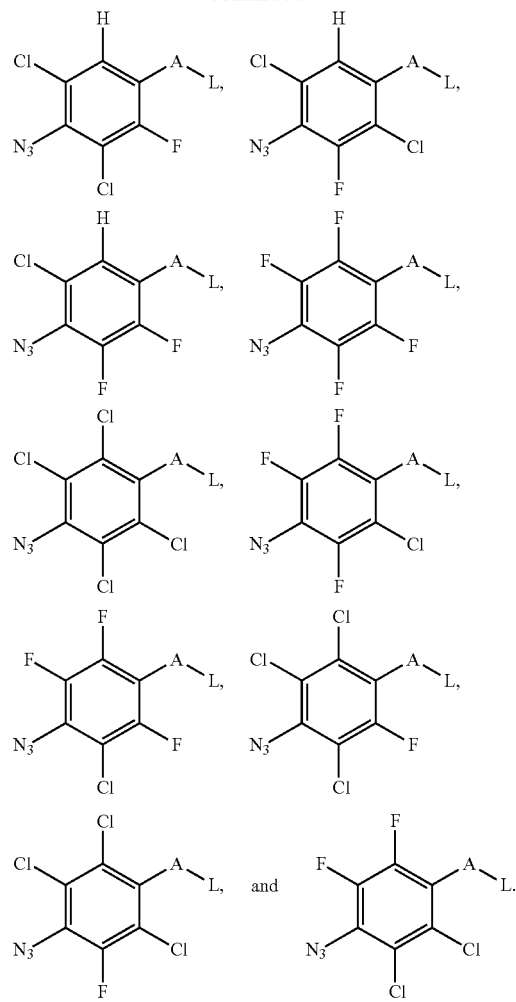

Embodiment 224 is the method of embodiment 222 or 223, wherein the compound has a structure selected from:

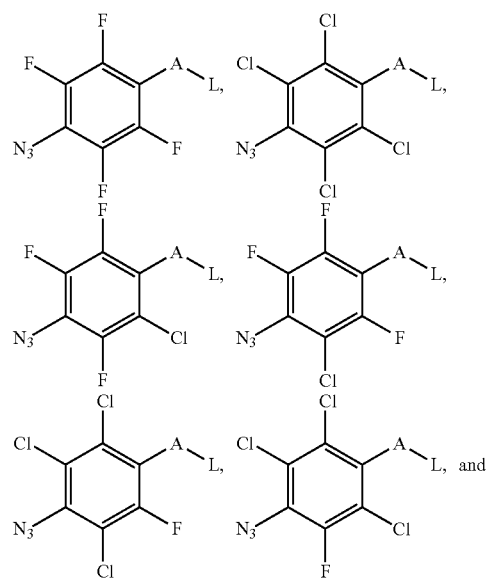

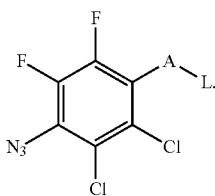

Embodiment 225 is the method of any one of the embodiments 222-224, wherein the compound has the following structure:

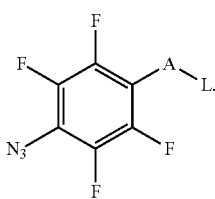

Embodiment 226 is the method of embodiment 222, wherein the compound has the structure selected from:

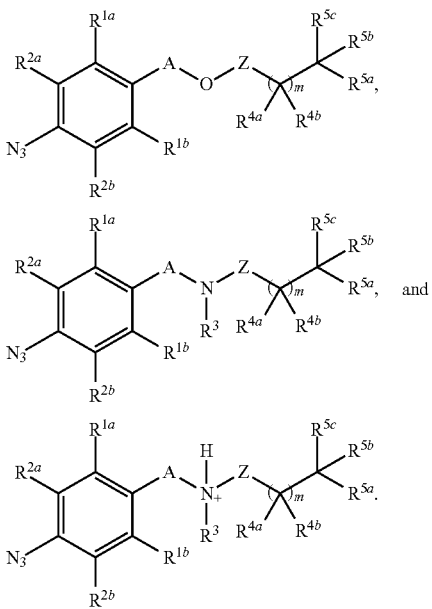

Embodiment 227 is the method of embodiment 222, wherein the compound has the following structure:

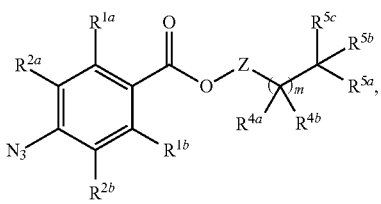

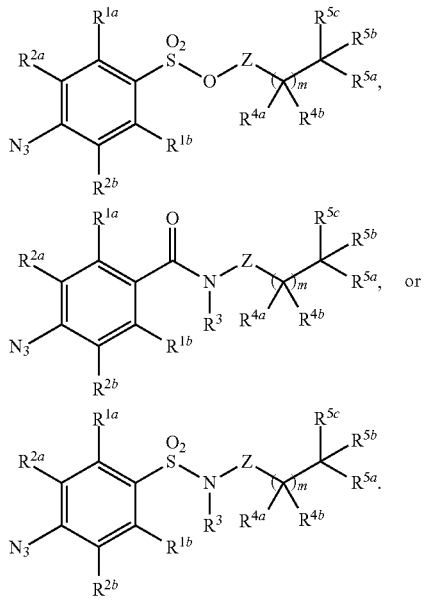

Embodiment 228 is the method of embodiment 226 or 227, wherein $R^{1a}$, $R^{10b}$, $R^{2a}$, and $R^{2b}$ are each —F.

Embodiment 229 is the method of any one of the embodiments 181-228, wherein Q is selected from:

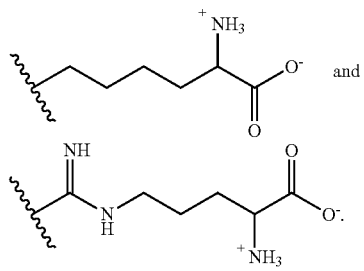

Embodiment 230 is the method of any one of the embodiments 222-228, wherein Q is:

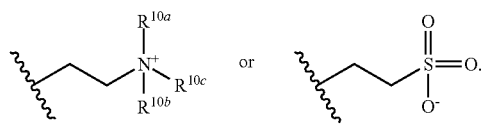

Embodiment 231 is the method of any one of the embodiments 222-228, wherein Z is —$CR^{6a}R^{6b}$—.

Embodiment 232 is the method of embodiment 231, wherein $R^{6a}$ and $R^{6b}$ are each hydrogen.

Embodiment 233 is the method of any one of embodiments 222-228 and 231-232, wherein m is 0, 1, 2, or 3.

Embodiment 234 is the method of embodiment 233, wherein m is 0.

Embodiment 235 is the method of any one of the embodiments 222-228 and 231-234, wherein $R^{5a}$ is —$NR^{10a}R^{10b}R^{10c+}$; $R^{5b}$ is hydrogen; and $R^{5c}$ is hydrogen.

Embodiment 236 is the method of embodiment 222, wherein the compound has the structure of Formula Ia:

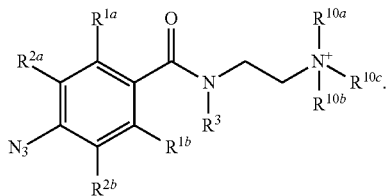

Embodiment 237 is the method of embodiment 222, wherein the compound has the structure of Formula Ib:

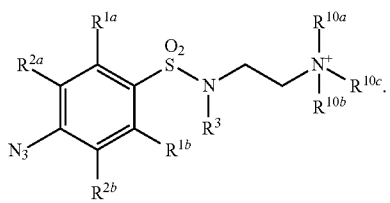

Embodiment 238 is the method of embodiments 236 or 237, wherein $R^{10c}$ is —(C1-C8alkylene)$SO_3^-$, —(C1-C8alkylene)$SO_3H$, —(C1-C8alkylene)$CO_2^-$, or —(C1-C8alkylene)$CO_2H$.

Embodiment 239 is the method of any one of embodiments 236-238, wherein $R^{10c}$ is —$CH_2CH_2CH_2$—$SO_3^-$, —$CH_2CH_2CH_2$—$SO_3H$, —$CH_2CH_2CH_2$—$CO_2^-$, or —$CH_2CH_2CH_2$—$CO_2H$.

Embodiment 240 is the method of any one of embodiments 236-239, wherein $R^{10a}$ and $R^{10b}$ are each C1-C4alkyl.

Embodiment 241 is the method of embodiment 240, wherein $R^{10a}$ and $R^{10b}$ are each methyl.

Embodiment 242 is the method of any one of embodiments 236-241, wherein $R^3$ is hydrogen.

Embodiment 243 is the method of embodiment 236, wherein the zwitterionic compound is

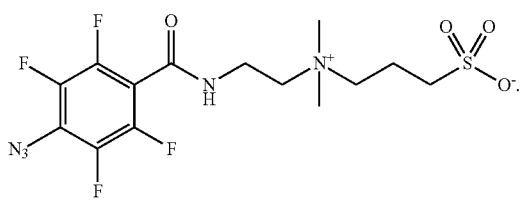

Embodiment 244 is the method of embodiment 236, wherein the charged compound is

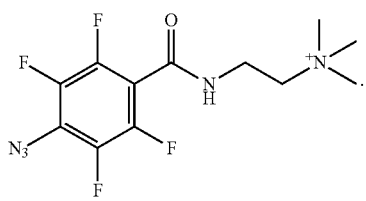

Embodiment 245 is the method of embodiment 230, wherein the charged compound is

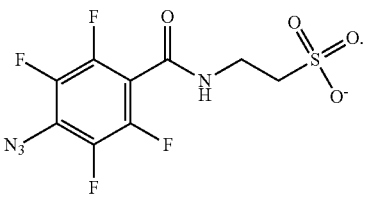 [SMILES: [N-]=[N+]=Nc1c(F)c(F)c(C(=O)NCCS(=O)(=O)[O-])c(F)c1F]

Embodiment 246 is the method of embodiment 237, wherein the zwitterionic compound is

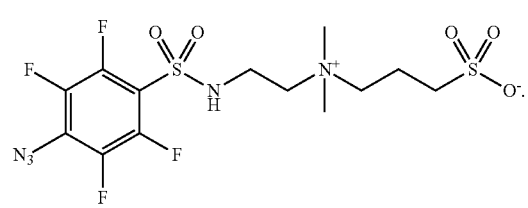

Embodiment 247 is the method of embodiment 237, wherein the charged compound is

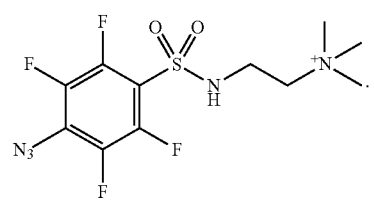 [SMILES: C[N+](C)(C)CCNS(=O)(=O)c1c(F)c(F)c(N=[N+]=[N-])c(F)c1F]

Embodiment 248 is the method of embodiment 230, wherein the charged compound is

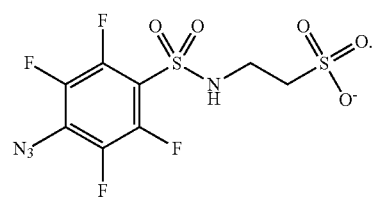 [SMILES: [N-]=[N+]=Nc1c(F)c(F)c(S(=O)(=O)NCCS(=O)(=O)[O-])c(F)c1F]

Embodiment 249 is the method of embodiment 222, wherein the charged compound is

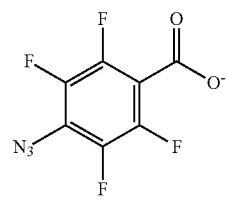 [SMILES: [N-]=[N+]=Nc1c(F)c(F)c(C(=O)[O-])c(F)c1F]

Embodiment 250 is the method of embodiment 222, wherein the charged compound is

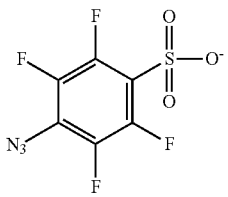 [SMILES: [N-]=[N+]=Nc1c(F)c(F)c(S(=O)(=O)[O-])c(F)c1F]

Embodiment 251 is the method of any one of the embodiments 216 or 222-250, wherein the concentration of the charged or zwitterion compound in the solution is between 0.1 mM and 5 mM, between 0.1 mM and 4 mM, between 0.1 mM and 3 mM, between 0.1 mM and 2 mM, between 0.1 mM and 1 mM, between 0.5 mM and 5 mM, between 0.5 mM and 4 mM, between 0.5 mM and 3 mM, between 0.5 mM and 2 mM, between 0.5 mM and 1 mM, between 1 mM and 5 mM, between 1 mM and 4 mM, between 1 mM and 3 mM, between 1 mM and 2 mM, between 1.5 mM and 5 mM, between 1.5 mM and 4 mM, between 1.5 mM and 3 mM, between 1.5 mM and 2 mM, between 2 mM and 5 mM, between 2 mM and 4 mM, between 2 mM and 3 mM, between 3 mM and 5 mM, between 3 mM and 4 mM, or between 4 mM and 5 mM.

Embodiment 252 is the method of any one of the embodiments 216 or 222-250, wherein the concentration of the charged or zwitterion compound in the solution is about 0.1 mM, about 0.5 mM, about 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.5 mM, 4 mM, 4.5 mM, or 5 mM.

Embodiment 253 is the method of embodiment 216, wherein the exposing of step b) under a light source is for at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 254 is the method of embodiment 216 or 253, wherein the light source is an ultraviolet light source.

Embodiment 255 is the method of embodiment 254, wherein the ultraviolet light source has an intensity of at least 900 µW/cm$^2$.

Embodiment 256 is the method of embodiment 254 or 255, wherein the ultraviolet light source has a wavelength of between 240 nm and 280 nm, between 240 nm and 275 nm, between 240 nm and 270 nm, between 240 nm and 265 nm, between 240 nm and 260 nm, between 240 nm and 255 nm, between 240 nm and 250 nm, between 240 nm and 245 nm, between 250 nm and 280 nm, between 250 nm and 275 nm, between 250 nm and 270 nm, between 250 nm and 265 nm, between 250 nm and 260 nm, between 255 nm and 280 nm, between 255 nm and 275 nm, between 255 nm and 270 nm, between 255 nm and 265 nm, between 255 nm and 260 nm, between 260 nm and 280 nm, between 260 nm and 275 nm, between 260 nm and 270 nm, or between 270 nm and 280 nm.

Embodiment 257 is the method of embodiment 254 or 255, wherein the ultraviolet light source has a wavelength of at least 240 nm, 245 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 275 nm or 280 nm.

Embodiment 258 is the method of any one of the embodiments 216-257, further comprising incubating the charged compound modified substrate or zwitterion modified substrate in a water-alcohol solution after exposure with the light source of step c).

Embodiment 259 is the method of embodiment 258, wherein the water-alcohol solution comprises a water to alcohol ratio of about 90:10, 80:20, 70:30, 60:40, 50:50, 40:60, 33:67, 30:70, 20:80 or 10:90.

Embodiment 260 is the method of embodiment 259, wherein the alcohol comprises methanol, ethanol, 1-propanol, 2-propanol, 2-methyl-2-propanol, 3-methyl-1-butanol, 2,2-dimethyl-1-propanol, cyclopentanol, 1-hexanol or cyclohexanol.

Embodiment 261 is the method of embodiment 260, wherein the incubating further comprises sonicating the charged compound modified substrate or zwitterion modified substrate in the water-alcohol solution.

Embodiment 262 is the method of embodiment 261, wherein the sonication is for at least 1 minutes, 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

Embodiment 263 is the method of embodiment 260, further comprising drying the charged compound modified substrate or zwitterion modified substrate under vacuum after incubation in the second water-alcohol solution.

Embodiment 264 is the method of embodiment 216, wherein the substrate comprises a separator.

Embodiment 265 is the method of embodiment 264, wherein the separator comprises a polymer-based separator.

Embodiment 266 is the method of embodiment 265, wherein the polymer-based separator comprises a polyolefinic separator.

Embodiment 267 is the method of embodiment 266, wherein the polyolefinic separator comprises a separator modified with polyethylene (PE), polypropylene (PP), polyamide (PA), polytetrafluoroethylene (PTFE), polyvinylidene fluoride (PVDF), polyvinyl chloride (PVC), or a combination thereof.

Embodiment 268 is the method of any one of the embodiments 264-267, wherein the separator comprises a microporous separator, a nonwoven separator, an ion-exchange membrane, a supported liquid membrane, or a solid ion conductor.

Embodiment 269 is the method of embodiment 216, wherein the substrate comprises a carbon-based substrate containing a moiety capable of binding with the perfluorophenylazide charged or zwitterion derivative of Formula I.

Embodiment 270 is the method of embodiment 269, wherein the carbon-based substrate comprises a polymer moiety.

Embodiment 271 is the method of embodiment 269, wherein the carbon-based substrate comprises a polyolefin moiety.

Embodiment 272 is the method of embodiment 271, wherein the polyolefin moiety comprises a polyethylene (PE) moiety, a polypropylene (PP) moiety, a polyamide (PA) moiety, a polytetrafluoroethylene (PTFE) moiety, a polyvinylidene fluoride (PVDF) moiety, or a polyvinyl chloride (PVC) moiety.

Embodiment 273 is the method of any one of the embodiments 216-272, wherein the method is an automated method.

Embodiment 274 is the method of any one of the embodiments 216-273, wherein the method is carried out at room temperature.

Embodiment 275 is the method of any one of the embodiments 216-273, wherein the method is carried out at a temperature within 20° C. and 30° C., 20° C. and 28° C., 20° C. and 26° C., 20° C. and 25° C., 22° C. and 30° C., 22° C. and 28° C., 22° C. and 26° C., 22° C. and 25° C., 24° C. and 30° C., 24° C. and 28° C., or 24° C. and 26° C.

Embodiment 276 is the method of any one of the embodiments 216-273, wherein the method is carried out at about 20° C., about 21° C., about 22° C., about 23° C., about 24° C., about 25° C., about 26° C., about 27° C., about 28° C., about 29° C., or about 30° C.

Embodiment I is an energy providing device comprising a charged compound modified substrate or zwitterion-modified substrate.

Embodiment II is the energy providing device of embodiment I, wherein the charged compound modified substrate or zwitterion-modified substrate comprises a compound that has the structure of Formula I:

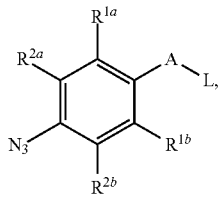

Formula I wherein

A is selected from —C(=O)— and —(SO$_2$)—;

L is selected from —OQ, —O$^-$, —N$^+$R$^3$HQ and —NR$^3$Q;

Q is a structure represented by a formula:

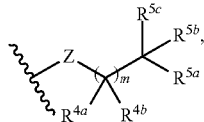

Z is selected from —CR$^{6a}$R$^{6b}$—, —C(=O)—, —C(=NH)—, and —C(=NH)NR$^7$—;

m is an integer selected from 0, 1, 2, 3, 4, 5, 6, 7, and 8;

each of R$^{1a}$ and R$^{1b}$ is independently selected from hydrogen and halogen;

each of R$^{2a}$ and R$^{2b}$ is halogen;

R$^3$, when present, is selected from hydrogen and C1-C4 alkyl;

each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;

each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;

each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;

R$^7$, when present, is selected from hydrogen and C1-C4 alkyl;

each of R$^{8a}$ and R$^{8b}$, when present, is independently selected from hydrogen and C1-C4 alkyl;

R$^9$, when present, is selected from hydrogen and C1-C4 alkyl;

each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;

R$^{11}$, when present, is selected from hydrogen and C1-C4 alkyl;

each of R$^{12a}$ and R$^{12b}$, when present, is independently selected from hydrogen and C1-C4 alkyl;

R$^{13}$, when present, is selected from hydrogen and C1-C4 alkyl, and provided that the compound is charged or zwitterionic.

Embodiment III is the energy providing device of embodiment II, wherein the compound has a structure selected from:

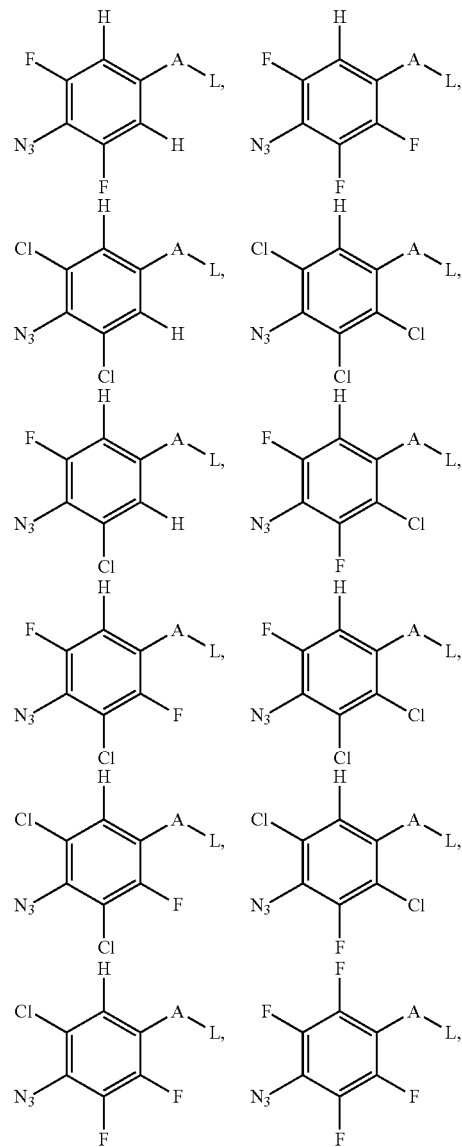

-continued
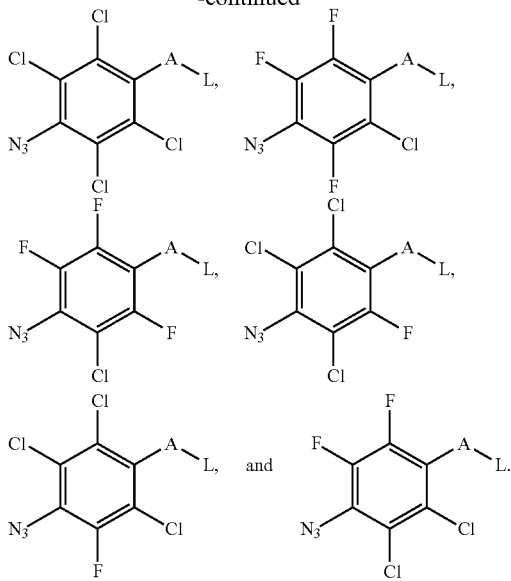
Embodiment IV is the energy providing device of embodiment II, wherein the compound has the structure selected from:
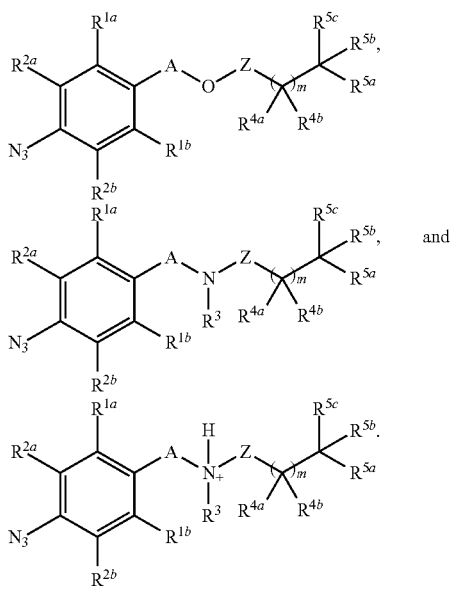
Embodiment V is the energy providing device of embodiment II, wherein Q is selected from:
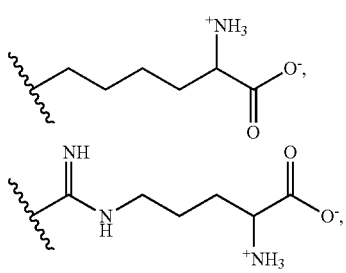
-continued
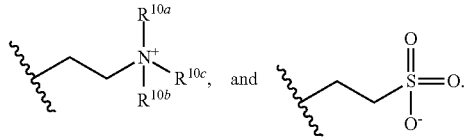
Embodiment VI is the energy providing device of embodiment II, wherein the compound of Formula I is:
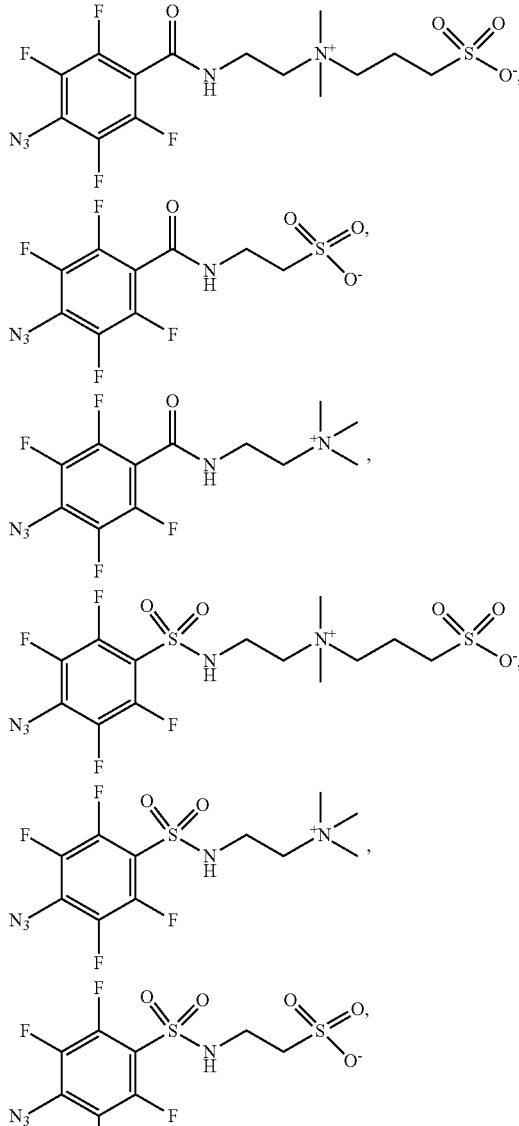
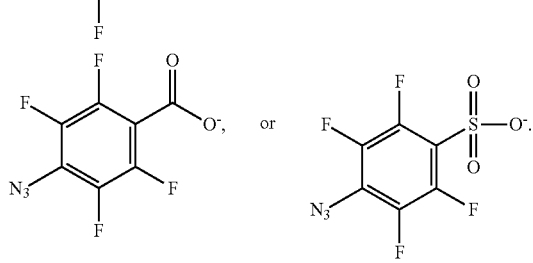

Embodiment VII is the energy providing device of embodiment I or II, wherein the substrate comprises a separator.

Embodiment VIII is the energy providing device of embodiment I or II, further comprising an electrolyte disposed onto the charged compound modified substrate or zwitterion modified substrate.

Embodiment IX is the energy providing device of embodiment I or II, further comprising an electrode.

Embodiment X is the energy providing device of any one of the embodiments I-IX, wherein the energy providing device comprises a battery, a supercapacitor, or a fuel cell.

Embodiment XI is a method of preparing a charged compound modified substrate or zwitterion modified substrate comprising:
a) contacting a substrate with an alcohol for a time sufficient for the alcohol to saturate the substrate;
b) incubating the saturated substrate with a solution comprising a charged or zwitterionic compound for at least 30 seconds; and
c) exposing the substrate of step b) under a light source for at least 30 seconds, thereby generating the charged compound modified substrate or zwitterion modified substrate.

Embodiment XII is the method of embodiment XI, wherein the charged or zwitterionic compound is a compound that has the structure of Formula I:

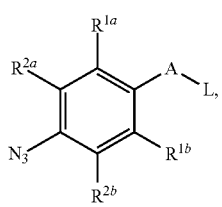

Formula I wherein
A is selected from —C(=O)— and —(SO$_2$)—;
L is selected from —OQ, —O$^-$, —N$^+$R$^3$HQ and —NR$^3$Q;
Q is a structure represented by a formula:

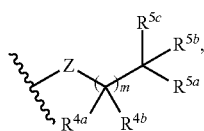

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of R$^{1a}$ and R$^{1b}$ is independently selected from hydrogen and halogen;
each of R$^{2a}$ and R$^{2b}$ is halogen;
R$^3$, when present, is selected from hydrogen and C1-C4 alkyl;
each of R$^{4a}$ and R$^{4b}$, when present, is independently selected from hydrogen, halogen, —CN, —OH, —NR$^{8a}$R$^{8b}$, —NR$^{8a}$R$^{8b}$ H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;
each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;
each of R$^{6a}$ and R$^{6b}$, when present, is independently selected from hydrogen, halogen, —CN, —OH, —NR$^{12a}$R$^{12b}$, —NR$^{12a}$R$^{12b}$ H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;
R$^7$, when present, is selected from hydrogen and C1-C4 alkyl;
each of R$^{8a}$ and R$^{8b}$, when present, is independently selected from hydrogen and C1-C4 alkyl;
R$^9$, when present, is selected from hydrogen and C1-C4 alkyl;
each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;
R$^{11}$, when present, is selected from hydrogen and C1-C4 alkyl;
each of R$^{12a}$ and R$^{12b}$, when present, is independently selected from hydrogen and C1-C4 alkyl;
R$^{13}$, when present, is selected from hydrogen and C1-C4 alkyl, and
provided that the compound is charged or zwitterionic.

Embodiment XIII is the method of embodiment XII, wherein the charged or zwitterionic compound is:

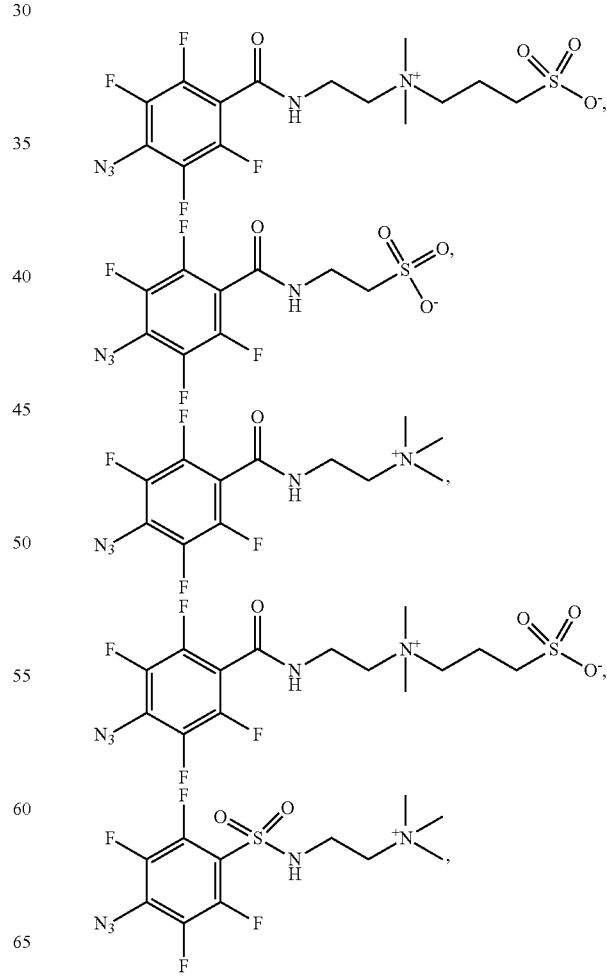

-continued

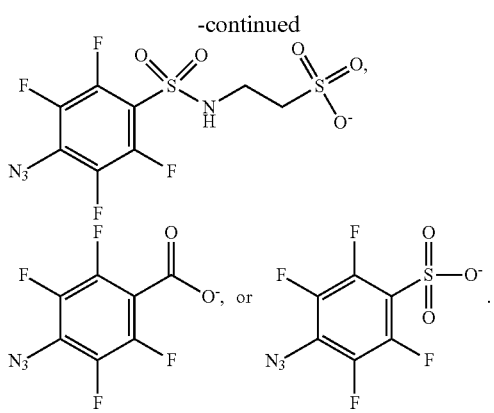

Embodiment XIV is the method of any one of the embodiments XII-XIII, wherein the time sufficient for the alcohol to saturate the substrate is about 2 seconds, 3 seconds, about 4 seconds, about 5 seconds, about 10 seconds, about 15 seconds, about 20 seconds, or more.

Embodiment XV is the method of any one of embodiments XII-XIV, wherein the incubating of step b) is for at least 1 minutes, at least 1.5 minutes, at least 2 minutes, at least 3 minutes, at least 4 minutes, at least 5 minutes, at least 10 minutes, at least 15 minutes, or at least 20 minutes.

Embodiment XVI is the method of any one of the embodiments XII-XV, wherein the light source is an ultraviolet light source.

Embodiment XVII is the method of any one of the embodiments XII-XVI, further comprising incubating the charged compound modified substrate or zwitterion modified substrate in a water-alcohol solution after exposure with the light source of step c).

Embodiment XVIII is the method of any one of the embodiments XII-XVII, wherein the substrate comprises a separator.

Embodiment XIX is a charged or zwitterionic compound that has the structure of Formula IIa or Formula IIb:

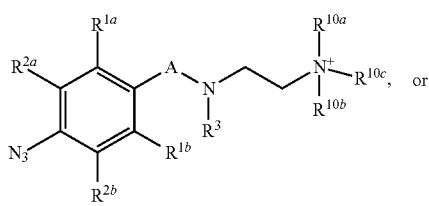

Formula IIa

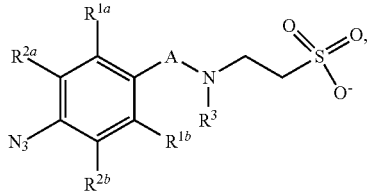

Formula IIb wherein
A is selected from —C(=O)— and —(SO$_2$)—;
each of $R^{1a}$ and $R^{1b}$ is independently selected from hydrogen and halogen;
each of $R^{2a}$ and $R^{2b}$ is halogen;
$R^3$ is selected from hydrogen and C1-C4 alkyl;

$R^{10a}$ and $R^{10b}$ are independently selected from C1-C4 alkyl; and
$R^{10c}$ is selected from C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H.

Embodiment XX is the compound of embodiment XIX, wherein the compound is:

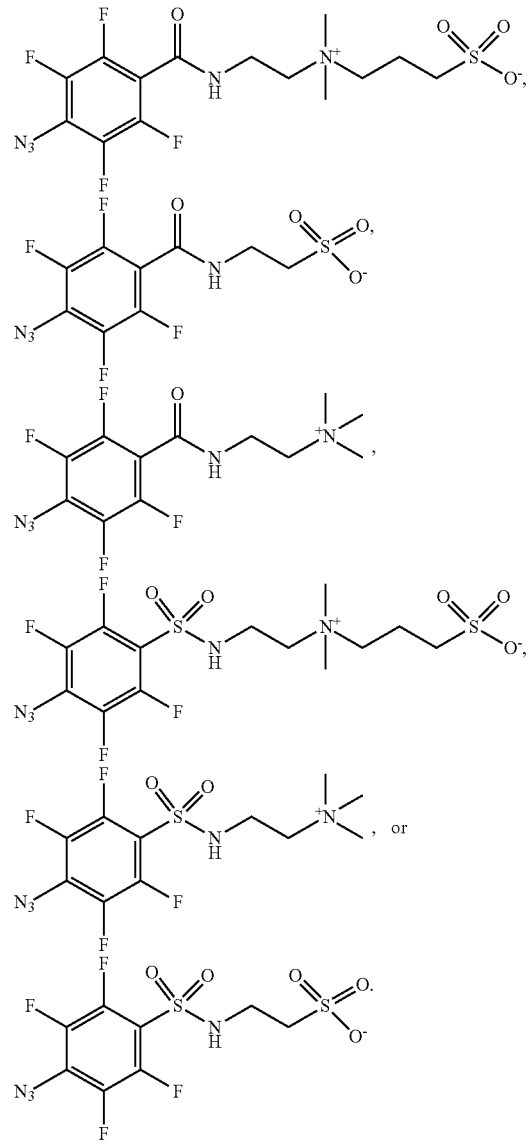

What is claimed is:

1. A method of preparing a charged compound modified substrate or zwitterion modified substrate comprising:
   a) incubating the substrate with a solution comprising a charged or zwitterion compound for at least 40 minutes; and
   b) exposing the treated substrate of step a) under a light source for at least one minute, thereby generating the charged compound modified substrate or zwitterion modified substrate.

2. The method of claim 1, wherein the incubating of step a) is for at least 45 minutes, at least 50 minutes, at least 55 minutes, at least 60 minutes, at least 65 minutes, at least 70 minutes, at least 80 minutes, at least 90 minutes, or at least 120 minutes.

3. The method of claim 1, wherein the incubating of step a) further comprises heating the substrate with the charged or zwitterion compound at a temperature of between 45° C. and 80° C., between 45° C. and 70° C., between 45° C. and 65° C., between 45° C. and 60° C., between 45° C. and 55° C., between 45° C. and 50° C., between 50° C. and 80° C., between 50° C. and 70° C., between 50° C. and 60° C., between 55° C. and 80° C., between 55° C. and 70° C., between 55° C. and 60° C., between 60° C. and 80° C. or between 60° C. and 70° C.

4. The method of claim 1, wherein the exposing of step b) under a light source is for at least 2 minutes, 3 minutes, 4 minutes, 5 minutes, 6 minutes, 7 minutes, 8 minutes, 9 minutes, 10 minutes, 15 minutes, 20 minutes, 25 minutes or 30 minutes.

5. The method of claim 4, wherein the light source is an ultraviolet light source.

6. The method of claim 1, wherein the solution of step a) is a first water-alcohol solution.

7. The method of claim 1, wherein the charged or zwitterion compound is a compound that has the structure of Formula I:

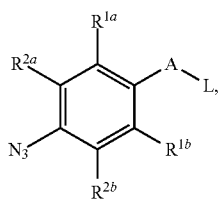

Formula I wherein
A is selected from —C(=O)— and —(SO$_2$)—;
L is selected from —OQ, —O$^-$, —N$^+$R$^3$HQ and —NR$^3$Q;
Q is a structure represented by a formula:

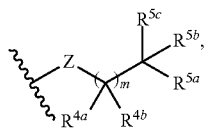

Z is selected from —CR$^{6a}$R$^{6b}$—, —C(=O)—, —C(=NH)—, and —C(=NH)NR$^7$—;
m is an integer selected from 0, 1, 2, 3, 4, 5, 6, 7, and 8;
each of R$^{1a}$ and R$^{1b}$ is independently selected from hydrogen and halogen;
each of R$^{2a}$ and R$^{2b}$ is halogen;
R$^3$, when present, is selected from hydrogen and C1-C4 alkyl;
each of R$^{4a}$ and R$^{4b}$, when present, is independently selected from hydrogen, halogen, —CN, —OH, —NR$^{8a}$R$^{8b}$, —NR$^{8a}$R$^{8b}$H$^+$, C1-C4 alkyl, C1-C4 monohaloalkyl, C1-C4 polyhaloalkyl, —SO$_3^-$, —SO$_3$R$^9$, —CO$_2^-$, and —CO$_2$R$^9$;
each of R$^{5a}$, R$^{5b}$, and R$^{5c}$ is independently selected from hydrogen, halogen, —CN, —OH, —NR$^{10a}$R$^{10b}$, —NR$^{10a}$R$^{10b}$R$^{10c+}$, C1-C4 alkyl, C1-C4 monohaloalkyl, C1-C4 polyhaloalkyl, —SO$_3^-$, —SO$_3$R$^{11}$, —CO$_2^-$, and —CO$_2$R$^{11}$;

each of R$^{6a}$ and R$^{6b}$, when present, is independently selected hydrogen, halogen, —CN, —OH, —NR$^{12a}$R$^{12b}$, NR$^{12a}$R$^{12b}$H$^+$, C1-C4 alkyl, C1-C4 monohaloalkyl, C1-C4 polyhaloalkyl, —SO$_3^-$, —SO$_3$R$^{13}$, —CO$_2^-$, and —CO$_2$R$^{13}$;
R$^7$, when present, is selected from hydrogen and C1-C4 alkyl;
each of R$^{8a}$ and R$^{8b}$, when present, is independently selected from hydrogen and C1-C4 alkyl;
R$^9$, when present, is selected from hydrogen and C1-C4 alkyl;
each of R$^{10a}$, R$^{10b}$, and R$^{10c}$ when present, is independently selected from hydrogen, C1-C4 alkyl, —(C1-C8alkylene)SO$_3^-$, —(C1-C8alkylene)SO$_3$H, —(C1-C8alkylene)CO$_2^-$, and —(C1-C8alkylene)CO$_2$H;
R$^{11}$, when present, is selected from hydrogen and C1-C4 alkyl;
each of R$^{12a}$ and R$^{12b}$, when present, is independently selected from hydrogen and C1-C4 alkyl;
R$^{13}$, when present, is selected from hydrogen and C1-C4 alkyl, and
provided that the compound is charged or zwitterionic.

8. The method of claim 7, wherein the compound has a structure selected from:

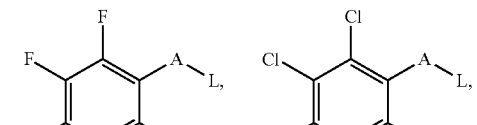

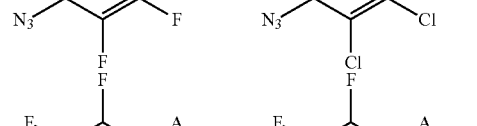

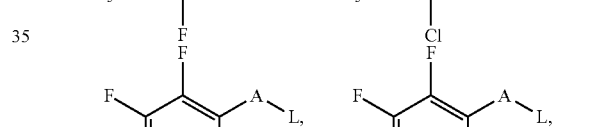

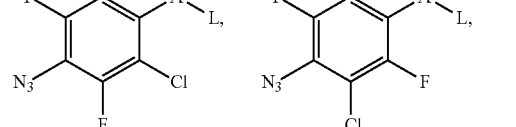

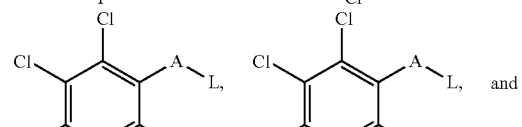

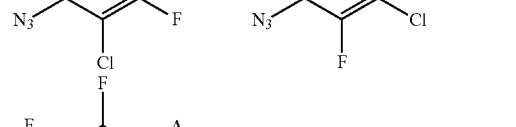

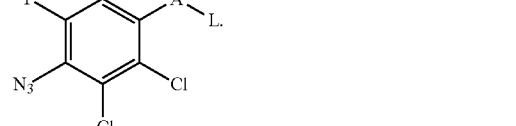

and

9. The method of claim 7, wherein Q is selected from:

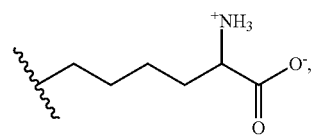

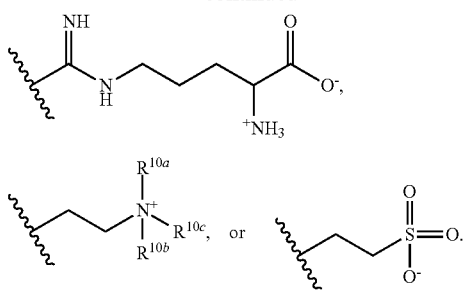

10. The method of claim 7, wherein the compound of Formula I is:

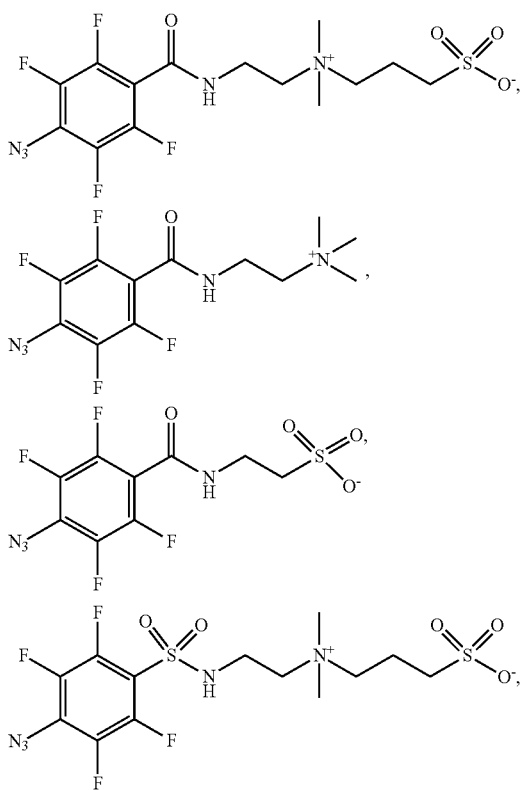

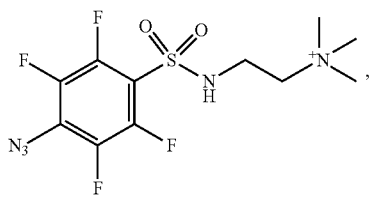

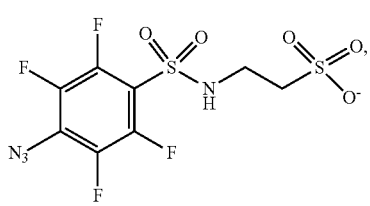

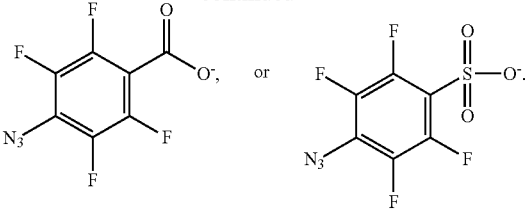

11. The method of claim 1, wherein the substrate comprises a separator.

12. The method of claim 11, wherein the separator comprises a polymer-based separator.

13. The method of claim 11, wherein the separator comprises a microporous separator, a nonwoven separator, an ion-exchange membrane, a supported liquid membrane, or a solid ion conductor.

14. A compound that has the structure of Formula IIa:

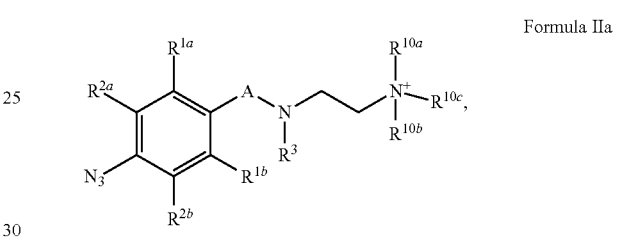

Formula IIa wherein
A is selected from —C(=O)— and —(SO$_2$)—;
each of R$^{1a}$ and R$^{1b}$ is independently selected from hydrogen and halogen;
each of R$^{2a}$ and R$^{2b}$ is halogen;
R$^3$ is selected from hydrogen and C1-C4 alkyl; and
R$^{10a}$, R$^{10b}$, and R$^{10c}$ are independently selected from C1-C4 alkyl.

15. The compound of claim 14, wherein R$^{1a}$, R$^{1b}$, R$^{2a}$, and R$^{2b}$ are each —F.

16. The compound of claim 14, wherein R$^3$ is hydrogen.

17. The compound of claim 14, wherein R$^{10a}$, R$^{10b}$ and R$^{10c}$ are each methyl.

18. A compound that has the structure of Formula IIb:

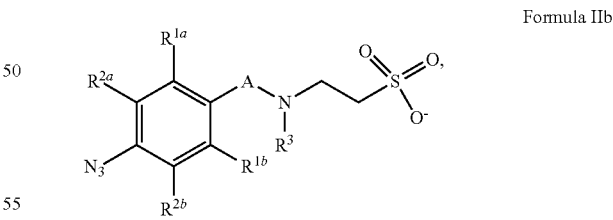

Formula IIb wherein
A is selected from —C(=O)— and —(SO$_2$)—;
each of R$^{1a}$ and R$^{1b}$ is independently selected from hydrogen and halogen;
each of R$^{2a}$ and R$^{2b}$ is halogen; and
R$^3$ is selected from hydrogen and C1-C4 alkyl.

19. The compound of claim 18, wherein R$^{1a}$, R$^{1b}$, R$^{2a}$, and R$^{2b}$ are each —F.

20. The compound of claim 18, wherein R$^3$ is hydrogen.

* * * * *